US011603394B2

(12) United States Patent
Hudalla et al.

(10) Patent No.: US 11,603,394 B2
(45) Date of Patent: Mar. 14, 2023

(54) TARGETED EFFECTOR PROTEINS AND USES THEREOF

(71) Applicant: University of Florida Research Foundation, Incorporated, Gainesville, FL (US)

(72) Inventors: Gregory Hudalla, Gainesville, FL (US); Sabrina Freeman, Gainesville, FL (US); Antonietta Restuccia, Edmond, OK (US); Margaret Mary Fettis, Gainesville, FL (US); Evelyn R. Bracho-Sanchez, San Francisco, CA (US); Shaheen Farhadi, Gainesville, FL (US); Benjamin G. Keselowsky, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 652 days.

(21) Appl. No.: 16/339,585

(22) PCT Filed: Oct. 4, 2017

(86) PCT No.: PCT/US2017/055076
§ 371 (c)(1),
(2) Date: Apr. 4, 2019

(87) PCT Pub. No.: WO2018/067660
PCT Pub. Date: Apr. 12, 2018

(65) Prior Publication Data
US 2019/0218264 A1 Jul. 18, 2019

Related U.S. Application Data

(60) Provisional application No. 62/478,880, filed on Mar. 30, 2017, provisional application No. 62/403,872, filed on Oct. 4, 2016.

(51) Int. Cl.
*C07K 14/47* (2006.01)
*C12N 9/02* (2006.01)
*C07K 14/00* (2006.01)
*C12N 15/00* (2006.01)
*A61K 38/00* (2006.01)

(52) U.S. Cl.
CPC .......... *C07K 14/4726* (2013.01); *C07K 14/00* (2013.01); *C12N 9/0069* (2013.01); *C12N 15/00* (2013.01); *C12Y 113/11052* (2013.01); *C12Y 113/12007* (2013.01); *A61K 38/00* (2013.01); *C07K 2319/33* (2013.01); *C07K 2319/73* (2013.01)

(58) Field of Classification Search
None
See application file for complete search history.

(56) References Cited

U.S. PATENT DOCUMENTS

| | | | |
|---|---|---|---|
| 2005/0074865 A1 | 4/2005 | Afeyan et al. |
| 2005/0220792 A1 | 10/2005 | Agou et al. |
| 2005/0260222 A1 | 11/2005 | Gupta et al. |
| 2007/0098701 A1 | 5/2007 | Okano et al. |
| 2008/0234177 A1 | 9/2008 | Bremer et al. |
| 2011/0294983 A1 | 12/2011 | Desmet et al. |
| 2011/0318372 A1 | 12/2011 | Andersen et al. |
| 2014/0187487 A1 | 7/2014 | Choichet et al. |
| 2017/0335311 A1 | 11/2017 | Gruskin et al. |
| 2018/0073007 A9 | 3/2018 | Gruskin et al. |
| 2020/0262882 A1 | 8/2020 | Hudalla et al. |

FOREIGN PATENT DOCUMENTS

| | | | |
|---|---|---|---|
| EP | 1748050 | * | 1/2007 |
| EP | 1748050 | A1 | 1/2007 |
| JP | 2005-537032 | A | 12/2005 |
| JP | 2009-515520 | A | 4/2009 |
| JP | 2011-520783 | A | 7/2011 |
| JP | 2012-514616 | A | 6/2012 |
| JP | 2015-528514 | A | 9/2015 |
| JP | 2016-040260 | A | 3/2016 |
| WO | WO 1999/012041 | A1 | 3/1999 |
| WO | WO 2003/090780 | A1 | 11/2003 |
| WO | WO 2004/019878 | A2 | 3/2004 |
| WO | WO 2007/058776 | A2 | 5/2007 |
| WO | WO 2009/143843 | A1 | 12/2009 |
| WO | WO 2010/078966 | A1 | 7/2010 |
| WO | WO 2011/034605 | A2 | 3/2011 |

(Continued)

OTHER PUBLICATIONS

Littlejohn et al., Protein Expression and Purification 19: 22-29 (2000).*
Inohara et al., Biochem. Biophys. Res. Comm. 376: 605-610 (2008).*
SnapGene, https://www.snapgene.com/resources/plasmid-files/?set=pgex_vectors_(ge_healthcare)&plasmid=pGEX-4T-1, accessed Nov. 4, 2021.*
Weisel et al., Subcell. Biochem. 82: 405-456 (2017).*

(Continued)

*Primary Examiner* — Erin M. Bowers
(74) *Attorney, Agent, or Firm* — Wolf, Greenfield & Sacks, P.C.

(57) ABSTRACT

Provided herein are targeted effector fusion proteins, complexes thereof, and uses thereof. The targeted effector fusion proteins can include an effector protein that can be linked to a targeting moiety. Monomer targeted effector fusion proteins can form homogeneous or heterogeneous complexes. The targeted effector fusion proteins and complexes thereof can be formulated as pharmaceutical formulations. The targeted effector fusion proteins, complexes thereof, and formulations thereof can be administered to a subject in need thereof.

26 Claims, 69 Drawing Sheets

Specification includes a Sequence Listing.

(56) References Cited

FOREIGN PATENT DOCUMENTS

| | | | |
|---|---|---|---|
| WO | WO 2014/043708 | A1 | 3/2014 |
| WO | WO 2014/089267 | A1 | 6/2014 |
| WO | WO 2016/127100 | A1 | 8/2016 |
| WO | WO 2016/172319 | A1 | 10/2016 |
| WO | WO 2018/067660 | A1 | 4/2018 |

OTHER PUBLICATIONS

Krylov et al., "Leucine Zipper", Encyclopedia of Life Sciences, John Wiley & Sons, 2001.*

Lee et al., Experimental & Molecular Medicine 46: e121 (2014).*

Extended European Search Report for Application No. EP 17859087.3, dated Apr. 8, 2020.

International Search Report and Written Opinion for Application No. PCT/US2017/055076, dated Feb. 21, 2018.

International Preliminary Report on Patentability for Application No. PCT/US2017/055076, dated Apr. 18, 2019.

Litowski, et al., Designing Heterodimeric Two-stranded alpha-Helical Coiled-coils. J Biol Chem 2002 277(40), 37272-9.

Weidle, et al. Fully Human Targeted Cytotoxic Fusion Proteins: New Anticancer Agents on the Horizon. Cancer Genomics Proteomics. 2012.

Wheeldon, et al. Substrate channeling as an approach to cascade reactions. Nat Chem. Apr. 8, 2016(4), 299-309.

Li, et al. Rate Enhancement of an Interfacial Biochemical Reaction through Localization of Substrate and Enzyme by an Adaptor Domain. J Phys Chem B. 2010. 114(46), 15113-8.

Liu, et al. Galectins as molulators of tumor progression. Nat. Rev. Cancer. 2005. 5(1), 29-41.

Liu, et al. Expression of immune checkpoint molecules in endometrial carcinoma. Exp. Ther Med. 2015. 10(5). 1947-1952.

Brooks, et al. Immunomodulatory Factors Galectin-9 and Interferon-Gamma Synergize to Induce Expression of Rate-Limiting Enzymes of the Kynurenine Pathway in the Mouse Hippocampus. Front Immunol. Oct. 17, 2016 7(422). 1-16.

U.S. Appl. No. 16/755,553, filed Apr. 10, 2020, Hudalla et al.

U.S. Appl. No. 17/434,616, filed Aug. 27, 2021, Hudalla et al.

U.S. Appl. No. 17/288,435, filed Apr. 23, 2021, Hudalla et al.

PCT/US2018/055213, dated Jan. 4, 2019, International Search Report and Written Opinion.

PCT/US2018/055213, dated Apr. 23, 2020, International Preliminary Report on Patentability.

PCT/US2020/020532, dated May 21, 2020, Invitation to Pay Additional Fees.

PCT/US2020/020532, dated Jul. 24, 2020, International Search Report and Written Opinion.

PCT/US2020/020532, dated Sep. 10, 2021, International Preliminary Report on Patentability.

PCT/US2019/058230, dated Feb. 5, 2020, International Search Report and Written Opinion.

PCT/US2019/058230, dated May 6, 2021, International Preliminary Report on Patentability.

International Search Report and Written Opinion dated Jan. 4, 2019 for Application No. PCT/US2018/055213.

International Preliminary Report on Patentability dated Apr. 23, 2020 for Application No. PCT/US2018/055213.

Invitation to Pay Additional Fees for Application No. PCT/US2020/020532, dated May 21, 2020.

International Search Report and Written Opinion for Application No. PCT/US2020/020532, dated Jul. 24, 2020.

International Preliminary Report on Patentability for Application No. PCT/US2020/020532, dated Sep. 10, 2021.

International Search Report and Written Opinion for Application No. PCT/US2019/058230, dated Feb. 5, 2020.

International Preliminary Report on Patentability for Application No. PCT/US2019/058230, dated May 6, 2021.

Fettis et al., Engineering Reactive Oxygen Species-Resistant Galectin-1 Dimers with Enhanced Lectin Activity. Bioconjug Chem. Jul. 18, 2018;29(7):2489-2496. doi: 10.1021/acs.bioconjchem.8b00425. Epub Jul. 3, 2018.

Iken et al., Indoleamine 2,3-dioxygenase and metabolites protect murine lung allografts and impair the calcium mobilization of T cells. Am J Respir Cell Mol Biol. Oct. 2012;47(4):405-16. doi: 10.1165/rcmb.2011-0438OC. Epub Apr. 19, 2012.

Li et al., Enhancement of an Interfacial Biochemical Reaction through Localization of Substrate and Enzyme by an Adaptor Domain. J Phys Chem B. 2010;114(46):15113-8.

Nishi et al., Functional and structural bases of a cysteine-less mutant as a long-lasting substitute for galectin-1. Glycobiology. Dec. 2008;18(12):1065-73. doi: 10.1093/glycob/cwn089. Epub Sep. 16, 2008.

Pechar et al., Coiled coil peptides and polymer-peptide conjugates: synthesis, self-assembly, characterization and potential in drug delivery systems. Biomacromolecules. Jul. 14, 2014;15(7):2590-9. doi: 10.1021/bm500436p. Epub Jun. 3, 2014.

* cited by examiner

FIG. 3A
FIG. 3B
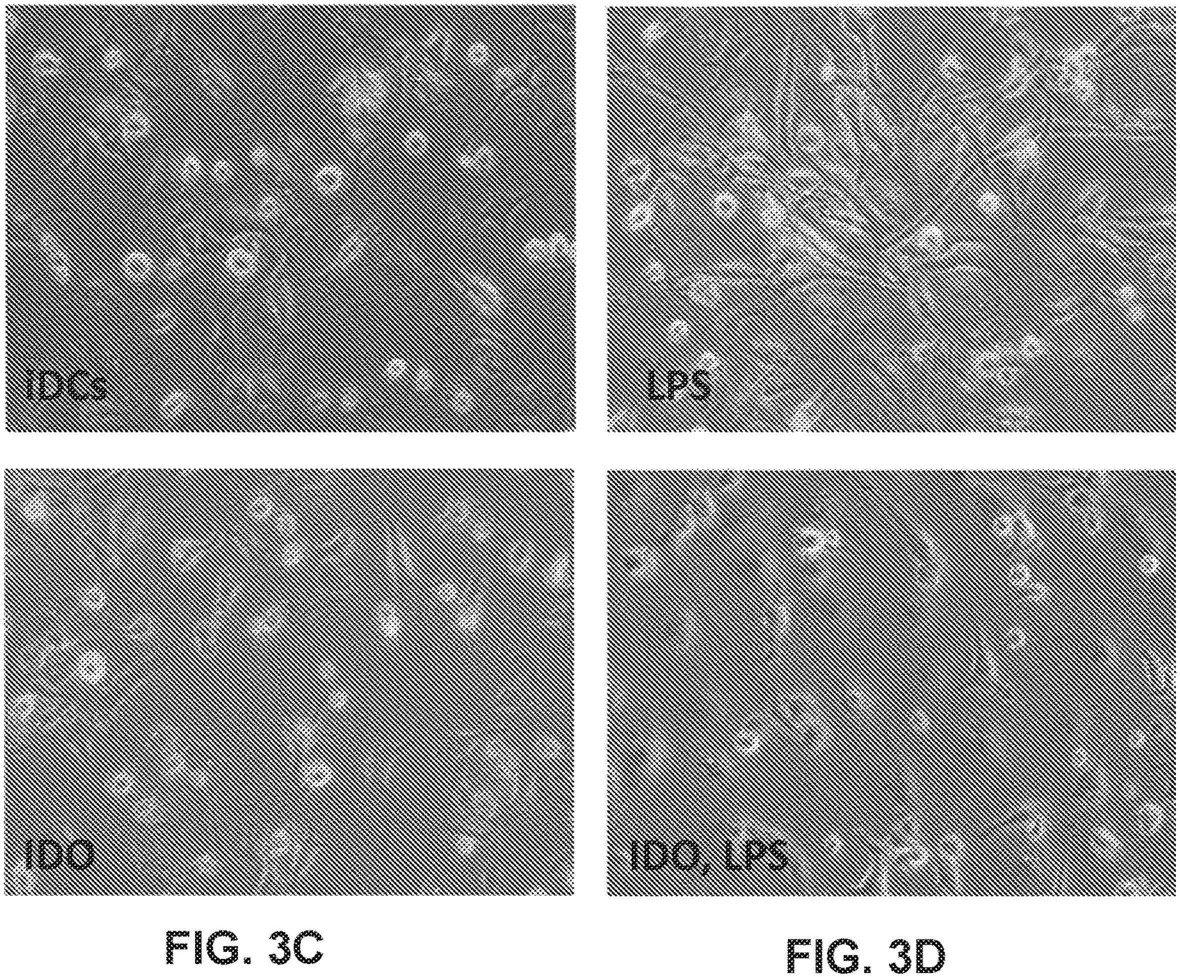
FIG. 3C
FIG. 3D
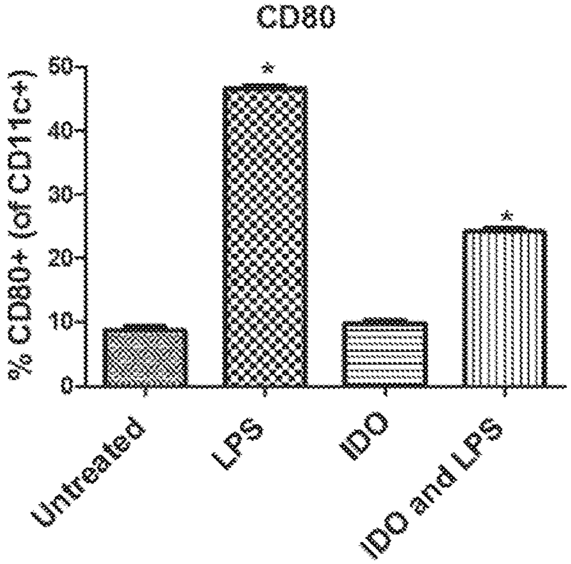
FIG. 4

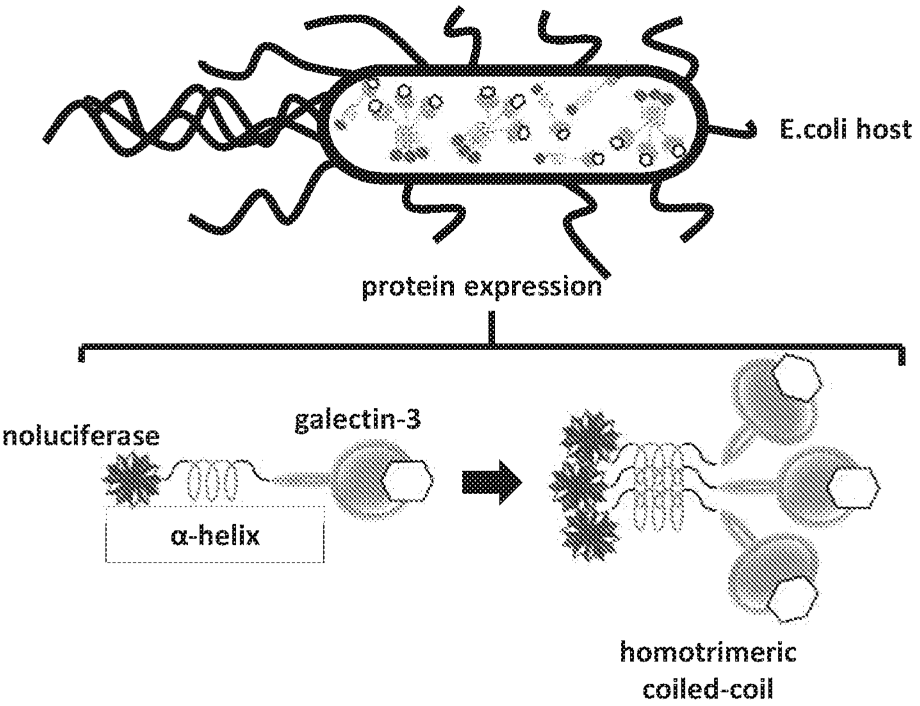

FIG. 46

SEQ ID NO: 1

M A V F T L E D F V G D W R Q T A G Y N L D Q V L E Q G G V S S L F Q N L G V
S V T P I Q R I V L S G E N G L K I D I H V I I P Y E G L S G D Q M G Q I E K I F K
V V Y P V D D H H F K V I L H Y G T L V I D G V T P N M I D Y F G R P Y E G I A V
F D G K K I T V T G T L W N G N K I I D E R L I N P D G S L L F R V T I N G V T G
W R L C E R I L A G S *G G G S G G S G G S G G* *M A R M K Q L E D K V E E L L*
*S K N Y H L E N R V A R L E K L V G E R* *G G G S G G S G G G G S G G S G* E F
A D N F S L H D A L S G S G N P N P Q G W P G A W G N Q P A G A G G Y P G
A S Y P G A Y P G Q A P P G A Y P G Q A P P G A Y P G A P G A Y P G A P A P
G V Y P G P P S G P G A Y P S S G Q P S A P G A Y P A T G P Y G A P A G P L I
V P Y N L P L P G G V V P R M L I T I L G T V K P N A N R I A L D F Q R G N D V
A F H F N P R F N E N N R R V I V C N T K L D N N W G R E E R Q S V F P F E S
G K P F K I Q V L V E P D H F K V A V N D A H L L Q Y N H R V K K L N E I S K L
G I S G D I D L T S A S Y N M I L E H H H H H H

- nanoluciferase
- *linker domains*
- *α-coil domain*
- galectin-3

FIG. 47

Min= 3124 Max= 61740

Min= 3366 Max= 64638

Min= 840 Max= 16075

Min= 103 Max= 1962

NanoLuc-Gal3

T = 0

T = 1 day

NanoLuc-Gal3

T = 3 day

T = 5 day

NL NL-G3 NL-TT-G3

0 d 1 d 7 d 14 d

Peptide amino acid sequences

CC1: (SEQ ID NO: 20)

M-A-R-M-K-Q-L-K-K-K-F-E-E-L-K-S-K-A-Q-Q-L-K-K-K-A-A-Q-L-K-K-K-V-G

CC2: (SEQ ID NO: 21)

M-A-R-M-K-Q-L-E-K-K-A-E-E-L-E-S-K-F-Q-Q-L-E-K-K-A-A-Q-L-E-K-K-V-G

CC3: (SEQ ID NO: 22)

M-A-R-M-K-Q-L-E-K-E-A-E-E-L-E-S-E-A-Q-Q-L-E-K-E-F-A-Q-L-E-K-E-V-G (SEQ ID NO: 20 )CC1: M-A-R M-K-Q-L-K-K-K F-E-E-L-K-S-K A-Q-Q-L-K-K-K A-A-Q-L-K-K-K V-G (SEQ ID NO: 21) CC2: M-A-R M-K-Q-L-E-K-K A-E-E-L-E-S-K F-Q-Q-L-E-K-K A-A-Q-L-E-K-K V-G (SEQ ID NO: 22) CC3: M-A-R M-K-Q-L-E-K-E A-E-E-L-E-S-E A-Q-Q-L-E-K-E F-A-Q-L-E-K-E V-G

HEPTAD: a-b-c-d-e-f-g or h-x-x-h-c-x-c of hydrophobic (h) and charged (c) residues

CC1-GFP (SEQ ID NO: 23)

MARMKQLKKKFEELKSKAQQLKKKAAQLKKKVGGSGGGSGGSGGG
GSGGSGEFSKGEELFTGVVPILVELDGDVNGHKFSVRGEGEGDATIGK
LTLKFICTTGKLPVPWPTLVTTLTYGVQCFSRYPDHMKRHDFFKSAMP
EGYVQERTISFKDDGKYKTRAVVKFEGDTLVNRIELKGTDFKEDGNILG
HKLEYNFNSHNVYITADKQKNGIKANFTVRHNVEDGSVQLADHYQQ
NTPIGDGPVLLPDNHYLSTQTVLSKDPNEKRDHMVLHEYVNAAGITL
GMDELYKLEHHHHHH

FIG. 87A

CC2-GFP (SEQ ID NO: 24)

MARMKQLEKKAEELESKFQQLEKKAAQLEKKVGGGGSGGGSGGG
SGGGSMSKGEELFTGVVPILVELDGDVNGHKFSVRGEGEGDATNG
KLTLKFICTTGKLPVPWPTLVTTLTYGVQCFSRYPDHMKRHDFFKSA
MPEGYVQERTISFKDDGTYKTRAEVKFEGDTLVNRIELKGIDFKEDG
NILGHKLEYNFNSHNVYITADKQKNGIKANFKIRHNVEDGSVQLAD
HYQQNTPIGDGPVLLPDNHYLSTQSVLSKDPNEKRDHMVLLEFVTA
AGITHGMDELYKMEQKLISEEDLNLEHHHHHH

FIG. 87B

CC3-GFP (SEQ ID NO: 25)

MARMKQLEKEAEELESEAQQLEKEFAQLEKEVGGSGGGSGGSGGG
GSGGSGEFSKGEELFTGVVPILVELDGDVNGHKFSVRGEGEGDATIG
KLTLKFICTTGKLPVPWPTLVTTLTYGVQCFSRYPDHMKRHDFFKSA
MPEGYVQERTISFKDDGKYKTRAVVKFEGDTLVNRIELKGTDFKEDG
NILGHKLEYNFNSHNVYITADKQKNGIKANFTVRHNVEDGSVQLAD
HYQQNTPIGDGPVLLPDNHYLSTQTVLSKDPNEKRDHMVLHEYVN
AAGITLGMDELYKLEHHHHHH

FIG. 87C

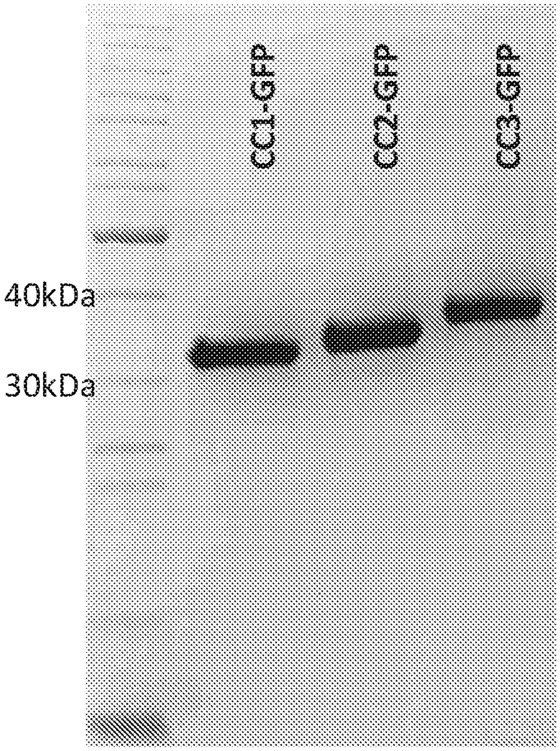

FIG. 88

TARGETED EFFECTOR PROTEINS AND USES THEREOF

CROSS-REFERENCE TO RELATED APPLICATIONS

This application is the 35 U.S.C. § 371 national stage application of PCT Application No. PCT/US2017/055076, filed Oct. 4, 2017, where the PCT claims priority to, and the benefit of, U.S. provisional application entitled "TARGETED EFFECTOR PROTEINS AND USES THEREOF" having Ser. No. 62/403,872, filed Oct. 4, 2016, and U.S. provisional application entitled "TARGETED EFFECTOR PROTEINS AND USES THEREOF" having Ser. No. 62/478,880, filed Mar. 30, 2017, all of which are herein incorporated by reference in their entireties.

STATEMENT REGARDING FEDERALLY SPONSORED RESEARCH OR DEVELOPMENT

This invention was made with government support under grant numbers EB019684 and DE027301 awarded by the National Institutes of Health. The government has certain rights in the invention.

SEQUENCE LISTING

This application contains a sequence listing filed in electronic form as an ASCII.txt file 222109-2770.txt, created on Oct. 3, 2017. The content of the sequence listing is incorporated herein in its entirety.

BACKGROUND

Targeted drug delivery can be beneficial to reduce toxicity, reduce effective dosages, and provide for improved therapeutic treatment of diseases. As such, there exists a need for improved targeted drug delivery compositions and techniques.

SUMMARY

Described herein are targeted effector fusion proteins that can include an effector protein; and a targeting moiety, wherein the targeting moiety can be operatively linked to the effector protein via a linker. The linker can be a flexible linker or a rigid linker. The flexible linker can be selected from the group consisting of: a peptide, a polypeptide, a cross-linking reagent, and a coupling agent. The targeting moiety can be capable of specifically binding to a carbohydrate. The effector protein can be an enzyme. The enzyme can be indoleamine 2,3 dioxygenase. The effector protein can be a peptide. The targeting moiety can be a galectin protein. The targeting moiety can be galectin-3. The linker can be an alpha coil polypeptide or a random coil polypeptide. The alpha coil polypeptide can have one or more heptads, where each heptad has the general formula of A-B-C-D-E-F-G, wherein amino acids A and D can each be a hydrophobic amino acid, wherein amino acids B, C, E, F, and G, are each independently selected from a hydrophilic amino acid, a polar amino acid, or a charged amino acid. The alpha coil polypeptide can have a polypeptide sequence that is about 90 to 100% identical to any one of SEQ ID NOs: SEQ ID NO: 2-16. The alpha coil polypeptide can be capable of multimerizing with one or more other alpha coils that are integrated in one or more other targeted effector proteins. The targeting moiety can be capable of specifically binding to a carbohydrate. The targeting moiety can be a carbohydrate binding protein. The effector protein can be an enzyme. The enzyme can be indoleamine 2,3 dioxygenase. The targeting moiety can be a galectin protein. The targeting moiety can be galectin-3.

Also describe herein are multimeric targeted effector fusion protein complexes that can contain at least two targeted effector fusion proteins described herein and the at least two targeted effector proteins can be conjugated to each other by binding between an alpha coil polypeptide or random coil polypeptide) in each of the at least two targeted effector proteins. The multimeric targeted effector fusion protein complex can be homogeneous. The multimeric targeted effector fusion protein complex can be heterogeneous.

Also described herein are single fusion polypeptide sequences that include an effector protein; and a targeting moiety, wherein the targeting moiety can be operatively linked to the effector protein via a linker.

Also described herein are single fusion polypeptide sequences containing at least two targeted effector fusion proteins as described herein, wherein each of the at least two targeted effector fusion proteins can be directly fused at the C-terminus, N-terminus, or both the C-terminus and N-terminus of at least one other targeted effector fusion protein of the at least two targeted effector fusion proteins.

Also described herein are single fusion polypeptide sequences containing at least two targeted effector fusion proteins as in any one of claims 9-17, wherein each of the at least two targeted effector fusion proteins can be operatively linked at the C-terminus, N-terminus, or both the C-terminus and N-terminus to at least one other targeted effector fusion protein of the at least two targeted effector fusion proteins via one or more additional amino acids.

Also described herein are DNA sequences encoding the fusion polypeptides described herein. Also described herein are plasmids containing the DNA sequence(s) encoding the fusion polypeptides described herein.

Also described herein are pharmaceutical formulations containing a targeted effector fusion protein as described herein and a pharmaceutically acceptable carrier.

Also described herein are pharmaceutical formulations containing a multimeric targeted effector fusion protein complex as described herein and a pharmaceutically acceptable carrier.

Also described herein are methods that include the step of administering a targeted effector fusion protein as described herein or a targeted effector fusion protein complex as described herein to a subject. The subject can have a disease. The subject can have inflammation, an inflammatory disease, an autoimmune disease or periodontal disease.

BRIEF DESCRIPTION OF THE DRAWINGS

Further aspects of the present disclosure will be readily appreciated upon review of the detailed description of its various embodiments, described below, when taken in conjunction with the accompanying drawings.

FIGS. 3A-3D show microscopic images that can demonstrate the effect of Indoleamine 2,3 Dioxygenase (IDO) on dendritic cells (DCs) challenged with lipopolysaccharide (LPS).

FIG. 4 shows a graph that can demonstrate the expression of CD80 in DCs treated with IDO and challenged with LPS.

FIG. 37 demonstrates RQ of IL-12p35 expression. FIG. 38 demonstrates RQ of IL-12p40. FIG. 39 demonstrates RQ of IL-1b. FIG. 40 demonstrates RQ of IFNg. FIG. 41 demonstrates RQ of TNFa. FIG. 42 demonstrates RQ of IL-6.

FIG. 43 demonstrates RQ in IL-12p35. FIG. 44 demonstrates RQ in IL-2p40. FIG. 45 demonstrates RQ in IL-1b.

FIGS. 46-51 can demonstrate the design and characterization of nanoluciferase-galectin3 fusion proteins that self-assemble into multivalent structures. (FIG. 46) General design of a fusion protein of nanoluciferase (NL) and galectin-3 (G3) connected by a "self-assembling linker domain" that mediates association of fusion proteins into a structure having 3 copies of G3 and NL (referred to herein as a "homotrimeric structure"). These fusion protein assemblies are expressed and recovered from microbial hosts in the assembled state and retain the 'functional activity' of the G3 and NL domains. (FIG. 47) A monomer of NL-TT-G3 is comprised of 496 residues and estimated to have a mass of 52.7 kDa. At the N-terminus, nanoluciferase (blue) is linked by serine and glycine residues (black) to the "TriggerTrimer" (TT) sequence (green), also denoted as an alpha-helix domain. Galectin-3 (orange) is fused via a second linker to the C-terminus of TT. Furthermore, a his-tag domain (red) was incorporated at the C-terminus to allow for purification by immobilized metal-affinity chromatography (IMAC). (FIG. 48) The molecular weight of this fusion protein was verified with matrix-assisted laser desorption/ionization-time of flight (MALDI-TOF). (FIG. 49) Gel filtration chromatography reveals the molecular weight of the homotrimer NL-TT-G3 (solid line) near that of protein standard 2, gamma globulin, among the five protein standards (dashed line). Molecular weights of protein standards: 1, thyroglobulin—670 kDa; 2, gamma globulin—158 kDa; 3, ovalbumin—44 kDa; 4, myoglobin—17 kDa, 5; vitamin B12—1.35 kDa. From this elution profile, the molecular weight of NL-TT-G3 is calculated to be approximately 175 kDa. SDS-PAGE reveals a band near 50 kDa, denoted by (*), for NL-TT-G3 collected from gel filtration. (FIG. 50) Nanoluciferase remains active after purification of NL-TT-G3 via IMAC and gel filtration. (FIG. 51) NL-TT-G3 has carbohydrate-binding activity, as shown by its interaction with β-galactosides (e.g. α- and β-lactose) immobilized on affinity chromatography resin. NL-TT-G3 eluted from the affinity chromatography resin at a soluble β-lactose concentration of 11.5 mM, whereas wild-type G3 and NL-G3 ("monomeric fusion", no TT assembly domain) eluted at soluble β-lactose concentrations of 7.7 and 7.8 mM, respectively, demonstrating that NL-TT-G3 has higher carbohydrate-binding affinity than wild-type G3 and NL-G3 (green dashed line, soluble β-lactose gradient).

FIG. 62A can demonstrate anti-GFP total IgG generated by C57BL/6 mice after injection of the model trimeric fusion TT-Green Fluorescent Protein (TT-GFP) in 1×PBS (red) or emulsified in TiterMax adjuvant (blue). FIG. 62B can demonstrate anti-NL-TT-Gal3 and anti-NL total IgG generated by C57BL/6 mice after injection of protein in 1×PBS. "Pre-Injection" denotes serum samples from naïve mice collected prior to injection, "post-injection" denotes serum samples from mice on day 35, after injections on days 0 and 28.

FIGS. 64A-641 show in vivo images of bioluminescence in the hock over time after local injection of NL, NL-G3, or NL-TT-G3.

FIG. 70). * $p<0.05$ as indicated, A $p<0.05$ IDO-Gal3-P v. IDO-Gal3T, $+p<0.05$ IDO-Gal-3-U v. uninfected.

FIGS. 87A-87C shows the amino acid sequences of the CC fusion proteins, with respective theoretical isoelectric point and molecular weight. The C-terminus of CC1, CC2, or CC3 is linked by serine and glycine residues to the green fluorescent protein variant, sfGFP, at its N-terminus. Histidine was incorporated at the C-terminus of fused protein to allow for purification by immobilized metal-affinity chromatography (IMAC).

FIG. 88 shows an SDS-PAGE analysis of CC fusion proteins appearing relatively close to their theoretical molecular weights.

DETAILED DESCRIPTION

Figure 1:
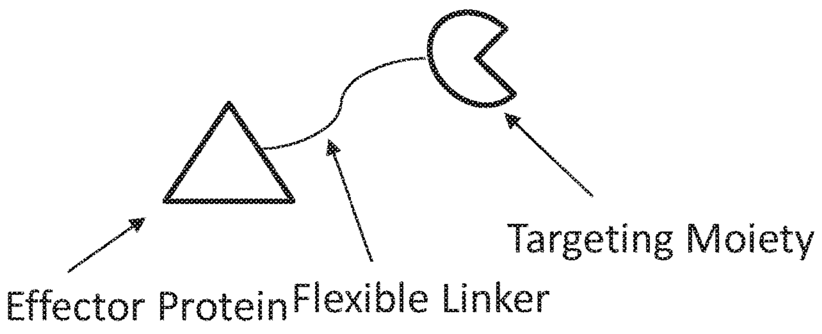
FIG. 1 shows one embodiment of a targeted effector protein as provided herein.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, biochemistry, botany and the like, which are within the skill of the art. Such techniques are explained fully in the literature.

Definitions

As used herein, "about," "approximately," and the like, when used in connection with a numerical variable, generally refers to the value of the variable and to all values of the variable that are within the experimental error (e.g., within the 95% confidence interval for the mean) or within +/−10% of the indicated value, whichever is greater.

As used herein, "active agent" or "active ingredient" refers to a substance, compound, or molecule, which is biologically active or otherwise, induces a biological or physiological effect on a subject to which it is administered to. In other words, "active agent" or "active ingredient" refers to a component or components of a composition to which the whole or part of the effect of the composition is attributed.

As used herein, "additive effect" refers to an effect arising between two or more molecules, compounds, substances, factors, or compositions that is equal to or the same as the sum of their individual effects.

The term "amphiphilic", as used herein, refers to a molecule combining hydrophilic and lipophilic (hydrophobic) properties.

As used herein, "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. Each light chain is comprised of a light chain variable region and a light chain constant region. The VH and VL regions retain the binding specificity to the antigen and can be further subdivided into regions of hypervariability, termed complementarity determining regions (CDR). The CDRs are interspersed with regions that are more conserved, termed framework regions (FR). Each VH and VL is composed of three CDRs and four framework regions, arranged from amino-terminus to carboxy-terminus in the following order: FR1, CDR1, FR2, CDR2, FR3, CDR3, and FR4. The variable regions of the heavy and light chains contain a binding domain that interacts with an antigen.

As used herein, "anti-infective" refers to compounds or molecules that can either kill an infectious agent or inhibit it from spreading. Anti-infectives include, but are not limited to, antibiotics, antibacterials, antifungals, antivirals, and antiprotozoans.

As used herein, "aptamer" refers to single-stranded DNA or RNA molecules that can bind to pre-selected targets including proteins with high affinity and specificity. Their specificity and characteristics are not directly determined by their primary sequence, but instead by their tertiary structure.

The term "biocompatible", as used herein, refers to a material that along with any metabolites or degradation products thereof that are generally non-toxic to the recipient and do not cause any significant adverse effects to the recipient. Generally speaking, biocompatible materials are materials which do not elicit a significant inflammatory or immune response when administered to a patient.

As used herein "biodegradable" generally refers to a material that will degrade or erode under physiologic conditions to smaller units or chemical species that are capable of being metabolized, eliminated, or excreted by the subject. The degradation time is a function of composition and morphology. Degradation times can be from hours to weeks.

The term "hydrophilic", as used herein, refers to substances that have strongly polar groups that readily interact with water.

As used herein, "cDNA" refers to a DNA sequence that is complementary to a RNA transcript in a cell. It is a man-made molecule. Typically, cDNA is made in vitro by an enzyme called reverse-transcriptase using RNA transcripts as templates.

As used herein, "cell," "cell line," and "cell culture" include progeny. It is also understood that all progeny may not be precisely identical in DNA content, due to deliberate or inadvertent mutations. Variant progeny that have the same function or biological property, as screened for in the originally transformed cell, are included.

As used herein, "composition" refers to a combination of active agent and at least one other compound or molecule, inert (for example, a detectable agent or label) or active, such as an adjuvant.

As used herein, "concentrated" refers to a molecule, including but not limited to a polynucleotide, peptide, polypeptide, protein, antibody, or fragments thereof, that is distinguishable from its naturally occurring counterpart in that the concentration or number of molecules per volume is greater than that of its naturally occurring counterpart.

As used herein, "control" is an alternative subject or sample used in an experiment for comparison purpose and included to minimize or distinguish the effect of variables other than an independent variable.

As used herein, "chemotherapeutic agent" or "chemotherapeutic" refer to a therapeutic agent utilized to prevent or treat cancer.

As used herein, "culturing" refers to maintaining cells under conditions in which they can proliferate and avoid senescence as a group of cells. "Culturing" can also include conditions in which the cells also or alternatively differentiate.

As used herein, "deoxyribonucleic acid (DNA)" and "ribonucleic acid (RNA)" generally refer to any polyribonucleotide or polydeoxribonucleotide, which may be unmodified RNA or DNA or modified RNA or DNA. RNA may be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), or ribozymes.

As used herein, "DNA molecule" includes nucleic acids/polynucleotides that are made of DNA.

As used herein, "derivative" refers to any compound having the same or a similar core structure to the compound but having at least one structural difference, including substituting, deleting, and/or adding one or more atoms or functional groups. The term "derivative" does not mean that the derivative is synthesized from the parent compound either as a starting material or intermediate, although this may be the case. The term "derivative" can include prodrugs, or metabolites of the parent compound. Derivatives include compounds in which free amino groups in the parent compound have been derivatized to form amine hydrochlorides, p-toluene sulfoamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form methyl and ethyl esters, or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imine, thiones, sulfones, tertiary amides, and sulfides. "Derivatives" also includes extensions of the replacement of the cyclopentane ring with saturated or unsaturated cyclohexane or other more complex, e.g., nitrogen-containing rings, and extensions of these rings with side various groups.

As used herein, "differentiate" or "differentiation," refers to the process by which precursor or progenitor cells (e.g., neuronal progenitor cells) differentiate into specific cell types (e.g., neurons).

As used herein, "differentially expressed," refers to the differential production of RNA, including but not limited to mRNA, tRNA, miRNA, siRNA, snRNA, and piRNA transcribed from a gene or regulatory region of a genome or the protein product encoded by a gene as compared to the level of production of RNA by the same gene or regulator region in a normal or a control cell. In another context, "differentially expressed," also refers to nucleotide sequences or proteins in a cell or tissue which have different temporal and/or spatial expression profiles as compared to a normal or control cell.

As used herein, "diluted" refers to a molecule, including but not limited to a polynucleotide, peptide, polypeptide, protein, antibody, or fragments thereof, that is distinguishable from its naturally occurring counterpart in that the concentration or number of molecules per volume is less than that of its naturally occurring counterpart.

As used herein, "dose," "unit dose," or "dosage" refers to physically discrete units suitable for use in a subject, each unit containing a predetermined quantity of the targeted effector fusion protein, a composition containing the targeted effector fusion protein, and/or a pharmaceutical formulation thereof calculated to produce the desired response or responses in association with its administration.

As used herein, "effective amount" is an amount sufficient to effect beneficial or desired biological, emotional, medical, or clinical response of a cell, tissue, system, animal, or human.

An effective amount can be administered in one or more administrations, applications, or dosages. The term also includes within its scope amounts effective to enhance normal physiological function.

As used herein, "expansion" or "expanded" in the context of cell refers to an increase in the number of a characteristic cell type, or cell types, from an initial population of cells, which may or may not be identical. The initial cells used for expansion need not be the same as the cells generated from expansion. For instance, the expanded cells may be produced by ex vivo or in vitro growth and differentiation of the initial population of cells.

As used herein, "expression" refers to the process by which polynucleotides are transcribed into RNA transcripts. In the context of mRNA and other translated RNA species, "expression" also refers to the process or processes by which the transcribed RNA is subsequently translated into peptides, polypeptides, or proteins.

As used herein, "fusion protein" refers to a protein formed from the combination of at least two different proteins or protein fragments. A fusion protein can be encoded by a recombinant DNA molecule. As such, a "targeted effector fusion protein" refers to a recombinant protein having an effector polypeptide or variant thereof operatively linked to a targeting moiety polypeptide and optionally other polypeptide sequences.

As used herein, "gene" refers to a hereditary unit corresponding to a sequence of DNA that occupies a specific location on a chromosome and that contains the genetic instruction for a characteristic(s) or trait(s) in an organism.

As used herein, "green fluorescent protein," "yellow fluorescent protein," "red fluorescent protein" and the like and their abbreviations include, without limitation, all forms of such proteins as they are routinely modified, derivatized, and generally known to those of ordinary skill in the art. For example, "green fluorescent protein" includes, without limitation, enhanced green fluorescent protein (eGFP), redox sensitive GFP (roGFP), superfolder GFP (sfGFP), and all color mutants.

The term "hydrophobic", as used herein, refers to substances that lack an affinity for water; tending to repel and not absorb water as well as not dissolve in or mix with water.

As used herein, "identity," is a relationship between two or more polypeptide or polynucleotide sequences, as determined by comparing the sequences. In the art, "identity" also refers to the degree of sequence relatedness between polypeptide as determined by the match between strings of such sequences. "Identity" can be readily calculated by known methods, including, but not limited to, those described in Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J. Applied Math. 1988, 48: 1073. Preferred methods to determine identity are designed to give the largest match between the sequences tested. Methods to determine identity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 1970, 48: 443-453,) algorithm (e.g., NBLAST, and XBLAST). The default parameters are used to determine the identity for the polypeptides of the present disclosure.

As used herein, "immunomodulator," refers to an agent, such as a therapeutic agent, which is capable of modulating or regulating one or more immune function or response.

As used herein "induces," "inducing," or "induced" refers to activating or stimulating a process or pathway within a cell, such as endocytosis, secretion, and exocytosis.

As used herein, "isolated" means separated from constituents, cellular and otherwise, in which the polynucleotide, peptide, polypeptide, protein, antibody, or fragments thereof, are normally associated with in nature. A non-naturally occurring polynucleotide, peptide, polypeptide, protein, antibody, or fragments thereof, do not require "isolation" to distinguish it from its naturally occurring counterpart.

The term "lipophilic", as used herein, refers to compounds having an affinity for lipids.

As used herein, "mammal," for the purposes of treatments, refers to any animal classified as a mammal, including human, domestic and farm animals, nonhuman primates, and zoo, sports, or pet animals, such as, but not limited to, dogs, horses, cats, and cows.

As used herein, "matrix" refers to a material, in which one or more specialized structures, molecules, or compositions, are embedded.

The term "molecular weight", as used herein, generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

As used herein, "multimerizing" can refer to the binding of two or more fusion proteins described herein to each other via binding between the coils (e.g. alpha helix colis and/or random polypeptide coil)/In this context, the binding can be non-covalent and/or covalent binding between the two or more fusion proteins.

As used herein, "negative control" refers to a "control" that is designed to produce no effect or result, provided that all reagents are functioning properly and that the experiment is properly conducted. Other terms that are interchangeable with "negative control" include "sham," "placebo," and "mock."

As used herein, "nucleic acid" and "polynucleotide" generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein. "Polynucleotide" and "nucleic acids" also includes PNAs (peptide nucleic acids), phosphorothioates, and other variants of the phosphate backbone of native nucleic acids. Natural nucleic acids have a phosphate backbone, artificial nucleic acids may contain other types of backbones, but contain the same bases. Thus, DNAs or RNAs with backbones modified for stability or for other reasons are "nucleic acids" or "polynucleotide" as that term is intended herein.

As used herein, "nucleic acid sequence" and "oligonucleotide" also encompasses a nucleic acid and polynucleotide as defined above.

As used herein, "organism", "host", and "subject" refers to any living entity comprised of at least one cell. A living organism can be as simple as, for example, a single isolated eukaryotic cell or cultured cell or cell line, or as complex as a mammal, including a human being, and animals (e.g., vertebrates, amphibians, fish, mammals, e.g., cats, dogs, horses, pigs, cows, sheep, rodents, rabbits, squirrels, bears, primates (e.g., chimpanzees, gorillas, and humans). "Subject" may also be a cell, a population of cells, a tissue, an organ, or an organism, preferably to human and constituents thereof.

As used herein, "overexpressed" or "overexpression" refers to an increased expression level of an RNA or protein product encoded by a gene as compared to the level of expression of the RNA or protein product in a normal or control cell.

As used herein, "operatively linked" can indicate that the regulatory sequences useful for expression of the coding sequences of a nucleic acid are placed in the nucleic acid molecule in the appropriate positions relative to the coding sequence so as to effect expression of the coding sequence. This same definition is sometimes applied to the arrangement of coding sequences and/or transcription control elements (e.g. promoters, enhancers, and termination elements), and/or selectable markers in an expression vector. The term "operatively linked" can also refer to the arrangement of polypeptide segments within a single polypeptide chain, where the individual polypeptide segments can be, without limitation, a protein, fragments thereof, linking peptides, and/or signal peptides. The term operatively linked can refer to direct fusion of different individual polypeptides within the single polypeptides or fragments thereof where there are no intervening amino acids between the different segments as well as when the individual polypeptides are connected to one another via one or more intervening amino acids.

As used herein, "patient" refers to an organism, host, or subject in need of treatment.

As used herein "peptide" refers to chains of at least 2 amino acids that are short, relative to a protein or polypeptide.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "pharmaceutically acceptable salt" refers to any acid or base addition salt whose counter-ions are non-toxic to the subject to which they are administered in pharmaceutical doses of the salts.

As used herein, "plasmid" as used herein refers to a non-chromosomal double-stranded DNA sequence including an intact "replicon" such that the plasmid is replicated in a host cell.

As used herein, "positive control" refers to a "control" that is designed to produce the desired result, provided that all reagents are functioning properly and that the experiment is properly conducted.

As used herein, "preventative" and "prevent" refers to hindering or stopping a disease or condition before it occurs, even if undiagnosed, or while the disease or condition is still in the sub-clinical phase.

As used herein, "protein" as used herein refers to a large molecule composed of one or more chains of amino acids in a specific order. The term protein is used interchangeable with "polypeptide." The order is determined by the base sequence of nucleotides in the gene coding for the protein. Proteins are required for the structure, function, and regulation of the body's cells, tissues, and organs. Each protein has a unique function. The term protein as used herein can also include peptides. Thus, for example, an "effector protein" can include both effector proteins and effector peptides.

As used herein, "purified" or "purify" is used in reference to a nucleic acid sequence, peptide, or polypeptide that has increased purity relative to the natural environment.

As used herein, the term "recombinant" generally refers to a non-naturally occurring nucleic acid, nucleic acid construct, or polypeptide. Such non-naturally occurring nucleic acids may include natural nucleic acids that have been modified, for example that have deletions, substitutions, inversions, insertions, etc., and/or combinations of nucleic acid sequences of different origin that are joined using molecular biology technologies (e.g., a nucleic acid sequences encoding a fusion protein (e.g., a protein or polypeptide formed from the combination of two different proteins or protein fragments), the combination of a nucleic acid encoding a polypeptide to a promoter sequence, where the coding sequence and promoter sequence are from different sources or otherwise do not typically occur together naturally (e.g., a nucleic acid and a constitutive promoter), etc.). Recombinant also refers to the polypeptide encoded by the recombinant nucleic acid. Non-naturally occurring nucleic acids or polypeptides include nucleic acids and polypeptides modified by man.

As used herein, "separated" refers to the state of being physically divided from the original source or population such that the separated compound, agent, particle, or molecule can no longer be considered part of the original source or population.

As used herein, "specifically binds" or "specific binding" refers to binding that occurs between such paired species such as enzyme/substrate, receptor/agonist or antagonist, antibody/antigen, lectin/carbohydrate, oligo DNA primers/DNA, enzyme or protein/DNA, and/or RNA molecule to other nucleic acid (DNA or RNA) or amino acid, which may be mediated by covalent or non-covalent interactions or a combination of covalent and non-covalent interactions. When the interaction of the two species produces a non-covalently bound complex, the binding that occurs is typically electrostatic, hydrogen-bonding, or the result of lipophilic interactions. Accordingly, "specific binding" occurs between a paired species where there is interaction between the two which produces a bound complex having the characteristics of an antibody/antigen, enzyme/substrate, DNA/DNA, DNA/RNA, DNA/protein, RNA/protein, RNA/amino acid, receptor/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins.

As used herein, "specific binding partner" or "binding partner" is a compound or molecule to which a second compound or molecule binds with a higher affinity than all other molecules or compounds.

As used interchangeably herein, "subject," "individual," or "patient" refers to a vertebrate organism.

As used herein, "substantially pure" means an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

As used herein, "substantially pure cell population" refers to a population of cells having a specified cell marker characteristic and differentiation potential that is about 50%, preferably about 75-80%, more preferably about 85-90%, and most preferably about 95% of the cells making up the total cell population. Thus, a "substantially pure cell population" refers to a population of cells that contain fewer than about 50%, preferably fewer than about 20-25%, more preferably fewer than about 10-15%, and most preferably fewer than about 5% of cells that do not display a specified marker characteristic and differentiation potential under designated assay conditions.

The terms "sufficient" and "effective", as used interchangeably herein, refer to an amount (e.g. mass, volume, dosage, concentration, and/or time period) needed to achieve one or more desired result(s). For example, a therapeutically effective amount refers to an amount needed to achieve one or more therapeutic effects.

As used herein, "synergistic effect," "synergism," or "synergy" refers to an effect arising between two or more molecules, compounds, substances, factors, or compositions that is greater than or different from the sum of their individual effects.

As used herein, "therapeutic" refers to treating, healing, and/or ameliorating a disease, disorder, condition, or side effect, or to decreasing in the rate of advancement of a disease, disorder, condition, or side effect. The term also includes within its scope enhancing normal physiological function, palliative treatment, and partial remediation of a disease, disorder, condition, side effect, or symptom thereof. The disease or disorder can be acute inflammation, chronic inflammation, autoimmunity, fibrosis, pathogen infection, metabolic dysfunction, Crohn's disease, colitis (ulcerative colitis), irritable bowel syndrome, diverticulitis, psoriasis, dermatitis, arthritis (osteoarthritis, rheumatoid arthritis, psoriatic arthritis), hepatitis, nephritis, asthma, lysosomal storage disorders, pancreatic insufficiency, cancer, and metastasis. The therapeutic can also be used to initiate, promote, accelerate, or enhance wound healing, tissue growth, and tissue regeneration.

As used herein, "therapeutically effective amount" refers to the amount of a targeted effector fusion protein, a pharmaceutical formulation thereof, auxiliary agent, or secondary agent described herein that will elicit the biological or medical response of a tissue, system, animal, or human that is being sought by the researcher, veterinarian, medical doctor or other clinician. "Therapeutically effective amount" includes that amount of a targeted effector fusion protein, a composition containing a targeted effector fusion protein, a pharmaceutical formulation thereof that, when administered alone or co-administered with a secondary agent, is sufficient to prevent development of, reduce or alleviate to some extent, one or more of the symptoms of inflammation. "Therapeutically effect amount" includes that amount of targeted effector fusion protein, a composition containing a targeted effector fusion protein, a pharmaceutical formulation thereof that, when administered alone or co-administered with a secondary agent, is sufficient to reduce or alleviate to some extent, one or more of the symptoms of inflammation.

The terms "treating" and "treatment" as used herein refer generally to obtaining a desired pharmacological and/or physiological effect. The effect may be prophylactic in terms of preventing or partially preventing a disease, symptom or condition thereof, such as acute inflammation, chronic inflammation, autoimmunity, fibrosis, pathogen infection, metabolic dysfunction, Crohn's disease, colitis (ulcerative colitis), irritable bowel syndrome, diverticulitis, psoriasis, dermatitis, arthritis (osteoarthritis, rheumatoid arthritis, psoriatic arthritis), hepatitis, nephritis, asthma, lysosomal storage disorders, pancreatic insufficiency, cancer, and metastasis, wound healing, tissue growth, and tissue regeneration, and/or may be therapeutic in terms of a partial or complete cure of a disease, condition, symptom or adverse effect attributed to the disease, disorder, or condition. The term "treatment" as used herein covers any treatment of immunological or other disorders acute inflammation, chronic inflammation, autoimmunity, fibrosis, pathogen infection, metabolic dysfunction, Crohn's disease, colitis (ulcerative colitis), irritable bowel syndrome, diverticulitis, psoriasis, dermatitis, arthritis (osteoarthritis, rheumatoid arthritis, psoriatic arthritis), hepatitis, nephritis, asthma, lysosomal storage disorders, pancreatic insufficiency, cancer, and metastasis, wound healing, tissue growth, and tissue regeneration in a mammal, particularly a human, and includes: (a) preventing the disease from occurring in a subject which may be predisposed to the disease but has not yet been diagnosed as having it; (b) inhibiting the disease, i.e., arresting its development; or (c) relieving the disease, i.e., mitigating or ameliorating the disease and/or its symptoms or conditions.

As used herein, "tangible medium of expression" refers to a medium that is physically tangible and is not a mere abstract thought or an unrecorded spoken word. Tangible medium of expression includes, but is not limited to, words on a cellulosic or plastic material or data stored on a suitable device such as a flash memory or CD-ROM.

As used herein, "transduced" refers to the direct introduction of a protein into a cell.

As used herein, the term "transfection" refers to the introduction of an exogenous and/or recombinant nucleic acid sequence into the interior of a membrane enclosed space of a living cell, including introduction of the nucleic acid sequence into the cytosol of a cell as well as the interior space of a mitochondria, nucleus, or chloroplast. The nucleic acid may be in the form of naked DNA or RNA, it may be associated with various proteins or regulatory elements (e.g., a promoter and/or signal element), or the nucleic acid may be incorporated into a vector or a chromosome. It may be incorporated into a viral particle.

As used herein, "transformation" or "transformed" refers to the introduction of a nucleic acid (e.g., DNA or RNA) into cells in such a way as to allow expression of the coding portions of the introduced nucleic acid.

As used herein, "underexpressed" or "underexpression" refers to decreased expression level of an RNA or protein product encoded by a gene as compared to the level of expression of the RNA or protein product in a normal or control cell.

As used herein, "variant" refers to a polypeptide that differs from a reference polypeptide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally. "Variant" includes functional and structural variants.

As used herein, the term "vector" or is used in reference to a vehicle used to introduce an exogenous nucleic acid sequence into a cell. A vector may include a DNA molecule, linear or circular (e.g. plasmids), which includes a segment encoding a polypeptide of interest operatively linked to additional segments that provide for its transcription and translation upon introduction into a host cell or host cell organelles. Such additional segments may include promoter and terminator sequences, and may also include one or more origins of replication, one or more selectable markers, an enhancer, a polyadenylation signal, etc. Expression vectors are generally derived from yeast or bacterial genomic or plasmid DNA, or viral DNA, or may contain elements of both.

As used herein, "wild-type" is the typical form of an organism, variety, strain, gene, protein, or characteristic as it occurs in nature, as distinguished from mutant forms that may result from selective breeding or transformation with a transgene.

As used herein, "encoding" can refer to the basic biological concept that DNA can be transcribed into RNA, which then can be translated into a polypeptide.

Unless otherwise defined herein, all technical and scientific terms used herein have the same meaning as commonly understood by one of ordinary skill in the art.

DISCUSSION

Described herein are targeted effector fusion proteins that can include an effector protein that can be capable of causing a biological effect in a target cell, tissue, and/or organ and a targeting moiety that can be capable of directing the targeted effector fusion protein specifically to a desired cell, tissue, and/or organ (also referred to herein as a target cell, tissue or organ), where the effector protein is operatively linked to the targeting moiety via a flexible linker or an alpha coil. In some embodiments, the targeted effector fusion proteins can self-assemble into multimers (also referred to herein as targeted effector fusion protein complexes). Also described herein are compositions and formulations of the targeted effector fusion proteins and complexes. The targeted effector fusion proteins, complexes thereof, compositions thereof, and formulations thereof described herein can be administered to a subject in need thereof. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Targeted Effector Fusion Proteins and Complexes Thereof

Disclosed herein are recombinant cDNA sequences, which code for various targeted effector fusion proteins containing an effector protein and a targeting moiety, where the effector protein is operatively coupled to the targeting moiety. The effector protein included in the targeted effector fusion protein can be, without limitation, an enzyme, growth factor, cytokine, chemokine, extra-cellular matrix protein or fragment thereof, transmembrane receptor or fragment thereof, transport protein, antibody or fragments thereof, or hormone. The effector protein can be indoleamine 2,3 dioxygenase (IDO). The effector protein can be a reporter protein, such as luciferase or a fluorescent protein.

The targeting moiety can be any polypeptide or other molecule that can specifically bind a target cell, tissue, and/or organ. The targeting moiety, in some embodiments, can specifically bind a carbohydrate. The carbohydrate can be beta-galactosides, including n-acetyllactosamine, repeated variants of n-acetyllactosamine, fucosylated variants of n-acetyllactosamine, sialyated variants of n-acetyllactosamine, alpha-lactose, beta-lactose, LacdiNAc, galactomannans, β-galactopyrenose, and Thomsen-Friedenreich glycoantigen (TFAg). The targeting moiety can be a galectin protein. In some embodiments, the targeting moiety can be a galectin-3 protein.

As shown in FIG. 1, in some embodiments, the effector protein can be operatively linked to the targeting moiety via a linker. The linker can be a flexible linker, a rigid linker, or a random coil polypeptide. The flexible linker can be a peptide or polypeptide flexible linker, a cross-linking reagent, and/or coupling agent, including, but not limited to, disulfide bonds, azide linkages, avidin-biotin linkages, ester linkages, thioester linkages, or thioether linkages. In some embodiments, the linker can vary from about 1 to 100 amino acids or more. The linker can be any variation or combination (natural or synthetic) of any naturally or synthetically occurring amino acids. The flexible linker can be operatively linked to the C-terminus, N-terminus or both the C-terminus and the N-terminus of the effector protein and/or the targeting moiety.

In some embodiments, the effector protein can be fused directly (e.g. "a zero-length" fusion) to the targeting moiety. In other words, in some embodiments, there is no linker between the effector protein and targeting moiety.

Figure 2A:
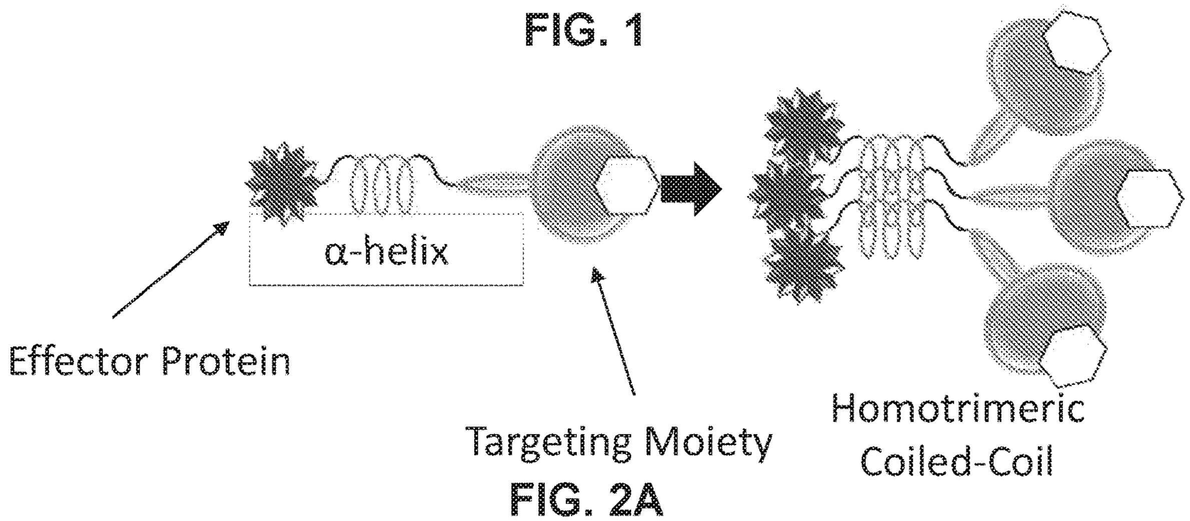
FIGS. 2A-2B show various embodiments of a targeted effector protein complex as provided herein.
Figure 2B:
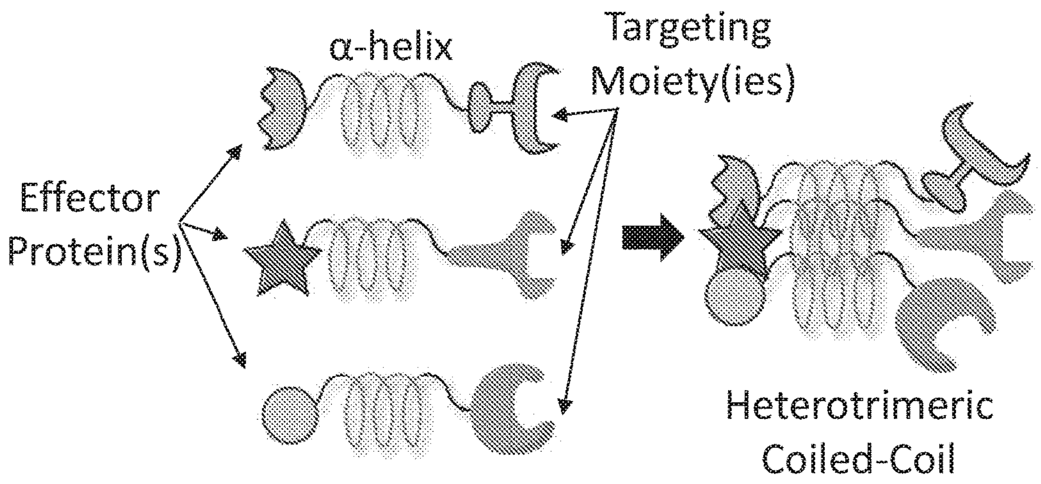

As shown in FIGS. 2A-2B, in some embodiments, the effector protein can be operatively linked to the targeting moiety via domain folds into an alpha-helix. The alpha-helix domain can be operatively linked to the C-terminus, N-terminus or both the C-terminus and the N-terminus of the effector protein and/or the targeting moiety. The alpha-helical coil can have the general structure of one or more 7-amino acid heptads repeats, which can each be denoted by the formula A-B-C-D-E-F-G, where each letter represents an amino acid in the heptad. In some embodiments, A and D can each be a hydrophobic amino acid, and each amino acid B, C, E, F, and G can each be independently selected from a hydrophilic amino acid, a polar amino acid, or a charged amino acid. Hydrophobic amino acids can include glycine, alanine, valine, leucine, isoleucine, proline, phenylalanine, methionine, and tryptophan. Polar amino acids can include serine, threonine, asparagine, glutamine, histidine, and tyrosine. Charged amino acids can include arginine, aspartate, glutamate, and lysine. Hydrophilic amino acids can include arginine, lysine, asparagine, histidine, glutamate. The number of heptad repeats can be 1 (i.e. 1 heptad), 2, 3, 4, 5, 6, 7, 8, 9, 10, or more.

In some embodiments, the targeted effector fusion protein having an alpha-helical coiled-coil domain can have a polypeptide sequence that is about 90-100% identical to SEQ ID NO: 1. As shown in FIGS. 2A-2B, in some embodiments where the linker can be an alpha-helix, the targeted effector protein can form a multimer with one or more other targeted effector proteins provided herein also having the exact same, or otherwise complementary (e.g.

charge and/or hydrophobicity, hydrogen bond donor/acceptor, Van der Waals forces) alpha-helix domain. The multimer (also referred to herein as complexes) can be formed via interactions between the alpha-helix domains included in the targeted effector fusion proteins thereby forming multimeric alpha-helix coiled-coils. The alpha-helix coiled-coils can facilitate self-assembly of a multimeric targeted effector fusion protein. The multimeric targeted effector fusion protein complex can be a dimer, trimer, tetramer, pentamer, hexamer or heptamer. The multimeric targeted effector fusion protein complex can be homogenous or heterogeneous. In this context the term "homogeneous" can refer to a multimer where each monomer targeted effector protein is the same. In this context, the term "heterogeneous" can refer to a multimer where at least two of the monomer targeted effector proteins are different from each other. The alpha helix polypeptide of the targeted effector protein can have can have a polypeptide sequence that is about 90 to 100% identical to any one of SEQ ID NOs: SEQ ID NO: 2-16.

One of skill in the art will be able to, identify, determine, and generate cDNA and DNA sequences encoding any polypeptide provided herein based on algorithms, computer programs, and general knowledge and techniques used in the art.

The targeted effector fusion proteins and thus complexes thereof can contain one or more protein tags operatively coupled to the targeted effector fusion protein. These types of tags can be amino acid sequences that allow for affinity purification, solubilization, chromatographical separation, and/or immunodetection of the fusion protein. Suitable protein tags include, but are not limited to, chitin binding protein (CBP), maltose binding protein (MBP), glutathione-S-transferase (GST), poly(His), thioredoxin (TRX), poly (NANP), FLAG-tag (including any FLAG-tag variant, e.g. 3×FLAG), V5-tag, Myc-tag, HA-tag, S-tag, SBP-Tag, Sftag 1, Softag 3, Tc tag, Xpress tag, Strep-tag, Isopeptag, Spy Tag, Ty tag, Biotin Carboxyl Carrier Protein (BCCP), and Nus tag. Other tags will be appreciated by those of skill in the art and are within the scope of this disclosure.

The targeted effector fusion protein and thus a complex thereof can contain one or more reporter proteins, which can be the effector protein or in addition to the effector protein, operatively coupled to the effector protein and/or targeting moiety. Suitable reporter genes include, but are not limited to, fluorescent proteins (e.g. green fluorescent protein (GFP), red fluorescent protein (RFP), yellow fluorescent protein (YFP), blue fluorescent protein (BFP), and cyan fluorescent protein (CFP)), beta-galactosidase, luciferase (bacterial, firefly, and *Renilla* luciferase), antibiotic-resistance genes (e.g. chloramphenicol acetyltransferase, neomycin phosphotransferase, and NPT-II), p-glucuronidase, and alkaline phosphatase. Inclusion of a reporter protein allows, inter alia, for direct and/or indirect characterization of the fusion protein and function of the fusion protein, as well as affinity purification of the protein. The reporter protein can be operatively linked to the N-terminus and/or the C-terminus of the effector protein and/or the targeting moiety or other portion of the targeted effector fusion protein.

Recombinant Vectors

The targeted effector fusion protein cDNA sequence can be incorporated into a suitable expression vector. The expression vector can contain one or more regulatory sequences or one or more other sequences used to facilitate the expression of the targeted effector fusion protein cDNA. The expression vector can contain one or more regulatory sequences or one or more other sequences used to facilitate the replication of the targeted effector fusion protein expression vector. The expression vector can be suitable for expressing the targeted effector fusion protein in a bacterial cell. In other embodiments, the expression vector can be suitable for expressing the targeted effector fusion protein in a yeast cell. In further embodiments, the expression vector can be suitable for expressing the targeted effector fusion protein in a plant cell. In other embodiments, the expression vector can be suitable for expressing the targeted effector fusion protein in a mammalian cell. In another embodiment, the vector can be suitable for expressing the targeted effector fusion protein in a fungal cell. In further embodiments, the vector can be suitable for expressing the targeted effector fusion protein in an insect cell. Suitable expression vectors are generally known to those of ordinary skill in the art.

Targeted Effector Fusion Protein Production

The targeted effector fusion proteins described herein can be produced in a suitable in vitro expression system such as bacterial production system, yeast system, insect system, or mammalian cell system. Such systems can include growing a population of bacterial, yeast, or mammalian cells that express one or more vectors that include a DNA encoding one or more targeted effector fusion proteins described herein. The cells can produce the targeted effector fusion proteins and, in some embodiments secrete the produced protein into the cell media. After the targeted effector protein has been produced the targeted effector fusion protein can be harvested from the cell culture media and/or by lysing the cells to release produced protein contained within the cells.

Compositions and Formulations Containing a Targeted Effector Fusion Protein and/or Complex Thereof.

Also within the scope of this disclosure are compositions and formulations containing a targeted effector fusion protein or complex thereof as described herein. The targeted effector fusion protein or complex thereof described herein can be provided to a subject in need thereof alone or as an active ingredient, such as in a pharmaceutical formulation. As such, also described herein are pharmaceutical formulations containing an amount of a targeted effector fusion protein or complex thereof. In some embodiments, the pharmaceutical formulations contain a therapeutically effective amount of a targeted effector fusion protein or complex thereof. The pharmaceutical formulations described herein can be administered to a subject in need thereof. The subject in need thereof can have an enzymatic deficiency, periodontal disease, and/or autoimmune disease, inflammation, inflammatory disease and/or a symptom thereof. In other embodiments, the targeted effector fusion protein and/or complex thereof can be used in the manufacture of a medicament for the treatment or prevention of an enzyme deficiency, periodontal disease, an autoimmune disease, inflammation, inflammatory disease and/or a symptom thereof.

Pharmaceutically Acceptable Carriers and Auxiliary Ingredients and Agents

The pharmaceutical formulations containing a therapeutically effective amount of a targeted effector fusion protein or complex thereof described herein can further include a pharmaceutically acceptable carrier. Suitable pharmaceutically acceptable carriers include, but are not limited to, water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active composition.

In addition to the therapeutically effective amount of a targeted effector fusion protein and/or complex thereof described herein, the pharmaceutical formulation can also include an effective amount of an auxiliary active agent, including but not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics.

Suitable hormones include, but are not limited to, amino-acid derived hormones (e.g. melatonin and thyroxine), small peptide hormones and protein hormones (e.g. thyrotropin-releasing hormone, vasopressin, insulin, growth hormone, luteinizing hormone, follicle-stimulating hormone, and thyroid-stimulating hormone), eicosanoids (e.g. arachidonic acid, lipoxins, and prostaglandins), and steroid hormones (e.g. estradiol, testosterone, tetrahydro testosteron cortisol).

Suitable immunomodulators include, but are not limited to, prednisone, azathioprine, 6-MP, cyclosporine, tacrolimus, methotrexate, interleukins (e.g. IL-2, IL-7, and IL-12), cytokines (e.g. interferons (e.g. IFN-α, IFN-β, IFN-ε, IFN-κ, IFN-ω, and IFN-γ), granulocyte colony-stimulating factor, and imiquimod), chemokines (e.g. CCL3, CCL26 and CXCL7), cytosine phosphate-guanosine, oligodeoxynucleotides, glucans, antibodies, and aptamers).

Suitable antipyretics include, but are not limited to, non-steroidal anti-inflammants (e.g. ibuprofen, naproxen, ketoprofen, and nimesulide), aspirin and related salicylates (e.g. choline salicylate, magnesium salicylae, and sodium salicaylate), paracetamol/acetaminophen, metamizole, nabumetone, phenazone, and quinine.

Suitable anxiolytics include, but are not limited to, benzodiazepines (e.g. alprazolam, bromazepam, chlordiazepoxide, clonazepam, clorazepate, diazepam, flurazepam, lorazepam, oxazepam, temazepam, triazolam, and tofisopam), serotenergic antidepressants (e.g. selective serotonin reuptake inhibitors, tricyclic antidepresents, and monoamine oxidase inhibitors), mebicar, afobazole, selank, bromantane, emoxypine, azapirones, barbiturates, hydroxyzine, pregabalin, validol, and beta blockers.

Suitable antipsychotics include, but are not limited to, benperidol, bromoperidol, droperidol, haloperidol, moperone, pipaperone, timiperone, fluspirilene, penfluridol, pimozide, acepromazine, chlorpromazine, cyamemazine, dizyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, chlorprothixene, clopenthixol, flupentixol, tiotixene, zuclopenthixol, clotiapine, loxapine, prothipendyl, carpipramine, clocapramine, molindone, mosapramine, sulpiride, veralipride, amisulpride, amoxapine, aripiprazole, asenapine, clozapine, blonanserin, iloperidone, lurasidone, melperone, nemonapride, olanzaprine, paliperidone, perospirone, quetiapine, remoxipride, risperidone, sertindole, trimipramine, ziprasidone, zotepine, alstonie, befeprunox, bitopertin, brexpiprazole, cannabidiol, cariprazine, pimavanserin, pomaglumetad methionil, vabicaserin, xanomeline, and zicronapine.

Suitable analgesics include, but are not limited to, paracetamol/acetaminophen, non-steroidal anti-inflammants (e.g. ibuprofen, naproxen, ketoprofen, and nimesulide), COX-2 inhibitors (e.g. rofecoxib, celecoxib, and etoricoxib), opioids (e.g. morphine, codeine, oxycodone, hydrocodone, dihydromorphine, pethidine, buprenorphine), tramadol, norepinephrine, flupiretine, nefopam, orphenadrine, pregabalin, gabapentin, cyclobenzaprine, scopolamine, methadone, ketobemidone, piritramide, and aspirin and related salicylates (e.g. choline salicylate, magnesium salicylate, and sodium salicylate).

Suitable antispasmodics include, but are not limited to, mebeverine, papverine, cyclobenzaprine, carisoprodol, orphenadrine, tizanidine, metaxalone, methodcarbamol, chlorzoxazone, baclofen, dantrolene, baclofen, tizanidine, and dantrolene.

Suitable anti-inflammatories include, but are not limited to, prednisone, non-steroidal anti-inflammants (e.g. ibuprofen, naproxen, ketoprofen, and nimesulide), COX-2 inhibitors (e.g. rofecoxib, celecoxib, and etoricoxib), and immune selective anti-inflammatory derivatives (e.g. submandibular gland peptide-T and its derivatives).

Suitable anti-histamines include, but are not limited to, H1-receptor antagonists (e.g. acrivastine, azelastine, bilastine, brompheniramine, buclizine, bromodiphenhydramine, carbinoxamine, cetirizine, chlorpromazine, cyclizine, chlorpheniramine, clemastine, cyproheptadine, desloratadine, dexbromapheniramine, dexchlorpheniramine, dimenhydrinate, dimetindene, diphenhydramine, doxylamine, ebasine, embramine, fexofenadine, hydroxyzine, levocetirzine, loratadine, meclozine, mirtazapine, olopatadine, orphenadrine, phenindamine, pheniramine, phenyltoloxamine, promethazine, pyrilamine, quetiapine, rupatadine, tripelennamine, and triprolidine), H2-receptor antagonists (e.g. cimetidine, famotidine, lafutidine, nizatidine, rafitidine, and roxatidine), tritoqualine, catechin, cromoglicate, nedocromil, and β2-adrenergic agonists.

Suitable anti-infectives include, but are not limited to, amebicides (e.g. nitazoxanide, paromomycin, metronidazole, tinidazole, chloroquine, miltefosine, amphotericin b, and iodoquinol), aminoglycosides (e.g. paromomycin, tobramycin, gentamicin, amikacin, kanamycin, and neomycin), anthelmintics (e.g. pyrantel, mebendazole, ivermectin, praziquantel, abendazole, thiabendazole, oxamniquine), antifungals (e.g. azole antifungals (e.g. itraconazole, fluconazole, posaconazole, ketoconazole, clotrimazole, miconazole, and voriconazole), echinocandins (e.g. caspofungin, anidulafungin, and micafungin), griseofulvin, terbinafine, flucytosine, and polyenes (e.g. nystatin, and amphotericin b), antimalarial agents (e.g. pyrimethamine/sulfadoxine, artemether/lumefantrine, atovaquone/proquanil, quinine, hydroxychloroquine, mefloquine, chloroquine, doxycycline, pyrimethamine, and halofantrine), antituberculosis agents (e.g. aminosalicylates (e.g. aminosalicylic acid), isoniazid/rifampin, isoniazid/pyrazinamide/rifampin, bedaquiline, isoniazid, ethambutol, rifampin, rifabutin, rifapentine, capreomycin, and cycloserine), antivirals (e.g. amantadine, rimantadine, abacavir/lamivudine, emtricitabine/tenofovir, cobicistat/elvitegravir/emtricitabine/tenofovir, efavirenz/emtricitabine/tenofovir, avacavir/lamivudine/zidovudine, lamivudine/zidovudine, emtricitabine/tenofovir, emtricitabine/opinavir/ritonavir/tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpivirine, delaviridine, nevirapine, entecavir, lamivudine, adefovir, sofosbuvir, didanosine, tenofovir, avacivr, zidovudine, stavudine, emtricitabine, xalcitabine, telbivudine, simeprevir, boceprevir, telaprevir, lopinavir/ritonavir, fosamprenvir, dranuavir, ritonavir, tipranavir, atazanavir, nelfinavir, amprenavir, indinavir, sawuinavir, ribavirin, valcyclovir, acyclovir, famciclovir, ganciclovir, and valganciclovir), carbapenems (e.g. doripenem, meropenem, ertapenem, and cilastatin/imipenem), cephalosporins (e.g. cefadroxil, cephradine, cefazolin, cephalexin, cefepime, ceflaroline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, cefizoxime, and ceftazidime), glycopeptide antibiotics (e.g. vancomycin, dalbavancin, oritavancin, and telvancin), glycylcyclines (e.g. tigecycline), leprostatics (e.g. clofazimine and thalidomide), lincomycin and derivatives thereof (e.g. clindamycin and lincomycin), macrolides and derivatives thereof (e.g. telithromycin, fidaxomicin, erthromycin, azithromycin, clarithromycin, dirithromycin, and troleandomycin), linezolid, sulfamethoxazole/trimethoprim, rifaximin, chloramphenicol, fosfomycin, metronidazole, aztreonam, bacitracin, penicillins (amoxicillin, ampicillin, bacampicillin, carbenicillin, piperacillin, ticarcillin, amoxicillin/clavulanate, ampicillin/sulbactam, piperacillin/tazobactam, clavulanate/ticarcillin, penicillin, procaine penicillin, oxaxillin, dicloxacillin, and nafcillin), quinolones (e.g. lomefloxacin, norfloxacin, ofloxacin, qatifloxacin, moxifloxacin, ciprofloxacin, levofloxacin, gemifloxacin, moxifloxacin, cinoxacin, nalidixic acid, enoxacin, grepafloxacin, gatifloxacin, trovafloxacin, and sparfloxacin), sulfonamides (e.g. sulfamethoxazole/trimethoprim, sulfasalazine, and sulfasoxazole), tetracyclines (e.g. doxycycline, demeclocycline, minocycline, doxycycline/salicyclic acid, doxycycline/omega-3 polyunsaturated fatty acids, and tetracycline), and urinary anti-infectives (e.g. nitrofurantoin, methenamine, fosfomycin, cinoxacin, nalidixic acid, trimethoprim, and methylene blue).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, cytoxan, cyclophosphamide, decitabine, dexamethasone, docetaxel, hydroxyurea, decarbazine, leuprolide, epirubicin, oxaliplatin, asparaginase, estramustine, cetuximab, vismodegib, asparginase *Erwinia chrysanthemi*, amifostine, etoposide, flutamide, toremifene, fulvestrant, letrozole, degarelix, pralatrexate, methotrexate, floxuridine, obinutuzumab, gemcitabine, afatinib, imatinib mesylatem, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, ado-trastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octretide, dasatinib, regorafenib, histrelin, sunitinib, siltuximab, omacetaxine, thioguanine (tioguanine), dabrafenib, erlotinib, bexarotene, temozolomide, thiotepa, thalidomide, BCG, temsirolimus, bendamustine hydrochloride, triptorelin, aresnic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, and all-trans retinoic acid Effective Amounts of the Targeted Effector Fusion Protein and/or Complex Thereof and Auxiliary Agents The pharmaceutical formulations can contain a therapeutically effective amount of a targeted effector fusion protein or complex thereof. In some embodiments the pharmaceutical formulations can also include a therapeutically effective amount of an auxiliary agent. In some embodiments, the therapeutically effective amount of the targeted effector fusion protein and/or complex thereof can range from about 1 μg/kg to about 10 mg/kg. In further embodiments, the therapeutically effective amount of the targeted effector fusion protein and/or complex thereof can range from 1 ng/g bodyweight to about 0.1 mg/g bodyweight. The therapeutically effective amount of the targeted effector fusion protein and/or complex thereof can range from about 1 μg to about 10 g. In some embodiments, the therapeutically effective amount of the targeted effector fusion protein and/or complex thereof or pharmaceutical composition containing the targeted effector fusion protein and/or complex thereof can range from about 10 nL to about 10 mL. In some embodiments, the therapeutically effective amount of the targeted effector fusion protein and/or complex thereof or pharmaceutical composition is from about 10 nL to about 1 μL. For some embodiments, the therapeutically effective amount can be from about 1 ng to about 50 ng per injection, if administered via injection.

In some embodiments, the therapeutically effective amount can be from about 1 to about 2 micrograms per injection, such as for a systemically administered injection. In additional embodiments, the therapeutically effective amount can be about 200 to about 300 μL per injection, such as for a systemically administered injection. In some embodiments, the therapeutically effective amount can be about 5 ng/μL, such as for systemic injections. For some embodiments, the therapeutically effective amount can be about 1 to about 1.5 μg per 5 g of bodyweight. In some embodiments, the therapeutically effective amount can be from about 200 μg to about 300 μg per kg of bodyweight.

In embodiments where there is an auxiliary active agent contained in the pharmaceutical formulation in addition to the targeted effector fusion protein and/or complex thereof, the therapeutically effective amount of the auxiliary active agent will vary depending on the auxiliary active agent. In some embodiments, the effective amount of the auxiliary active agent ranges from 0.001 micrograms to about 1 milligram. In other embodiments, the effective amount of the auxiliary active agent ranges from about 0.01 IU to about 1000 IU. In further embodiments, the effective amount of the auxiliary active agent ranges from 0.001 mL to about 1 mL. In yet other embodiments, the effective amount of the auxiliary active agent ranges from about 1% w/w to about 50% w/w of the total pharmaceutical formulation. In additional embodiments, the effective amount of the auxiliary active agent ranges from about 1% v/v to about 50% v/v of the total pharmaceutical formulation. In still other embodiments, the effective amount of the auxiliary active agent ranges from about 1% w/v to about 50% w/v of the total pharmaceutical formulation.

Dosage Forms

In some embodiments, the pharmaceutical formulations described herein may be in a dosage form. The dosage forms can be adapted for administration by any appropriate route. Appropriate routes include, but are not limited to, oral (including buccal or sublingual), rectal, epidural, intracranial, intraocular, inhaled, intranasal, topical (including buccal, sublingual, or transdermal), vaginal, intraurethral, parenteral, intracranial, subcutaneous, intramuscular, intravenous, intraperitoneal, intradermal, intraosseous, intracardiac, intraarticular, intracavernous, intrathecal, intravitreal, intracerebral, gingival, subgingival, intracerebroventricular, and intradermal. Such formulations may be prepared by any method known in the art.

Dosage forms adapted for oral administration can be discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as foam, spray, or liquid solution. In some embodiments, the oral dosage form can contain about 1 ng to 1000 g of a pharmaceutical formulation containing a therapeutically effective amount or an appropriate fraction thereof of the targeted effector fusion protein and/or complex thereof or composition containing the targeted effector fusion protein and or complex thereof. The oral dosage form can be administered to a subject in need thereof.

Where appropriate, the dosage forms described herein can be microencapsulated. The dosage form can also be prepared to prolong or sustain the release of any ingredient. In some embodiments, the targeted effector fusion protein or complex thereof can be the ingredient whose release is delayed. In other embodiments, the release of an optionally included auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, PA: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, the targeted effector fusion protein or complex thereof, auxiliary active ingredient, and/or pharmaceutically acceptable salt thereof can be formulated with a paraffinic or water-miscible ointment base. In some embodiments, the active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, the targeted effector fusion protein and/or complex thereof, the composition or formulation containing a targeted effector fusion protein and/or complex thereof, auxiliary active ingredient, and/or pharmaceutically acceptable salt thereof in a dosage form adapted for inhalation is in a particle-size-reduced form that is obtained or obtainable by micronization. In some embodiments, the particle size of the size reduced (e.g. micronized) compound or salt or solvate thereof, is defined by a D50 value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active ingredient (e.g. the targeted effector proteins and/or complexes thereof, compositions thereof, and formulations thereof, and/or auxiliary active agent), which may be generated by various types of metered dose pressurized aerosols, nebulizers, or insufflators.

In some embodiments, the dosage forms can be aerosol formulations suitable for administration by inhalation. In some of these embodiments, the aerosol formulation can contain a solution or fine suspension of the targeted effector fusion protein and/or complex thereof, the composition or formulation containing a targeted effector fusion protein and/or complex thereof, and/or pharmaceutically acceptable salt thereof, and a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g. metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of a targeted effector fusion protein, composition containing a targeted effector fusion protein, or a pharmaceutical formulation thereof. In further embodiments, the aerosol formulation can also contain co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, or 8 times daily, in which 1, 2, or 3 doses are delivered each time.

For some dosage forms suitable and/or adapted for inhaled administration, the pharmaceutical formulation is a dry powder inhalable formulation. In addition to the targeted effector fusion protein and/or complex thereof, the composition or formulation containing a targeted effector fusion protein and/or complex thereof, an auxiliary active ingredient, and/or pharmaceutically acceptable salt thereof, such a dosage form can contain a powder base such as lactose, glucose, trehalose, manitol, and/or starch. In some of these embodiments, the targeted effector fusion protein, the composition containing a targeted effector fusion protein, auxiliary active ingredient, and/or pharmaceutically acceptable salt thereof is in a particle-size reduced form. In further embodiments, a performance modifier, such as L-leucine or another amino acid, cellobiose octaacetate, and/or metals salts of stearic acid, such as magnesium or calcium stearate.

In some embodiments, the aerosol dosage forms can be arranged so that each metered dose of aerosol contains a predetermined amount of an active ingredient, such as the one or more of the targeted effector fusion proteins and/or complexes thereof, or compositions containing a targeted effector fusion protein and/or complex thereof described herein.

Dosage forms adapted for vaginal administration can be presented as pessaries, tampons, creams, gels, pastes, foams, or spray formulations. Dosage forms adapted for rectal administration include suppositories or enemas.

Dosage forms adapted for parenteral administration and/or adapted for any type of injection (e.g. intravenous, intraperitoneal, subcutaneous, intramuscular, intradermal, intraosseous, epidural, intracardiac, intraarticular, intracavernous, gingival, subginigival, intrathecal, intravireal, intracerebral, and intracerebroventricular) can include aqueous and/or non-aqueous sterile injection solutions, which can contain anti-oxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and resuspended in a sterile carrier to reconstitute the dose prior to administration. Extemporaneous injection solutions and suspensions can be prepared in some embodiments, from sterile powders, granules, and tablets.

Dosage forms adapted for ocular administration can include aqueous and/or non-aqueous sterile solutions that can optionally be adapted for injection, and which can optionally contain anti-oxidants, buffers, bacteriostats, solutes that render the composition isotonic with the eye or fluid contained therein or around the eye of the subject, and aqueous and non-aqueous sterile suspensions, which can include suspending agents and thickening agents.

For some embodiments, the dosage form contains a predetermined amount of the targeted effector fusion protein and/or complex thereof, or formulation or composition containing a targeted effector fusion protein and/or complex thereof per unit dose. In some embodiments, the predetermined amount of the targeted effector fusion protein and or complex thereof or composition or formulation thereof is a therapeutically effective amount of the targeted effector fusion protein and/or complex thereof, composition thereof, or formulation thereof, effective to treat or prevent an enzymatic deficiency, an immune dysfunction disease, periodontal disease and/or a symptom thereof. In other embodiments, the predetermined amount of the targeted effector fusion protein and/or complex thereof, composition thereof, formulation thereof can be an appropriate fraction of the therapeutically effective amount of the active ingredient (e.g. targeted effector fusion protein and/or complex thereof, composition thereof, formulation thereof and/or auxiliary active agent). Such unit doses may therefore be administered once or more than once a day. Such pharmaceutical formulations may be prepared by any of the methods well known in the art.

Methods of Using the Targeted Effector Proteins

The targeted effector fusion protein(s) and complex(es) thereof and pharmaceutical formulations thereof described herein can be used for the treatment and/or prevention of a disease, disorder, syndrome, or a symptom thereof in a subject. In some embodiments, the targeted effector fusion protein(s) and complex(es) thereof and pharmaceutical formulations thereof described herein can be used to treat and/or prevent an enzyme deficiency, an autoimmune disease, periodontal disease, inflammation, an inflammatory disease, and/or a symptom thereof in a subject.

An amount of the targeted effector fusion protein(s) and complex(es) thereof and compositions and pharmaceutical formulations thereof described herein can be administered to a subject in need thereof one or more times per day, week, month, or year. In some embodiments, the amount administered can be the therapeutically effective amount of the targeted effector fusion protein(s) and complex(es) thereof and compositions and pharmaceutical formulations thereof. For example, the targeted effector fusion protein(s) and complex(es) thereof and compositions and pharmaceutical formulations thereof can be administered in a daily dose. This amount may be given in a single dose per day. In other embodiments, the daily dose may be administered over multiple doses per day, in which each containing a fraction of the total daily dose to be administered (sub-doses). In some embodiments, the amount of doses delivered per day is 2, 3, 4, 5, or 6. In further embodiments, the targeted effector fusion protein(s) and complex(es) thereof and compositions and pharmaceutical formulations thereof can be administered one or more times per week, such as 1, 2, 3, 4, 5, or 6 times per week. In other embodiments, the targeted effector fusion protein(s) and complex(es) thereof and compositions and pharmaceutical formulations thereof can be administered one or more times per month, such as 1 to 5 times per month. In still further embodiments, the targeted effector fusion protein(s) and complex(es) thereof and compositions and pharmaceutical formulations thereof can be administered one or more times per year, such as 1 to 11 times per year.

The targeted effector fusion protein(s) and complex(es) thereof and compositions and pharmaceutical formulations thereof can be co-administered with a secondary agent by any convenient route. The secondary agent is a separate compound and/or formulation from the targeted effector fusion protein(s) and complex(es) thereof and compositions and pharmaceutical formulations thereof. The secondary agent can be administered simultaneously with the targeted effector fusion protein(s) and complex(es) thereof and compositions and pharmaceutical formulations thereof. The secondary agent can be administered sequentially with the targeted effector fusion protein(s) and complex(es) thereof and compositions and pharmaceutical formulations thereof.

The secondary agent can have an additive or synergistic effect to the targeted effector fusion protein(s) and complex(es) thereof and compositions and pharmaceutical formulations thereof. Suitable secondary agents include, but are not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics.

In embodiments where the targeted effector fusion protein(s) and complex(es) thereof and compositions and pharmaceutical formulations thereof are simultaneously co-administered with a secondary agent, the targeted effector fusion protein(s) and complex(es) thereof and compositions and pharmaceutical formulations thereof can be administered to the subject at substantially the same time as the secondary agent. As used in this context "substantially the same time" refers to administration of targeted effector fusion protein(s) and complex(es) thereof and compositions and pharmaceutical formulations thereof and a secondary agent where the period of time between administration of the targeted effector fusion protein, composition, or pharmaceutical formulation thereof and the secondary agent is between 0 and 10 minutes.

In embodiments where the targeted effector fusion protein(s) and complex(es) thereof and compositions and pharmaceutical formulations thereof is/are sequentially co-administered with a secondary agent, the targeted effector fusion protein(s) and complex(es) thereof and compositions and pharmaceutical formulations thereof can be administered first, and followed by administration of the secondary agent after a period of time. In other embodiments where the targeted effector fusion protein(s) and complex(es) thereof and compositions and pharmaceutical formulations thereof is/are sequentially co-administered with a secondary agent, the secondary agent can be administered first, and followed by administration of the targeted effector fusion protein, composition, or pharmaceutical formulations thereof after a period of time. The period of time between administration of the targeted effector fusion protein(s) and complex(es) thereof and compositions and pharmaceutical formulations thereof and the secondary agent can range from 10 minutes to about 96 hours. In some embodiments the period of time can be about 10 minutes, about 30 minutes, about 1 hour, about 2 hours, about 4 hours, about 6 hours, about 8 hours, about 10 hours, or about 12 hours. The sequential administration can be repeated as necessary over the course of the period of treatment.

The amount of the targeted effector fusion protein(s) and complex(es) thereof and compositions and pharmaceutical formulations thereof that can be administered are described elsewhere herein. The amount of the secondary agent will vary depending on the secondary agent. The amount of the secondary agent can be a therapeutically effective amount. In some embodiments, the effective amount of the secondary agent ranges from 0.001 micrograms to about 1 milligram. In other embodiments, the amount of the secondary agent ranges from about 0.01 IU to about 1000 IU. In further embodiments, the amount of the secondary agent ranges from 0.001 mL to about 1 mL. In yet other embodiments, the amount of the secondary agent ranges from about 1% w/w to about 50% w/w of the total pharmaceutical formulation. In additional embodiments, the amount of the secondary agent ranges from about 1% v/v to about 50% v/v of the total pharmaceutical formulation. In still other embodiments, the amount of the secondary agent ranges from about 1% w/v to about 50% w/v of the total secondary agent composition or pharmaceutical formulation.

In some embodiments, the composition or formulation containing the targeted effector fusion protein(s) and/or complex(es) thereof can be administered to a patient via an injection. Suitable methods of injection include, but are not limited to. intravenous, intraperitoneal, subcutaneous, intramuscular, intradermal, intraosseous, epidural, intracardiac, intraarticular, intracavernous, intrathecal, intravitreal, intracerebral, gingival, subginigival, intranodal, and intracerebroventricular injection. Other suitable methods of administration of the composition or formulation containing the targeted effector fusion protein include, but are not limited to, topical, transdermal, nasal, or oral delivery. In some embodiments, the dosage of the targeted effector fusion protein ranges from about 0.01 μg/g bodyweight to about 10 mg/g bodyweight.

Kits Containing the Targeted Effector Fusion Protein and Formulations Thereof

The targeted effector fusion protein(s) and complex(es) thereof and compositions and pharmaceutical formulations thereof described herein can be presented as a combination kit. As used herein, the terms "combination kit" or "kit of parts" refers to the targeted effector fusion protein, compositions containing any one or more of the targeted effector fusion protein(s) and complex(es) thereof and compositions and pharmaceutical formulations thereof described herein and additional components that are used to package, sell, market, deliver, and/or administer the combination of elements or a single element, such as the active ingredient, contained therein. Such additional components include but are not limited to, packaging, syringes, blister packages, bottles, and the like. When one or more of the components (e.g. active agents) contained in the kit are administered simultaneously, the combination kit can contain the active agents in a single pharmaceutical formulation (e.g. a tablet) or in separate pharmaceutical formulations.

The combination kit can contain each agent, compound, pharmaceutical formulation or component thereof described herein, in separate compositions or pharmaceutical formulations. The separate compositions or pharmaceutical formulations can be contained in a single package or in separate packages within the kit. Also provided in some embodiments, are buffers, diluents, solubilization reagents, cell culture media and other reagents. These additional components can be contained in a single package or in separate packages within the kit.

In some embodiments, the combination kit also includes instructions printed on or otherwise contained in a tangible medium of expression. The instructions can provide information regarding the content of the targeted effector fusion protein, compositions containing the targeted effector fusion protein(s) and complex(es) thereof and compositions and pharmaceutical formulations thereof and/or other auxiliary and/or secondary agent contained therein, safety information regarding the content of the targeted effector fusion protein(s) and complex(es) thereof and compositions and pharmaceutical formulations thereof and/or other auxiliary and/or secondary agent contained therein, information regarding the dosages, indications for use, and/or recommended treatment regimen(s) for the targeted effector fusion protein(s) and complex(es) thereof and compositions and pharmaceutical formulations thereof and/or other auxiliary and/or secondary agent contained therein. In some embodiments, the instructions can provide directions for administering the targeted effector fusion protein(s) and complex(es)

thereof and compositions and pharmaceutical formulations thereof and/or other auxiliary and/or secondary agent to a subject having an enzyme deficiency, immune dysfunction disease, periodontal disease, and/or a symptom thereof.

Without further elaboration, it is believed that one skilled in the art can, based on the description herein, utilize the present disclosure to its fullest extent. It is emphasized that the embodiments of the present disclosure, particularly any "preferred" embodiments, are merely possible examples of the implementations, merely set forth for a clear understanding of the principles of the disclosure. Many variations and modifications may be made to the disclosed embodiment(s) of the disclosure without departing substantially from the spirit and principles of the disclosure. All such modifications and variations are within the scope of this disclosure.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Indoleamine 2,3-dioxygenase (IDO), an enzyme that catalyzes the rate limiting step of tryptophan catabolism into N-formyl-kynurenine, has been shown to play critical role in the promotion of tolerance. IDO is expressed in certain cells and tissues, particularly in antigen presenting cells and the placenta. There is evidence that depletion of this essential amino acid increases susceptibility of T cells to apoptosis while some of its resulting metabolites (quinolinic acid and 3-hydroxyanthranilic acid) have a direct cytotoxic effect on effector T cells resulting in reduced immune activation. In addition, IDO-expressing cells preferentially induce proliferation of regulatory T cells. This example demonstrates compositions and methods to exogenously deliver IDO in order to manipulate the ratio of tryptophan to kynurenines to direct localized metabolism in the context of inflammation, inflammatory diseases, and autoimmune diseases.

Galectin 3 (Gal3) is a chimera type member of the β-galactoside-binding soluble lectin family and is widely expressed in numerous cells. It has a strong affinity for proteins in the extracellular matrix (ECM) such as laminin, collagen, and vitronectin, as well as certain immune cell receptors including CD7, CD71, CD98, and CTLA4.

Generally, Recombinant human IDO was tested for activity, purity and endotoxin content using a spectrophotometric, SDS-PAGE, and ChromoLAL method, respectively. Murine bone-marrow derived dendritic cells (DCs) responses to extracellular IDO were evaluated by incorporating the enzyme into the media at 15 μg/mL. Expression of cell surface maturation markers (CD80/CD86/MHCII) was assessed by flow cytometry, IL-12p70 and IL-10 cytokine secretion by ELISA, and morphology changes and viability by microscopy. DCs were then pre-treated with ovalbumin 323-339 peptide (OVA) and incubated with OVA-specific CD4+ T cells, previously isolated from OT-II mice splenocytes using a magnetic negative selection process, either in the presence or absence of IDO and the enzyme inhibitor 1-methyl tryptophan (MT). Proliferation was measured using carboxyfluorescein succinimidyl ester (CFSE) dilution. Other materials and methods used are provided in greater detail herein.

Generally, the results demonstrated that IDO showed a specific activity of 400 pmoles/min/μg with over 90% purity and less than 1 EU/mL. CD80/CD86/MHCII evaluation revealed DCs remain immature in the presence of extracellular IDO and are able to resist maturation when challenged with lipopolysaccharide. Secretion of the proinflammatory cytokine IL-12p70 was significantly reduced in the presence of extracellular IDO. Additionally, IDO-treated DCs are able to suppress antigen-specific CD4+ T cell proliferation. This effect is mediated by active enzyme as demonstrated by the introduction of MT. Further, a fusion construct of Galectin 3 and NanoLuciferase does not alter the activity of either protein. Binding to laminin, collagen type 1, vitronectin, Jurkat T and dendritic cells by the fusion construct can be mediated by the carbohydrate recognition domain and was not observed to induce cell death. The Fusion construct does not act as a pathogen associated molecular pattern and is able to selectively bind primary splenocytes. Dendritic cells treated with IDO-Gal3 fusion proteins are able to maintain an immature phenotype and suppress antigen specific T cell proliferation. This suppression can be active enzyme dependent. In vivo delivery of the IDO-Gal3 fusion construct was able to modulate localized metabolism by suppressing gene expression of inflammatory cytokines and increasing kynurenines. Additional results are discussed below.

FIGS. 3A-3D show microscopic images demonstrating the effect of Indoleamine 2,3 Dioxygenase (IDO) on dendritic cells (DCs) and challenged with lipopolysaccharide (LPS).

FIG. 4 shows a graph demonstrating expression of CD80 in DCs treated with IDO and challenged with LPS.

Figure 5:
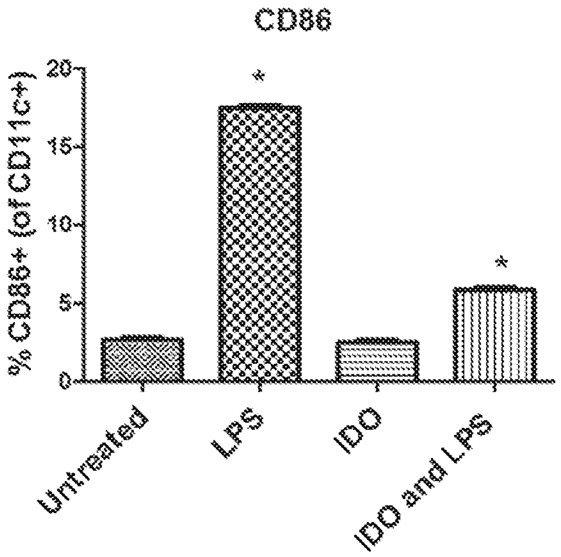
FIG. 5 shows a graph that can demonstrate the expression of CD86 in DCs treated with IDO and challenged with LPS.

FIG. 5 shows a graph demonstrating expression of CD86 in DCs treated with IDO and challenged with LPS.

Figure 6:
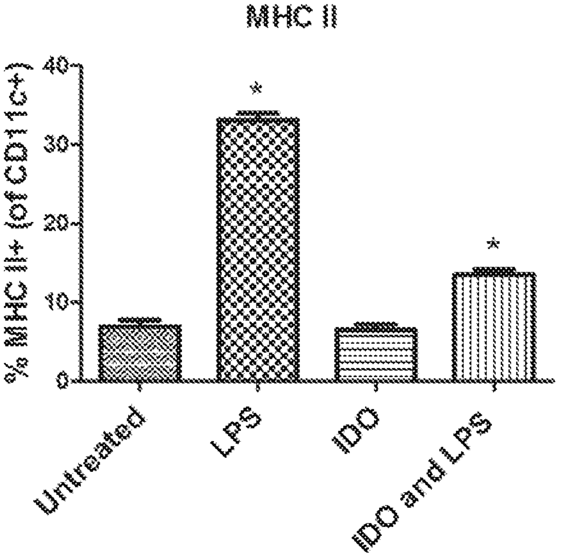
FIG. 6 shows a graph that can demonstrate the expression of MHC II in DCs treated with IDO and challenged with LPS.

FIG. 6 shows a graph demonstrating expression of MHC II in DCs treated with IDO and challenged with LPS.

Figure 7:
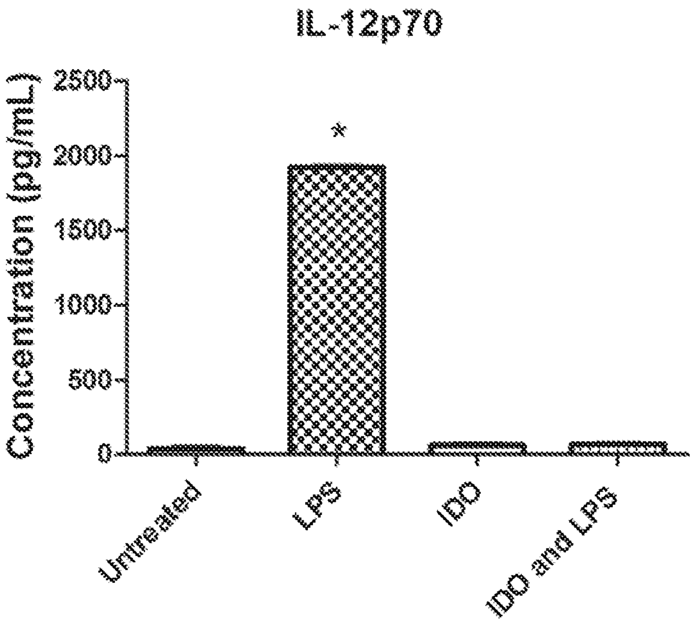
FIG. 7 shows a graph that can demonstrate the secretion of IL-12p70 in DCs treated with IDO and challenged with LPS.

FIG. 7 shows a graph demonstrating secretion of IL-12p70 in DCs treated with IDO and challenged with LPS.

Figure 8:
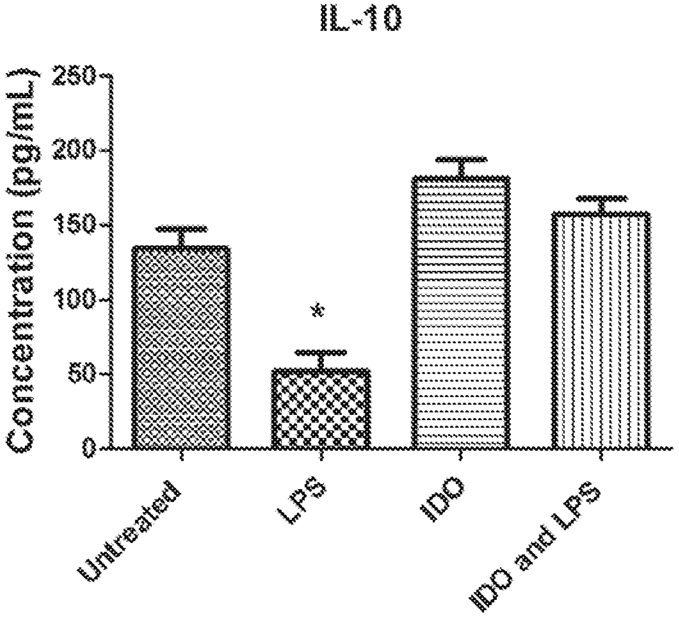
FIG. 8 shows a graph that can demonstrate the secretion of IL-10 in DCs treated with IDO and challenged with LPS.

FIG. 8 shows a graph demonstrating secretion of IL-10 in DCs treated with IDO and challenged with LPS.

Figure 9:
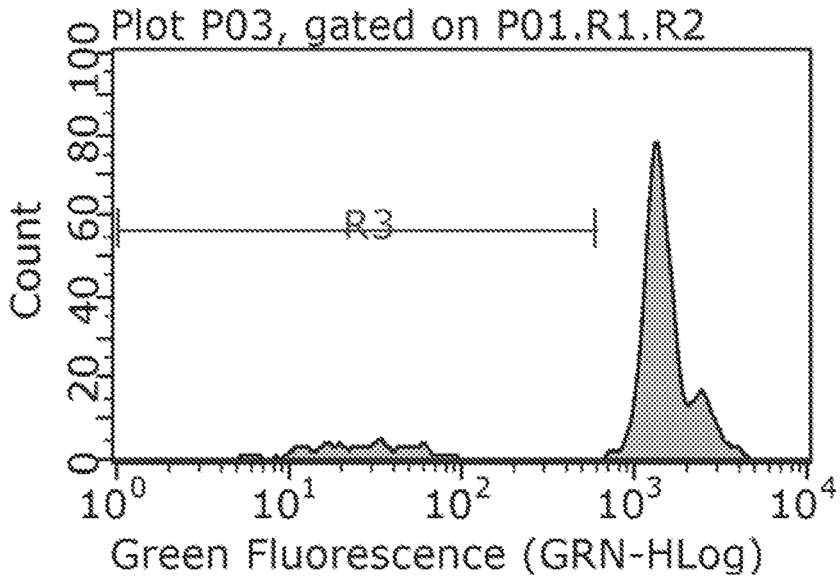
FIG. 9 shows a representative histogram that can demonstrate the proliferation profile of DCs and CFSE-labeled T cells co-cultured without antigen (negative control).

FIG. 9 representative histogram showing the proliferation profile of DCs and CFSE-labeled T cells co-cultured without antigen (negative control).

Figure 10:
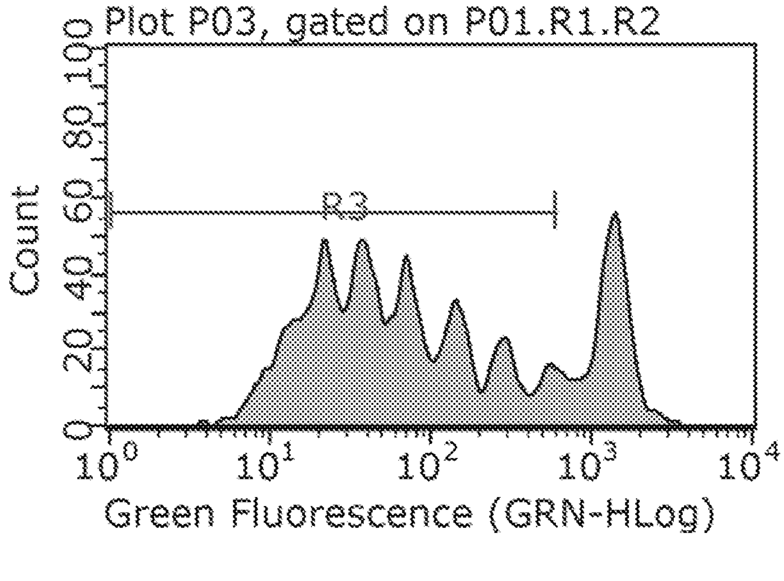
FIG. 10 shows a representative histogram that can demonstrate the proliferation profile of DCs pulsed with antigen and co-cultured with CFSE-labeled T cells (positive control).

FIG. 10 shows a representative histogram showing the proliferation profile of DCs pulsed with antigen and co-cultured with CFSE-labeled T cells (positive control).

Figure 11:
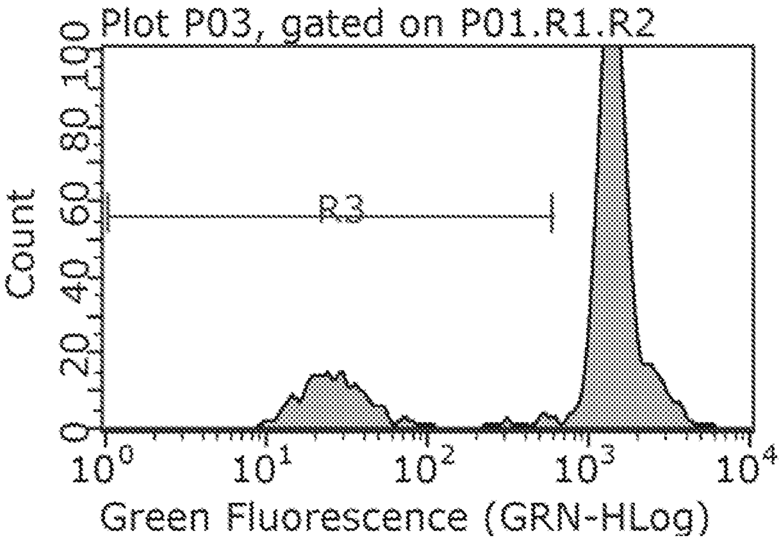
FIG. 11 shows a representative histogram that can demonstrate the proliferation profile of DCs pre-treated with IDO, pulsed with antigen and co-cultured with CFSE-labeled T cells (treatment group, shows IDO-treated DCs suppress antigen specific T cell proliferation).

FIG. 11 shows a representative histogram showing the proliferation profile of DCs pre-treated with IDO, pulsed with antigen and co-cultured with CFSE-labeled T cells (treatment group, shows IDO-treated DCs suppress antigen specific T cell proliferation).

Figure 12:
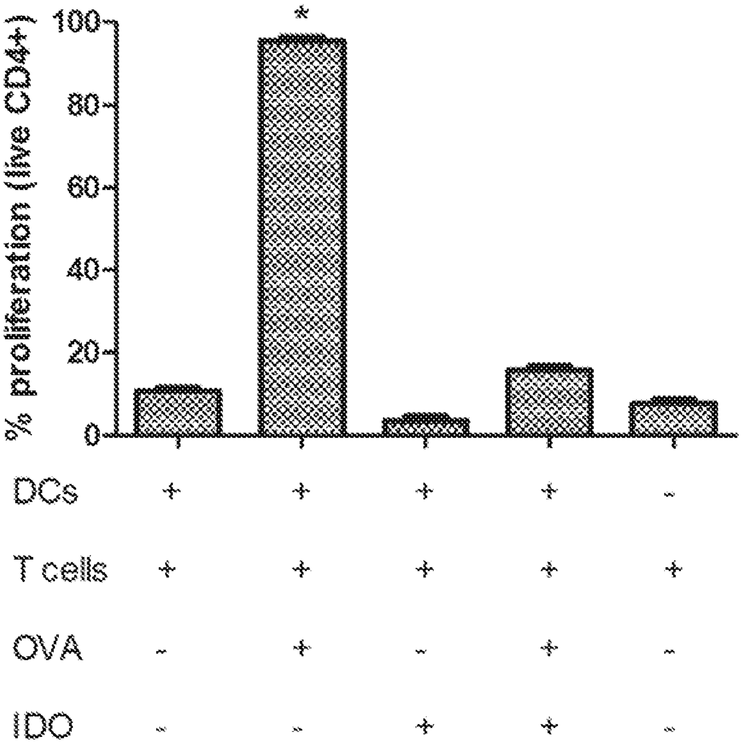
FIG. 12 shows a graph that can demonstrate proliferation of CD4 positive T cells in stimulated and unstimulated DCs pretreated with IDO.

FIG. 12 shows a graph demonstrating proliferation of CD4 positive T cells in stimulated and unstimulated DCs pretreated with IDO.

Figure 13:
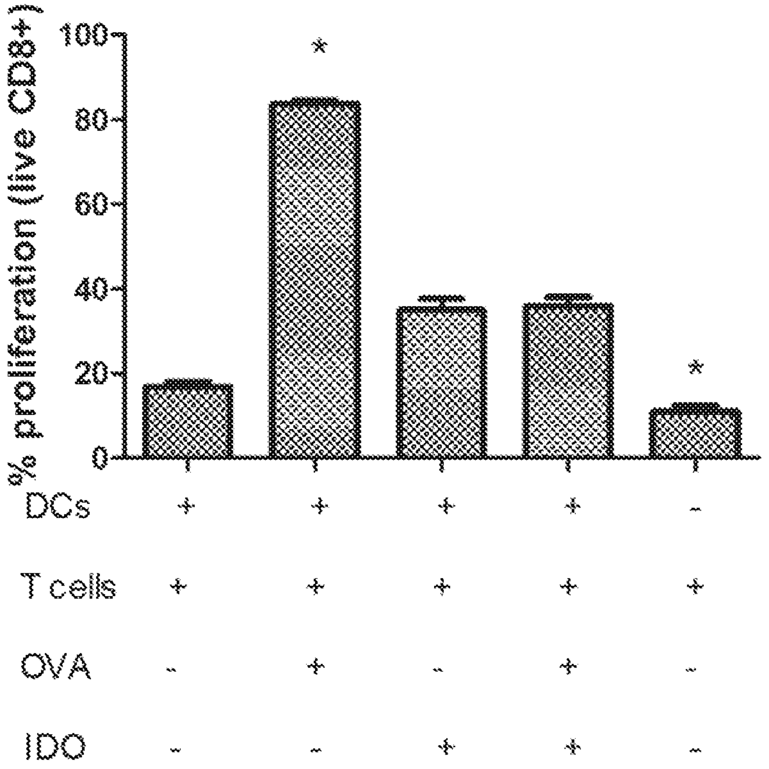
FIG. 13 shows a graph that can demonstrate proliferation of CD8 positive T cells in stimulated and unstimulated DCs pretreated with IDO.

FIG. 13 shows a graph demonstrating proliferation of CD8 positive T cells in stimulated and unstimulated DCs pretreated with IDO.

Figure 14:
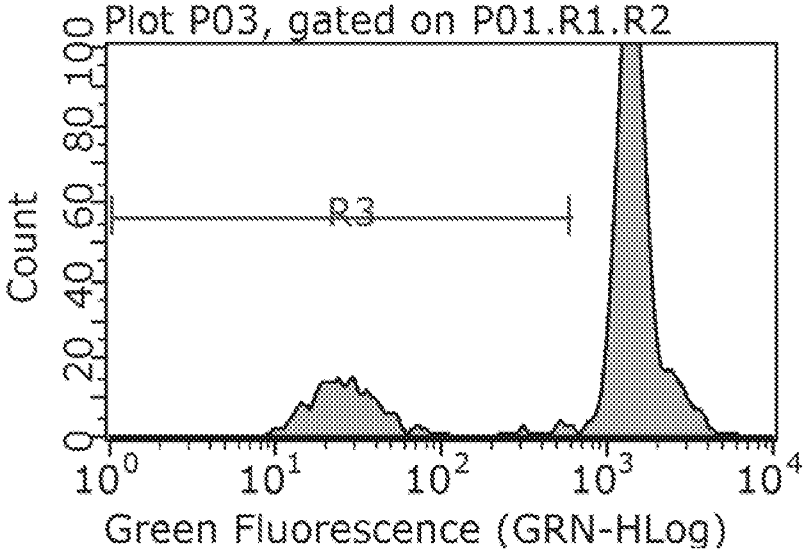
FIG. 14 shows a representative histogram that can demonstrate the proliferation profile of DCs pre-treated with IDO, pulsed with antigen and co-cultured with CFSE-labeled T cells (treatment group, shows IDO-treated DCs suppress antigen specific T cell proliferation) and is the same as FIG. 11.

FIG. 14 shows a representative histogram showing the proliferation profile of DCs pre-treated with IDO, pulsed with antigen and co-cultured with CFSE-labeled T cells (treatment group, shows IDO-treated DCs suppress antigen specific T cell proliferation) and is the same as FIG. 11.

Figure 15:
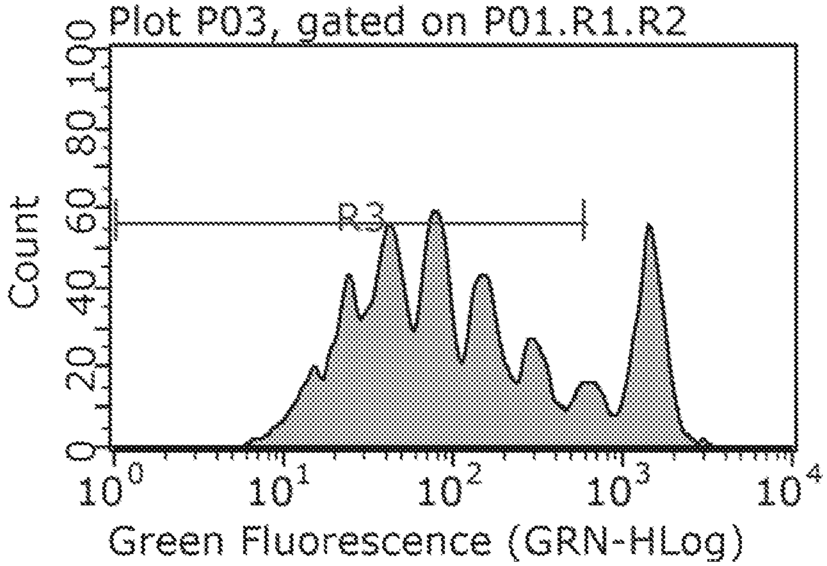
FIG. 15 shows representative histogram that can demonstrate the proliferation profile of DCs pre-treated with IDO and methyl tryptophan (MT, IDO inhibitor), pulsed with antigen and co-cultured with CFSE-labeled T cells (shows IDO-mediated suppression is active enzyme dependent).

FIG. 15 representative histogram showing the proliferation profile of DCs pre-treated with IDO and methyl tryptophan (MT, IDO inhibitor), pulsed with antigen and co-cultured with CFSE-labeled T cells (shows IDO-mediated suppression is active enzyme dependent.

Figure 16:
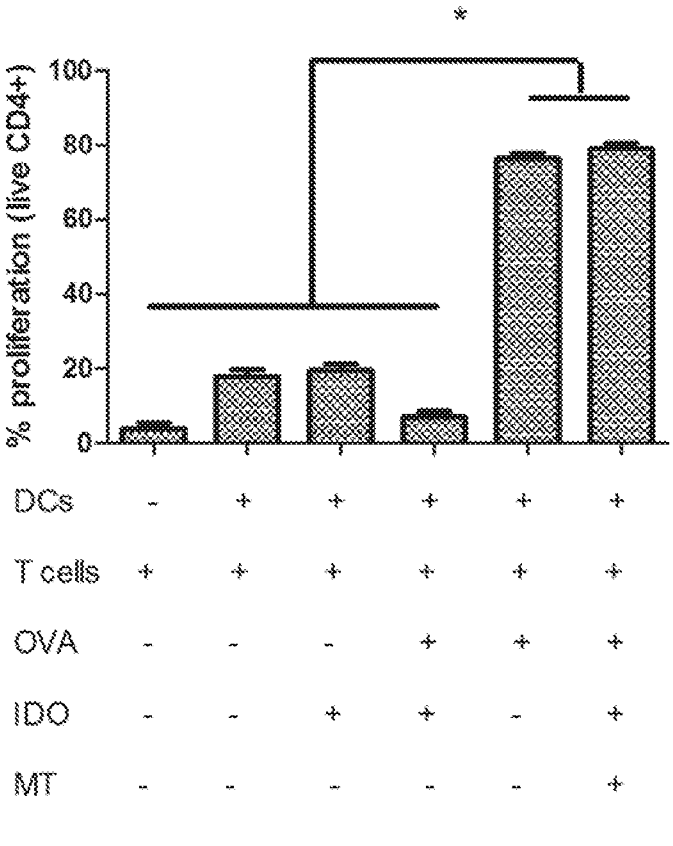
FIG. 16 shows a graph that can demonstrate proliferation of CD4 positive T cells in stimulated and unstimulated DCs pretreated with IDO in the presence and absence of MT.

FIG. 16 shows a graph demonstrating proliferation of CD4 positive T cells in stimulated and unstimulated DCs pretreated with IDO in the presence and absence of MT.

Figure 17:
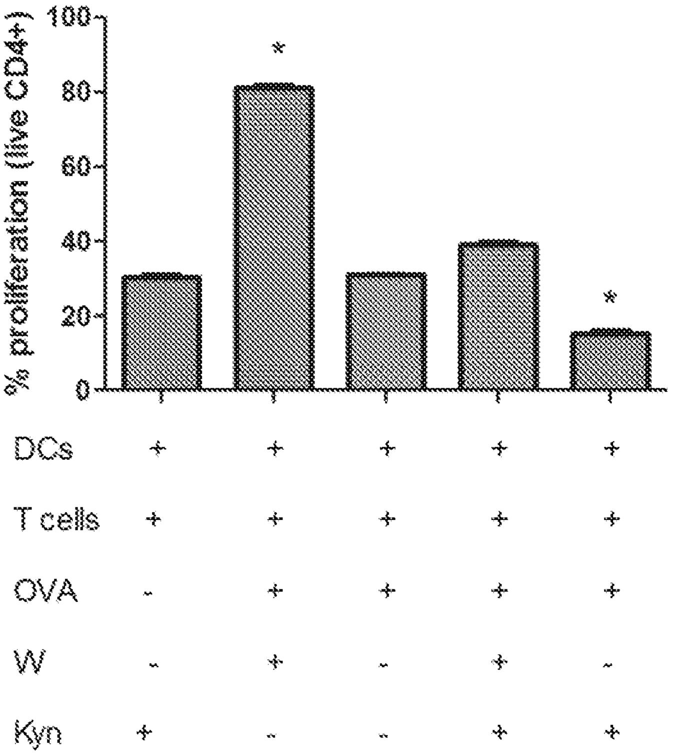
FIG. 17 shows a graph that can demonstrate CD4 positive T cells in stimulated and unstimulated DCs pretreated with IDO in the presence and absence of tryptophan and/or kynurenine.

FIG. 17 shows a graph demonstrating CD4 positive T cells in stimulated and unstimulated DCs pretreated with IDO in the presence and absence of tryptophan and/or kynurenine.

Figures 57A, 57B, 57C, 57D, 57E, 57F:
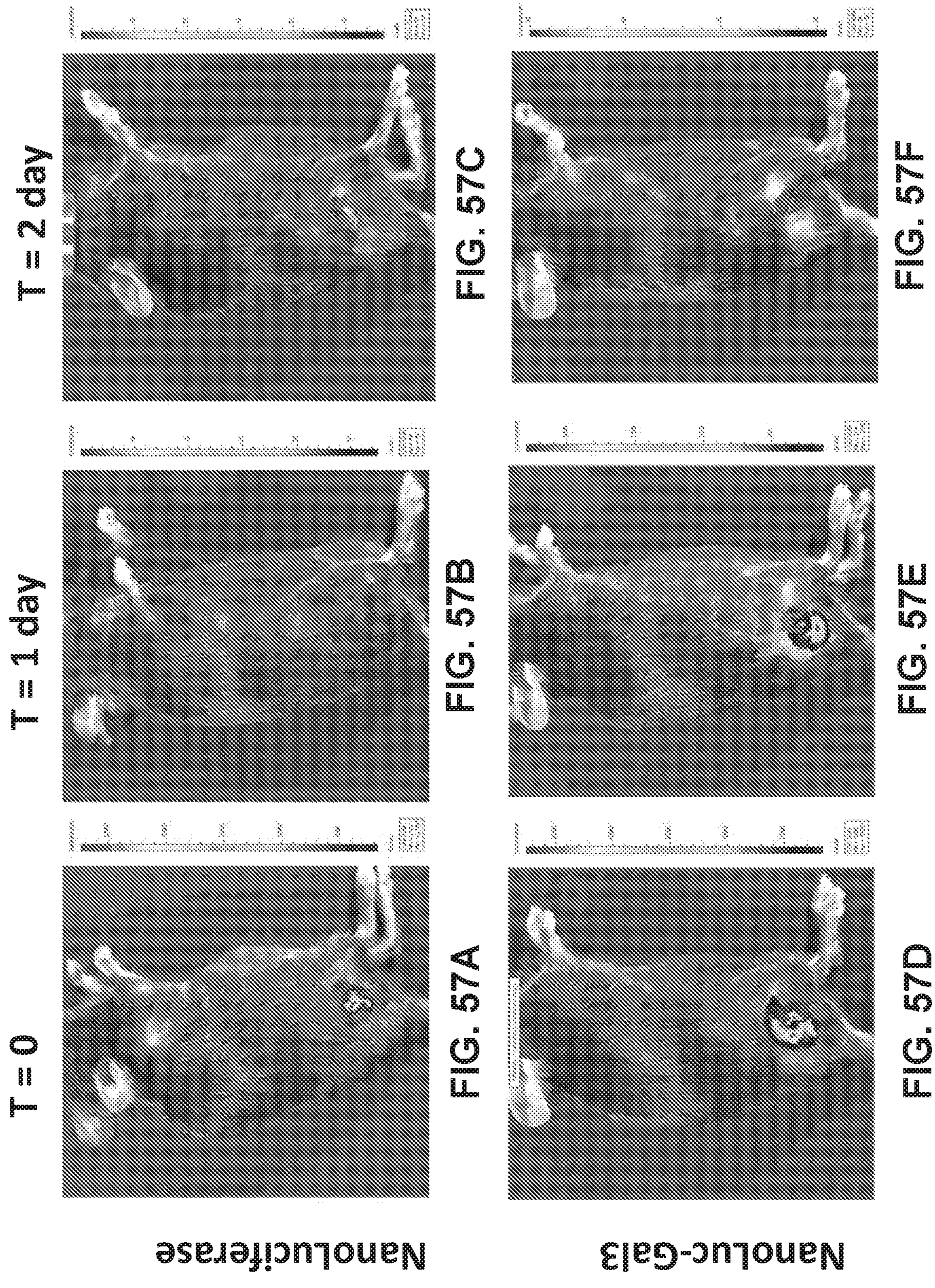
FIGS. 57A-57F show images demonstrating the luminescence at various time intervals after initial intramuscular injections of Nanoluciferase or NanoLuc-Gal3.
Figures 58A, 58B, 58C, 58D, 58E, 58F:
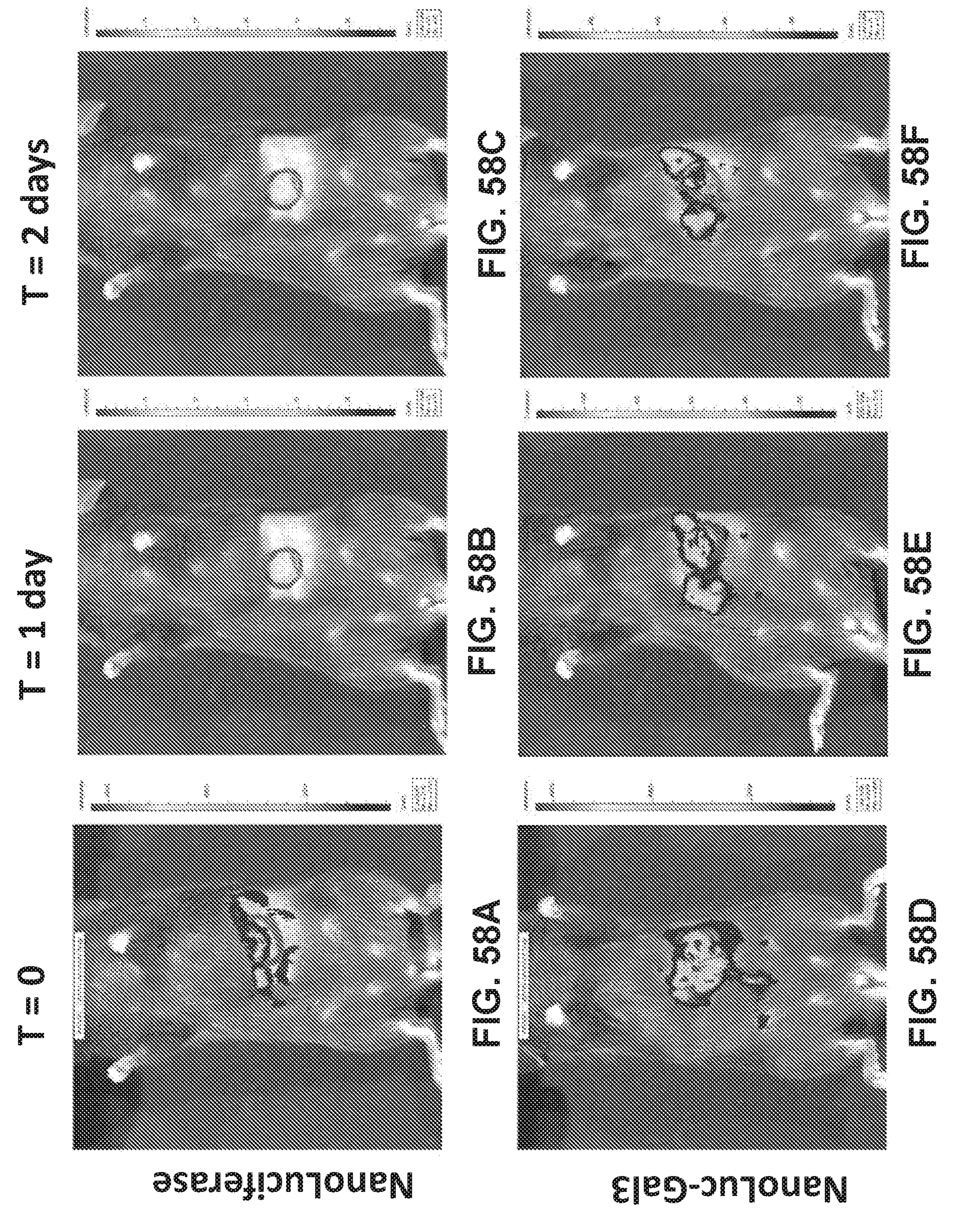
FIGS. 58A-58F show images demonstrating the luminescence at various time intervals after initial intraperitoneal injections of Nanoluciferase or NanoLuc-Gal3.
Figures 59A, 59B, 59C, 59D, 59E, 59F:
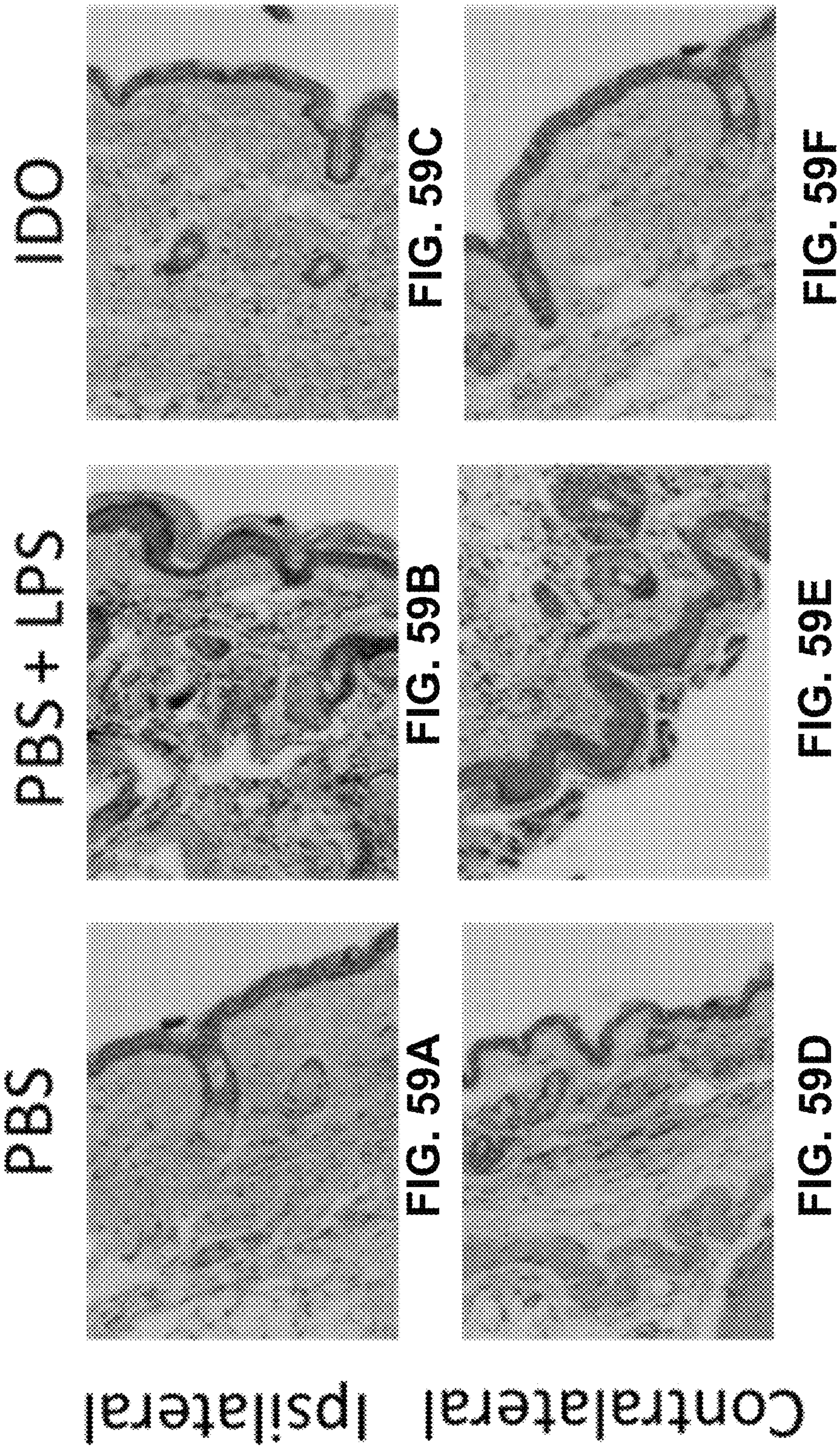
FIGS. 59A-59L show images demonstrating histology of the hock after injection of IDO, IDO-G3 or a control (PBS) with and without LPS induced inflammation.
Figure 59G:
Figure 59H:
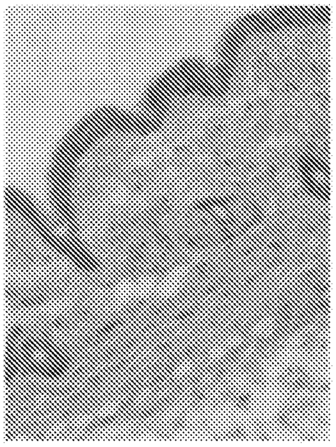
Figure 59I:
Figure 59J:
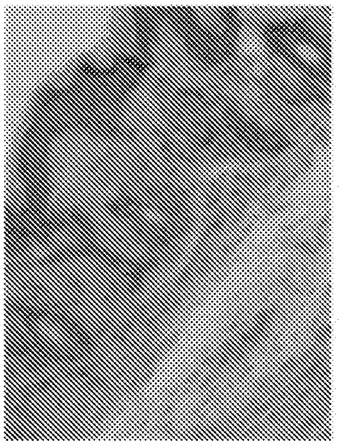
Figure 59K:
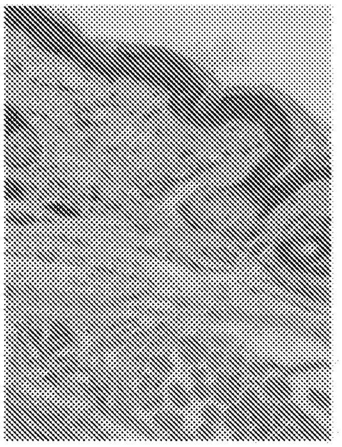
Figure 59L:

FIGS. 57-58 can demonstrate the effect(s) of IDO alone on cytokine secretion from dendritic cells (DCs). Briefly, bone marrow derived were treated with IDO for about 24 hours and challenged with lipopolysaccharide (LPS). Cytokine secretion was evaluated via ELISA and statistical significance was defined by * where $p<0.05$.

Figure 18:
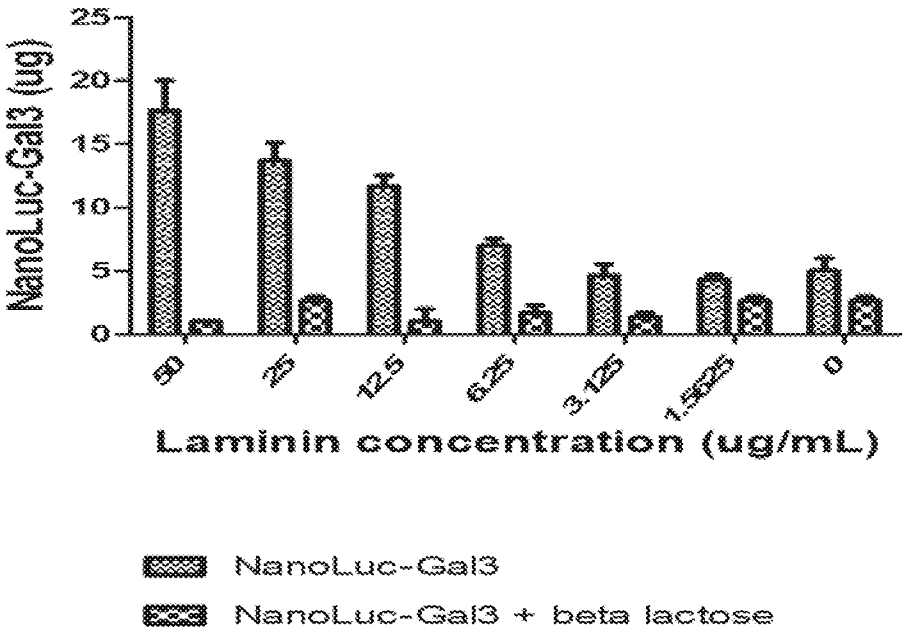
FIG. 18 shows a graph that can demonstrate galectin 3 binding affinity to a sugar moiety when fused to an enzyme on the N-terminus. Non-tissue culture treated polystyrene plates were coated with laminin at the specified concentrations. NanoLuc-Gal3 was added either in the presence or absence of excess β lactose and incubated for about 45 minutes at room temperature. Plates were then washed and Furimazine was added to detect bioluminescence.

FIG. 18 shows a graph demonstrating galectin 3 binding affinity to a sugar moiety when fused to an enzyme on the N-terminus. Non-tissue culture treated polystyrene plates were coated with laminin at the specified concentrations. NanoLuc-Gal3 was added either in the presence or absence of excess β lactose and incubated for about 45 minutes at room temperature. Plates were then washed and Furimazine was added to detect bioluminescence.

Figure 19:
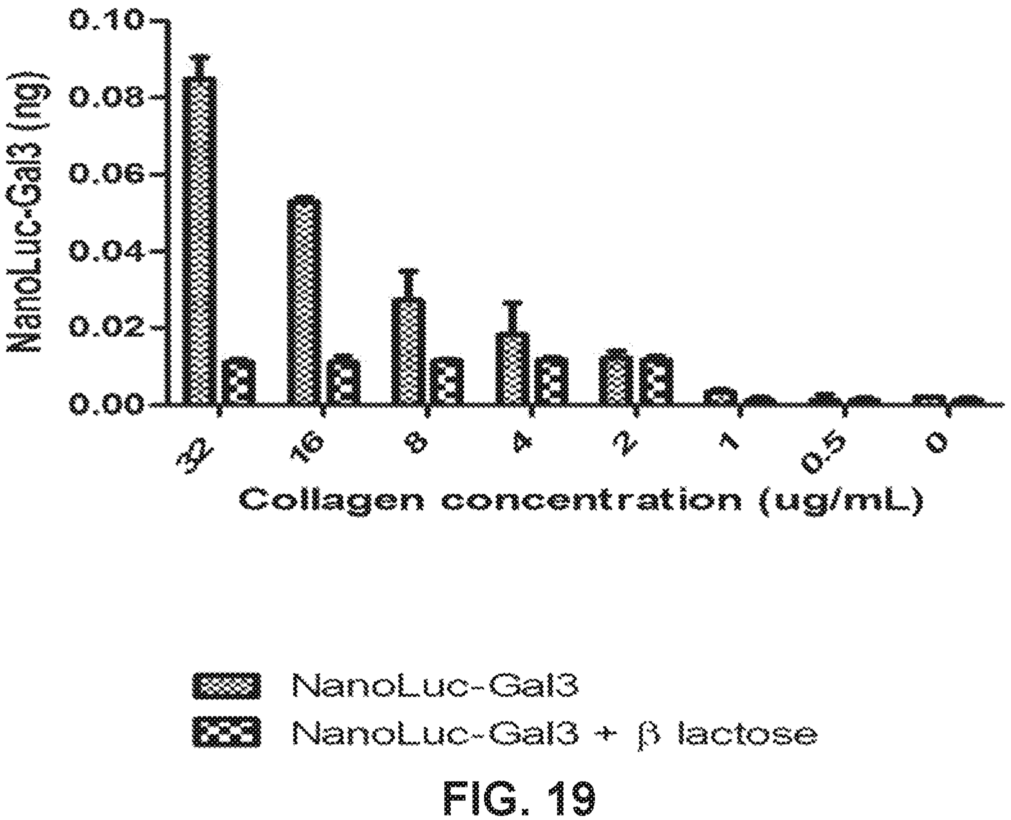
FIG. 19 shows a graph that can demonstrate galectin 3 binding affinity to a sugar moiety when fused to an enzyme on the N-terminus. Non-tissue culture treated polystyrene plates were coated with collagen type I at the specified concentrations. NanoLuc-Gal3 was added either in the presence or absence of excess β lactose and incubated for about 45 minutes at room temperature. Plates were then washed and Furimazine was added to detect bioluminescence.

FIG. 19 shows a graph demonstrating galectin 3 binding affinity to a sugar moiety when fused to an enzyme on the N-terminus. Non-tissue culture treated polystyrene plates were coated with collagen type I at the specified concentrations. NanoLuc-Gal3 was added either in the presence or absence of excess β lactose and incubated for about 45 minutes at room temperature. Plates were then washed and Furimazine was added to detect bioluminescence.

Figure 20:
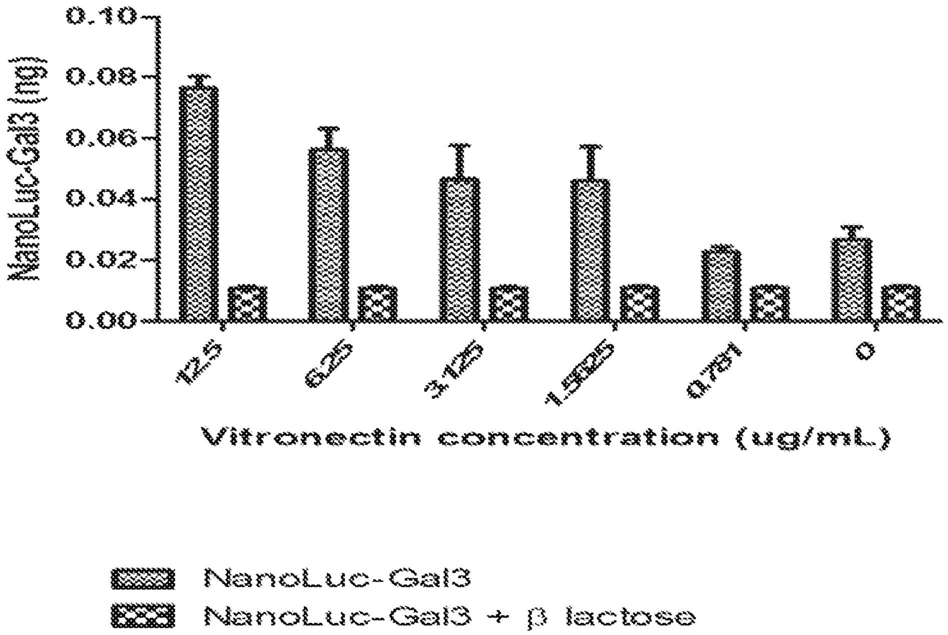
FIG. 20 shows a graph that can demonstrate galectin 3 binding affinity to a sugar moiety when fused to an enzyme on the N-terminus. Non-tissue culture treated polystyrene plates were coated with vitronectin at the specified concentrations. NanoLuc-Gal3 was added either in the presence or absence of excess β lactose and incubated for about 45 minutes at room temperature. Plates were then washed and Furimazine was added to detect bioluminescence.

FIG. 20 shows a graph demonstrating galectin 3 binding affinity to a sugar moiety when fused to an enzyme on the N-terminus. Non-tissue culture treated polystyrene plates were coated with vitronectin at the specified concentrations. NanoLuc-Gal3 was added either in the presence or absence of excess β lactose and incubated for about 45 minutes at room temperature. Plates were then washed and Furimazine was added to detect bioluminescence.

Figure 21:
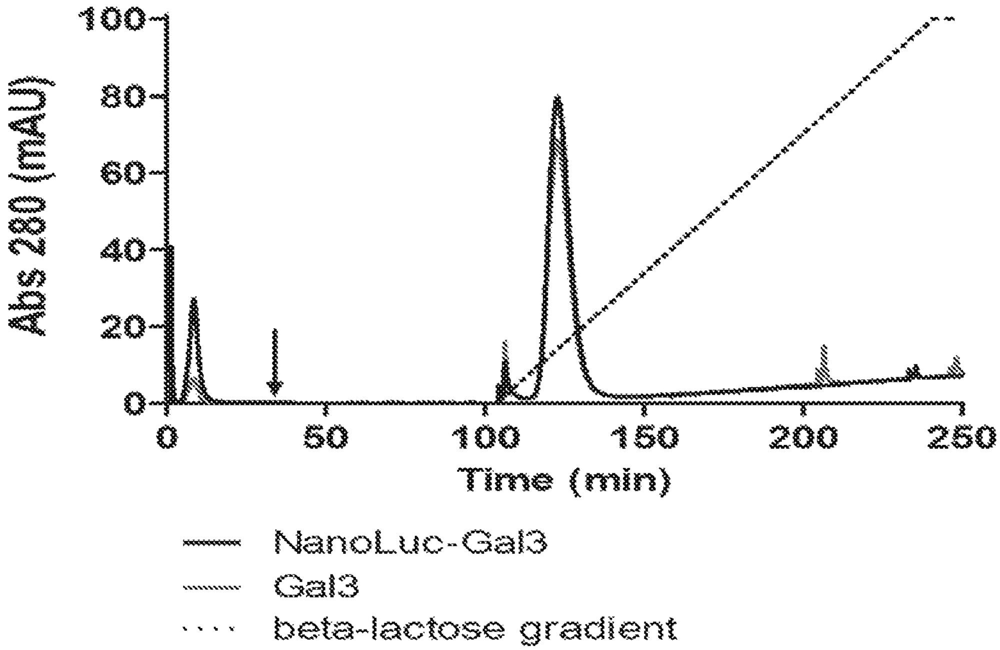
FIG. 21 shows a graph that can demonstrate that the nanoluciferase-galectin-3 fusion and wild-type galectin-3 have comparable carbohydrate binding affinity. Nanoluciferase-galectin-3 fusion and wild-type galectin-3 were bound to chromatography beads modified with alpha-lactose and then subjected to a gradient of aqueous buffer with increasing concentrations of soluble beta-lactose (dashed line). Nanoluciferase-galectin-3 fusion and wild-type galectin-3 eluted from the chromatography resin with a similar profile.

FIG. 21 shows a graph demonstrating that the nanoluciferase-galectin-3 fusion and wild-type galectin-3 have comparable carbohydrate binding affinity. Nanoluciferase-galectin-3 fusion and wild-type galectin-3 were bound to chromatography beads modified with alpha-lactose and then subjected to a gradient of aqueous buffer with increasing concentrations of soluble beta-lactose (dashed line). Nanoluciferase-galectin-3 fusion and wild-type galectin-3 eluted from the chromatography resin with a similar profile.

Figure 22:
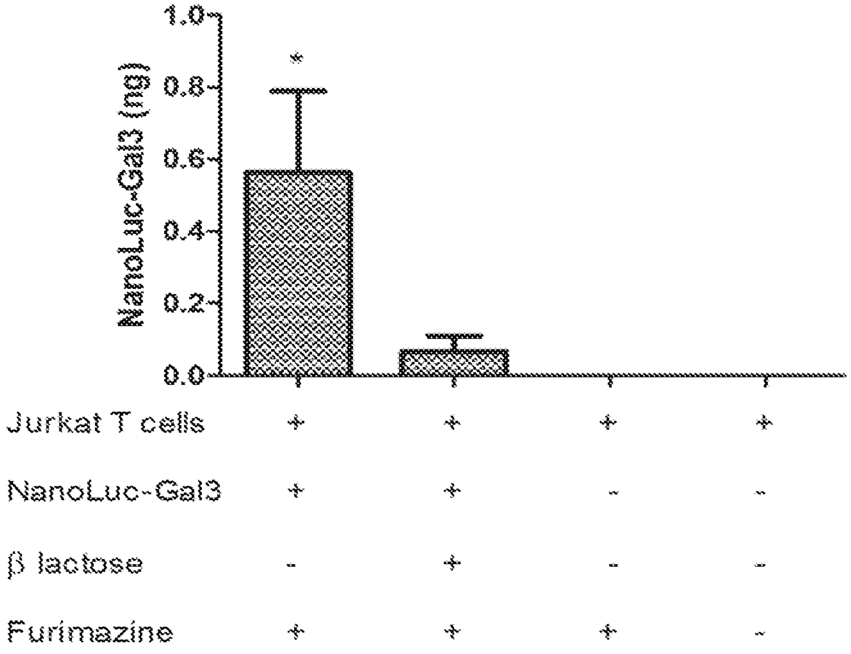
FIG. 22 shows a graph that can demonstrate retention of Galectin 3 binding affinity via the carbohydrate recognition domain to Jurkat T cells when fused with a model effector enzyme (NanoLuc) on the N-terminus of Galectin 3. Jurkat T cells were cultured with NanoLuc-Gal3 either in the presence or absence of excess β lactose for about 1 h at about 37° C. After about 1 h, cells were centrifuged and incubated with Furimazine to detect bioluminescence. Pair-wise significant difference (by ANOVA and Tukey's post hoc) is denoted by * where $p \leq 0.05$.

FIG. 22 shows a graph demonstrating retention of Galectin 3 binding affinity via the carbohydrate recognition domain to Jurkat T cells when fused with a model effector enzyme (NanoLuc) on the N-terminus of Galectin 3. Jurkat T cells were cultured with NanoLuc-Gal3 either in the presence or absence of excess β lactose for about 1 h at about 37° C. After about 1 h, cells were centrifuged and incubated with Furimazine to detect bioluminescence. Pair-wise significant difference (by ANOVA and Tukey's post hoc) is denoted by * where $p\leq 0.05$.

Figure 23:
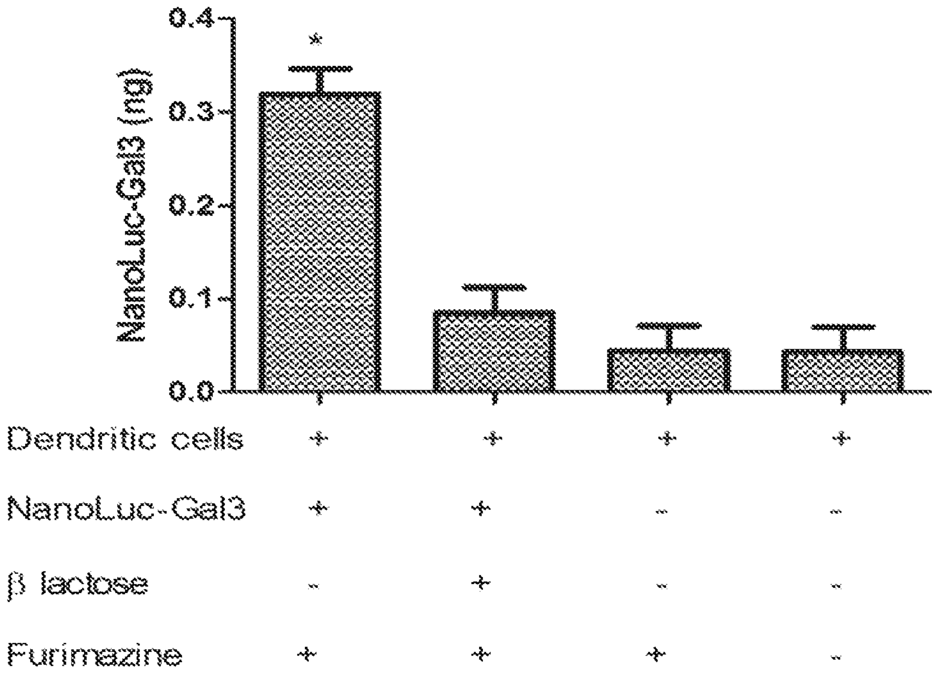
FIGS. 23-24 show graphs that can demonstrate galectin 3 binding to dendritic cells, which can be through the carbohydrate recognition domain, and does not act as a pathogen associated molecular pattern. DCs were cultured with NanoLuc-Gal3 either in the presence or absence of excess β lactose for 1 h at 37° C. After 1 h, cells were washed and incubated with Furimazine to detect bioluminescence (FIG. 23). In a separate experiment DCs were cultured with NanoLuc-Gal3 for 24 h at 37° C. After 24 h cells were washed and immunostained for maturation markers CD80, CD86 and MHC II (FIG. 24). Pair-wise significant difference (by ANOVA and Tukey's post hoc) is denoted by * where $p<0.05$.
Figure 24:
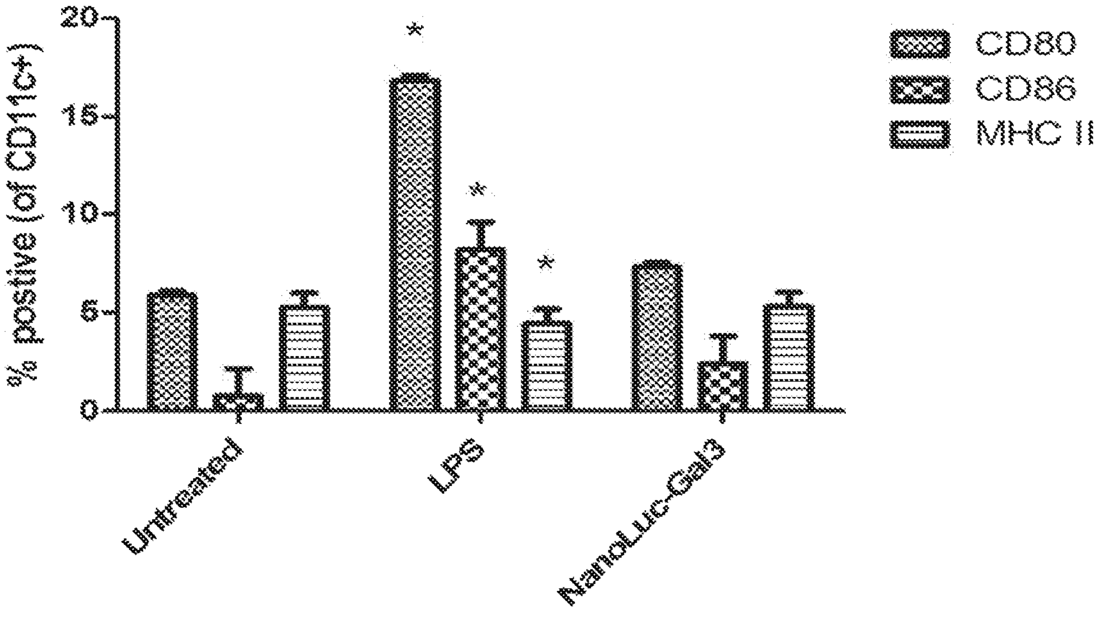

FIGS. 23-24 show graphs demonstrating galectin 3 binding to dendritic cells, which can be through the carbohydrate recognition domain, and does not act as a pathogen associated molecular pattern. DCs were cultured with NanoLuc-Gal3 either in the presence or absence of excess β lactose for 1 h at 37° C. After 1 h, cells were washed and incubated with Furimazine to detect bioluminescence (FIG. 23). In a separate experiment DCs were cultured with NanoLuc-Gal3 for 24 h at 37° C. After 24 h cells were washed and immunostained for maturation markers CD80, CD86 and MHC II (FIG. 24). Pair-wise significant difference (by ANOVA and Tukey's post hoc) is denoted by * where $p<0.05$.

Figure 25:
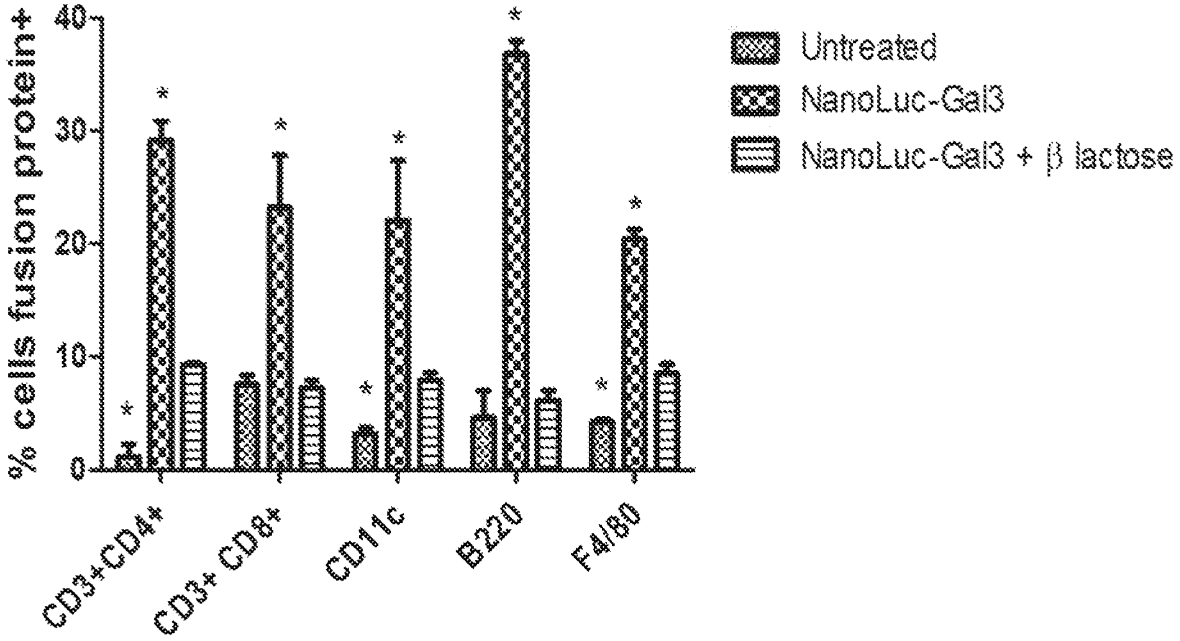
FIG. 25 shows a graph that can demonstrate Galectin-3 binding to primary splenocytes when fused with a model enzyme through the N-terminus. Splenocytes were incubated with NanoLuc-Gal3 fusion for 45 mins at RT either in the presence or absence of excess β lactose. Cells were immunostained and specific cell binding was assessed by flow cytometry of T cells (CD3, CD4, CD8), dendritic cells (CD11c), B cells (B220) and macrophages (F4/80). Pair-wise significant difference (by ANOVA and Tukey's post hoc) is denoted by * where $p<0.05$.

FIG. 25 shows a graph demonstrating Galectin 3 binding to primary splenocytes when fused with a model enzyme through the N-terminus. Splenocytes were incubated with NanoLuc-Gal3 fusion for 45 mins at RT either in the presence or absence of excess β lactose. Cells were immunostained and specific cell binding was assessed by flow cytometry of T cells (CD3, CD4, CD8), dendritic cells (CD11c), B cells (B220) and macrophages (F4/80). Pair-wise significant difference (by ANOVA and Tukey's post hoc) is denoted by * where $p<0.05$.

Figure 26:
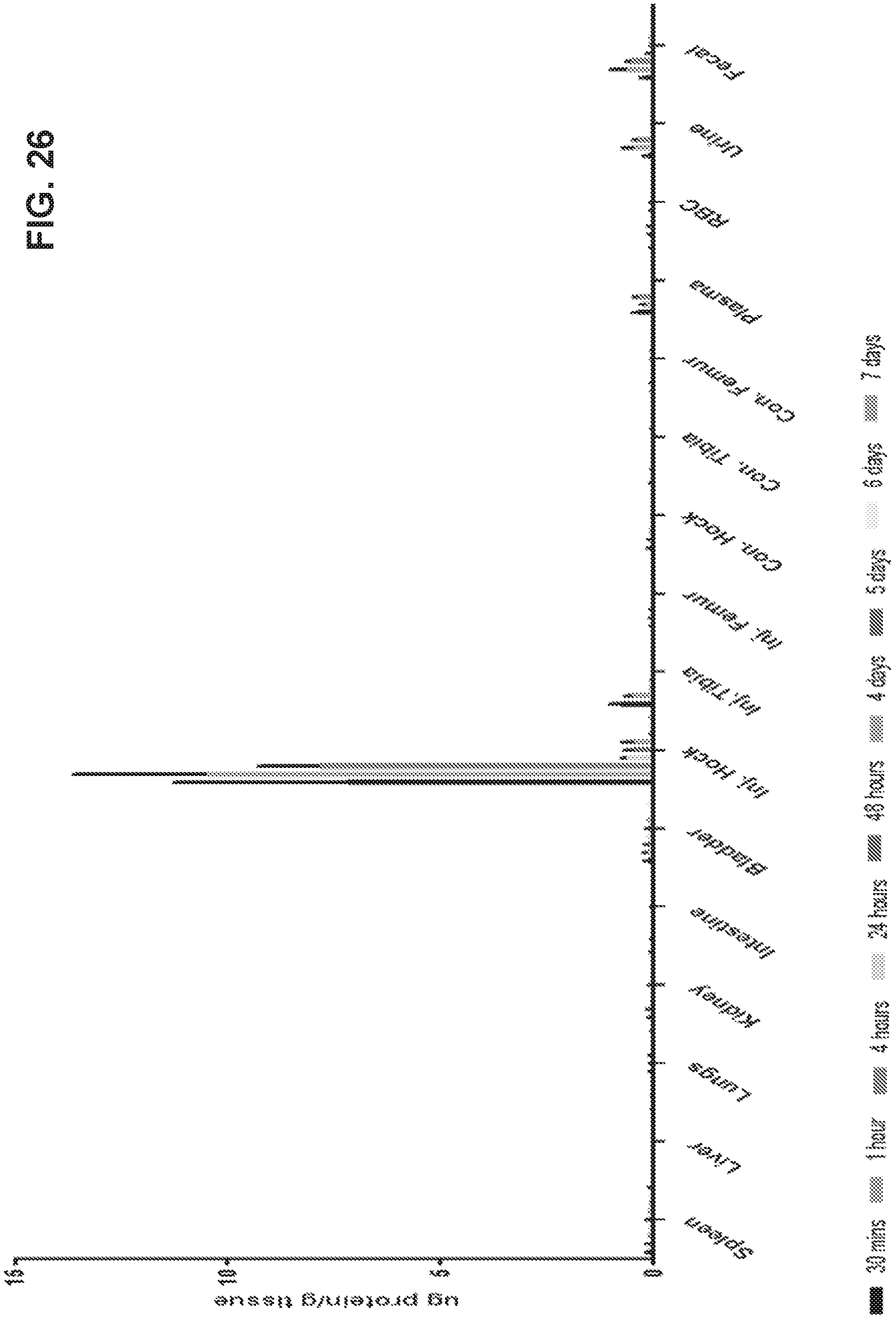
FIG. 26 shows a graph graphs that can demonstrate Galectin 3 provides retention of fusion moiety at the injection. NanoLuc-Gal3 fusion or was injected into the hock of 8 week old female C57BL/6 mice. After the specified time points (30 mins, 1 h, 4 h, 24 h, 48 h, 4 d, 5 d, 6 d and 7 d for NanoLuc-Gal3) organs and tissues were excised and incubated with furimazine to detect active luciferase domains which correlate to amount of protein in each tissue.

FIG. 26 show graphs demonstrating Galectin 3 provides retention of fusion moiety at the injection site and migration to lymph nodes. NanoLuc-Gal3 fusion was injected into the hock of 8 week old female C57BL/6 mice. After the specified time points (30 mins, 1 h, 4 h, 24 h, 48 h, 4 d, 5 d, 6 d and 7 d for NanoLuc-Gal3) organs and tissues were excised and incubated with furimazine to detect active luciferase domains which correlate to amount of protein in each tissue.

FIGS. 54A-54H show images demonstrating the luminescence at various time intervals after initial subcutaneous injections of Nanoluciferase or NanoLuc-Gal3 at the hock.

FIGS. 55A-55F show images demonstrating the luminescence at various time intervals after initial subcutaneous injections of Nanoluciferase or NanoLuc-Gal3 at the scruff.

FIGS. 56A-56H show images demonstrating the luminescence at various time intervals after initial subcutaneous injections of Nanoluciferase or NanoLuc-Gal3 at the abdomen.

FIGS. 57A-57F show images demonstrating the luminescence at various time intervals after initial intramuscular injections of Nanoluciferase or NanoLuc-Gal3.

FIGS. 58A-58F show images demonstrating the luminescence at various time intervals after initial intraperitoneal injections of Nanoluciferase or NanoLuc-Gal3.

Figure 66A:
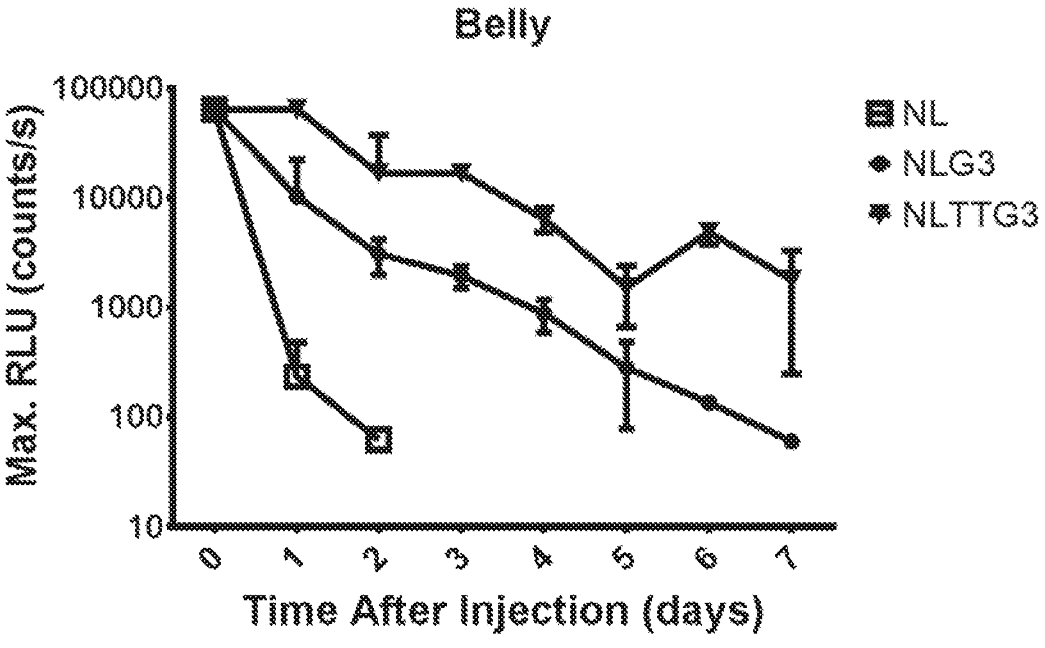
FIGS. 66A-66D show graphs that can demonstrate the bioluminescence results after localized subcutaneous (subQ) injections of NL-G3 and NL in various locations (belly, FIG. 66A; IM, FIG. 66B, scruff, FIG. 66C; and intraperitoneal, FIG. 66D).
Figure 66B:
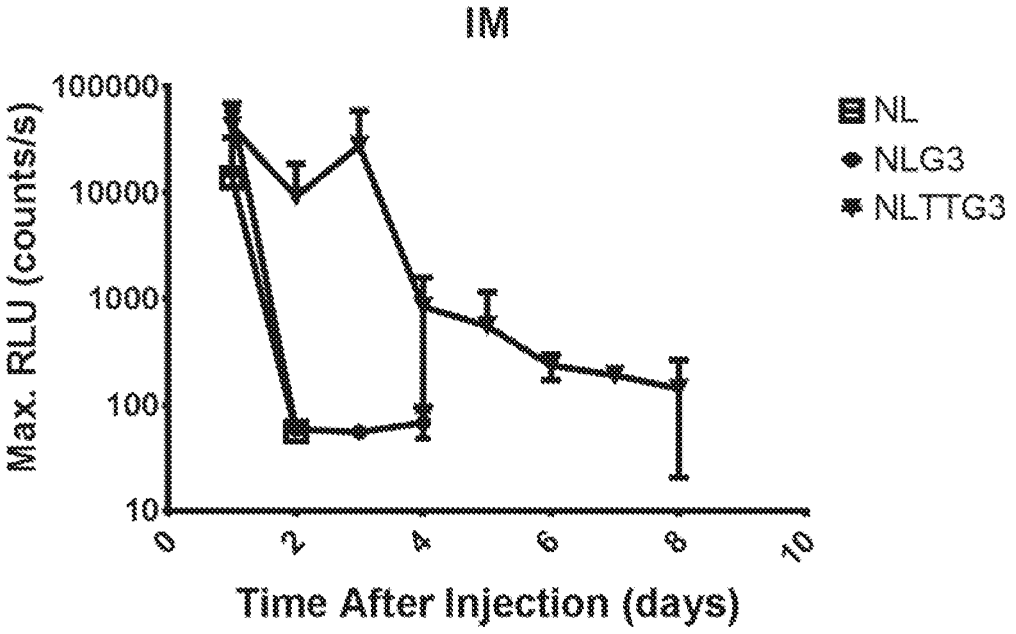
Figure 66C:
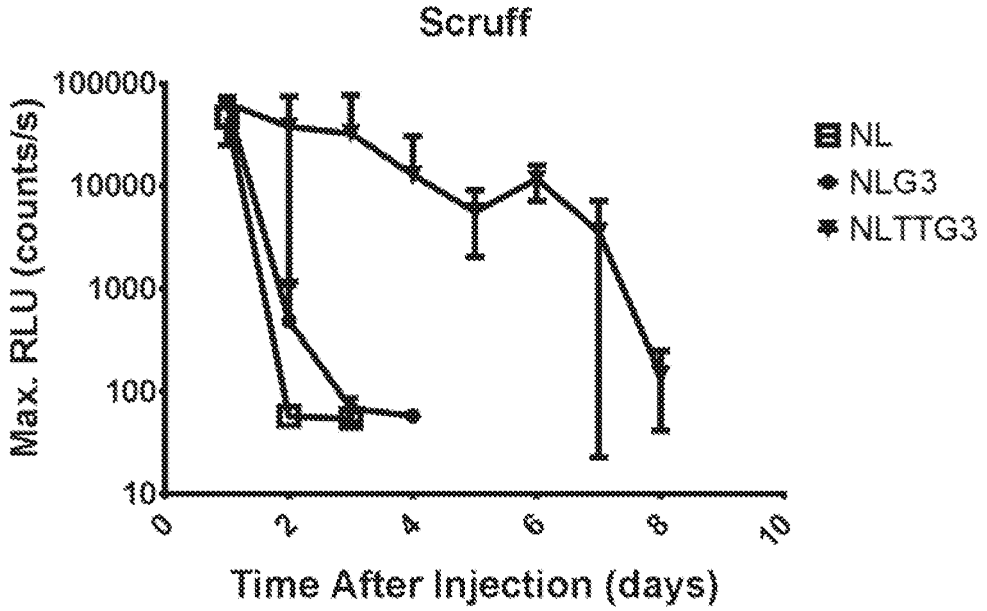
Figure 66D:
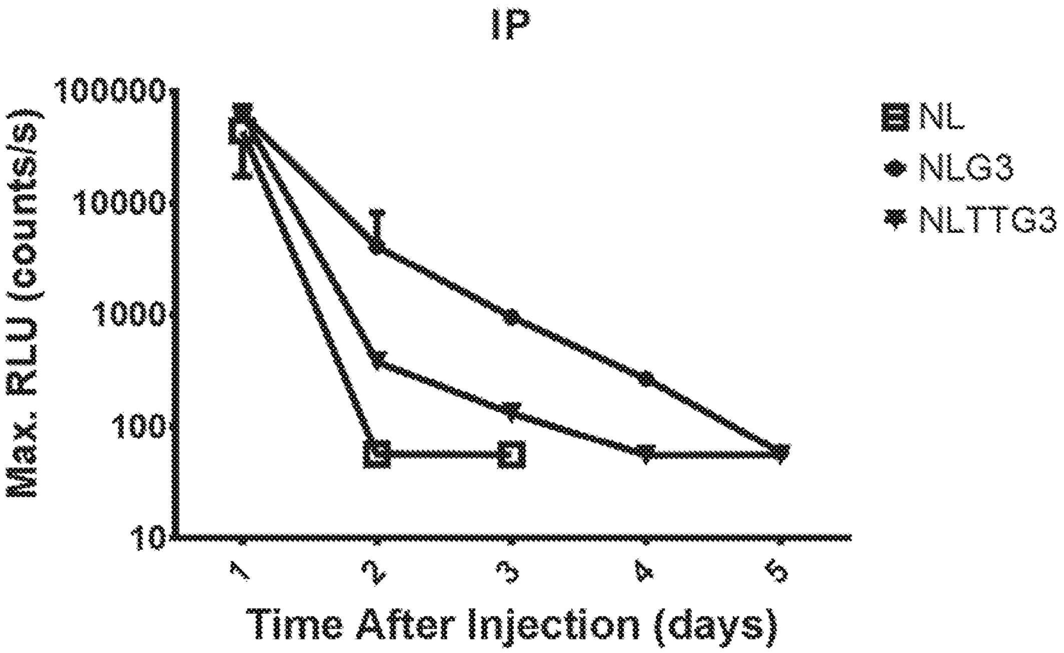
Figures 67A, 67B, 67C, 67D, 67E, 67F:
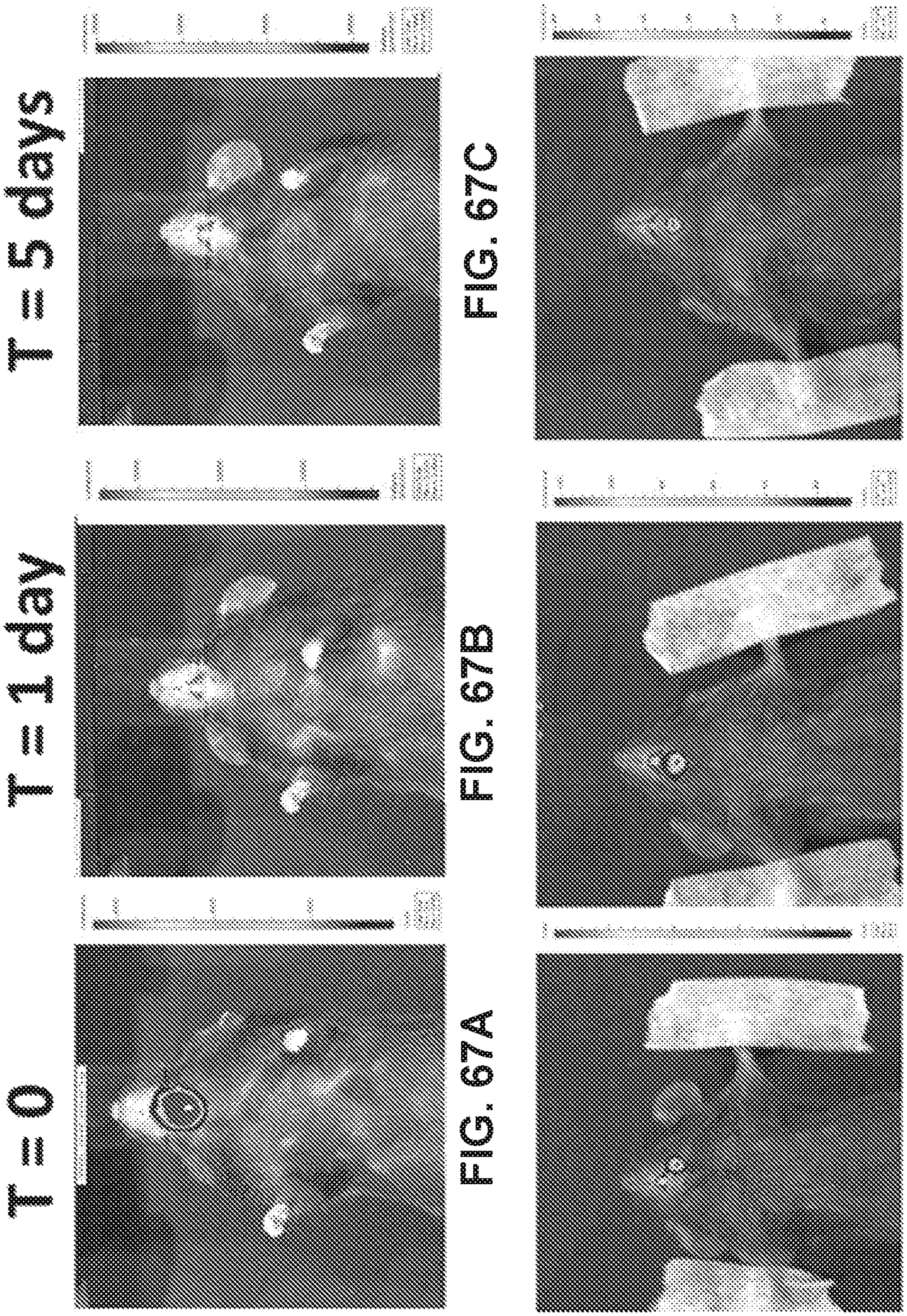
FIGS. 67A-67F shows images that can demonstrate the in vivo bioluminescence after localized injection of NL or NL-G3 into the subgingiva at various times after injection and can demonstrate retention at the site of injection.

FIGS. 66A-66D show graphs that can demonstrate the bioluminescence results after localized subcutaneous (subQ) injections or intramuscular (IM) of NL-G3 and NL in various locations (belly, FIG. 66A; IM, FIG. 66B, scruff, FIG. 66C; and intraperitoneal, FIG. 66D).

Figure 27:
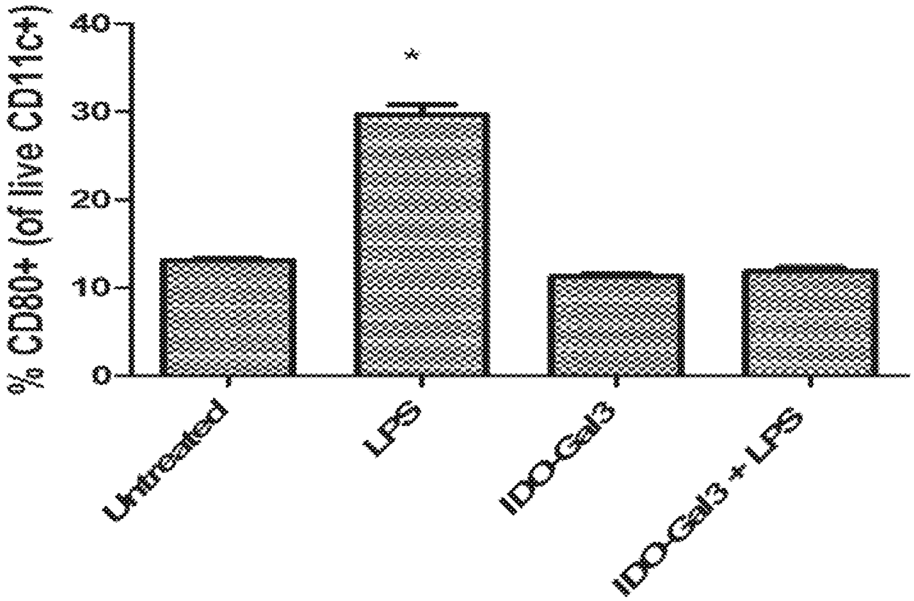
FIGS. 27-29 show graphs that can demonstrate DCs treated with soluble IDO-Gal3 resist LPS induced maturation. Murine bone marrow derived DCs were incubated with soluble IDO-Gal3 fusion for 24 h and challenged with LPS for an additional 24 h. Untreated and LPS groups were included for comparison. Cells were immunostained for maturation markers CD80 (FIG. 27), CD86 (FIG. 28) and MHC II (FIG. 29). Viable cells expressing CD11c and the marker of interest were assessed via flow cytometry and shown as percent positive. Pair-wise significant difference (by ANOVA and Tukey's post hoc) is denoted by * where $p<0.05$
Figure 28:
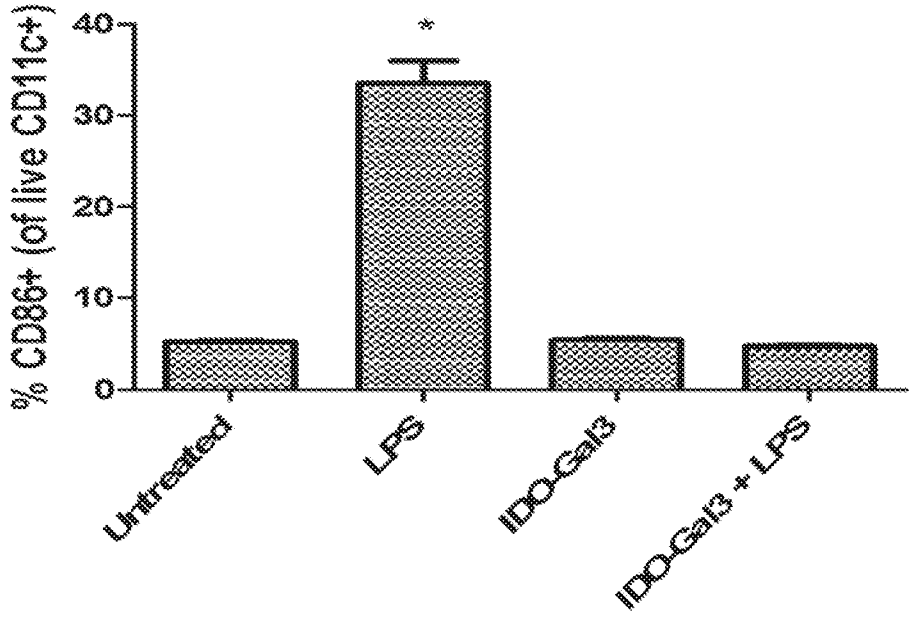
Figure 29:
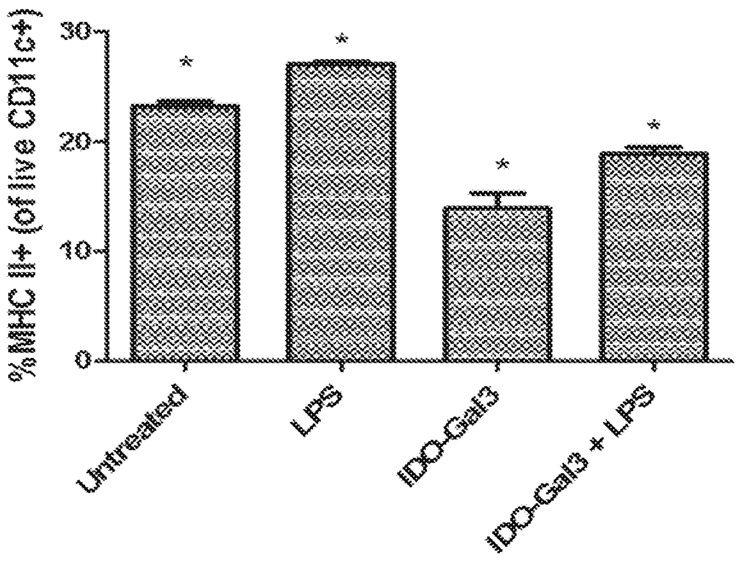
Figure 30:
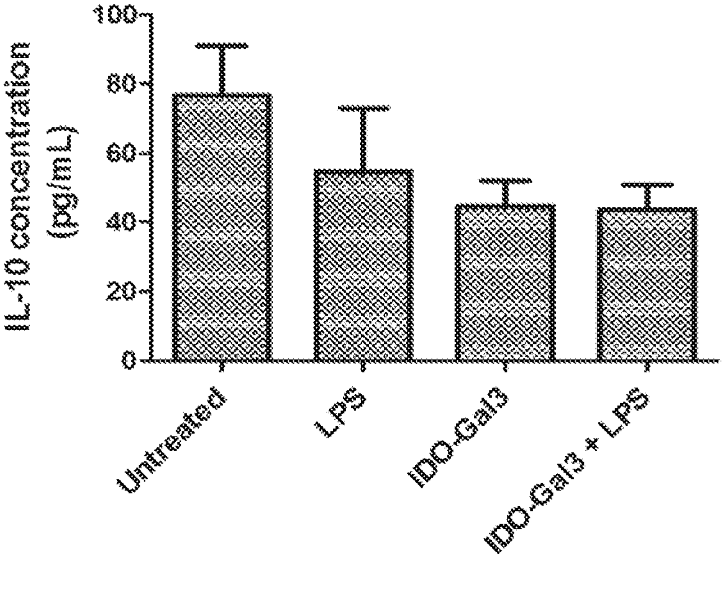
FIGS. 30-31 show graphs that can demonstrate DCs treated with exogenous IDO-Gal3 do not secrete IL-12 and maintain IL-10 production. DCs were incubated with soluble IDO-Gal3 for 24 h and challenged with LPS for an additional 24 h. Untreated and LPS groups were included for comparison. IL-10 secretion (FIG. 30) and IL-12p70 secretion (FIG. 31) were evaluated via ELISA of the supernatant of each condition. Pair-wise significant difference (by ANOVA and Tukey's post hoc) is denoted by * where $p<0.05$.
Figure 31:
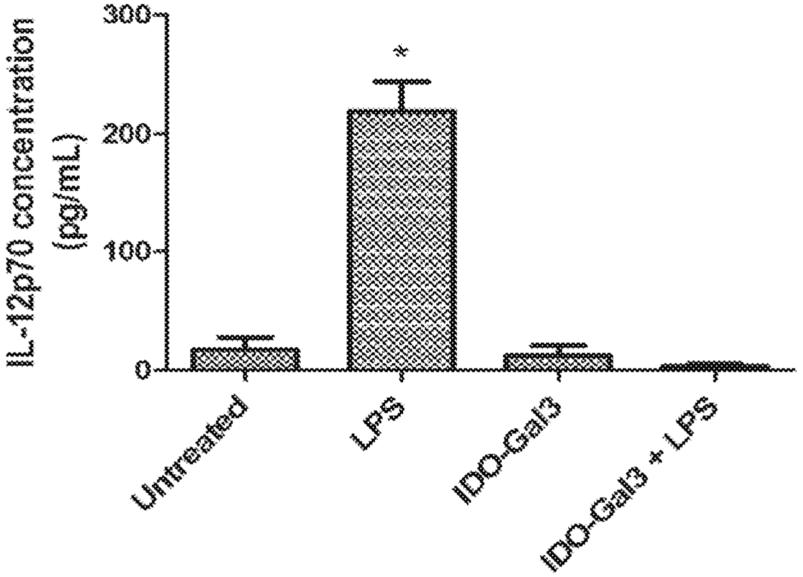

FIGS. 27-29 show graphs demonstrating DCs treated with soluble IDO-Gal3 resist LPS induced maturation. Murine bone marrow derived DCs were incubated with soluble IDO-Gal3 fusion for 24 h and challenged with LPS for an additional 24 h. Untreated and LPS groups were included for comparison. Cells were immunostained for maturation markers CD80 (FIG. 27), CD86 (FIG. 28) and MHC II (FIG. 29). Viable cells expressing CD11c and the marker of interest were assessed via flow cytometry and shown as percent positive. Pair-wise significant difference (by ANOVA and Tukey's post hoc) is denoted by * where $p<0.05$ FIGS. 30-31 show graphs demonstrating DCs treated with exogenous IDO-Gal3 do not secrete IL-12 and maintain IL-10 production. DCs were incubated with soluble IDO-Gal3 for 24 h and challenged with LPS for an additional 24 h. Untreated and LPS groups were included for comparison. IL-10 secretion (FIG. 30) and IL-12p70 secretion (FIG. 31) were evaluated via ELISA of the supernatant of each condition. Pair-wise significant difference (by ANOVA and Tukey's post hoc) is denoted by * where $p<0.05$.

Figure 32:
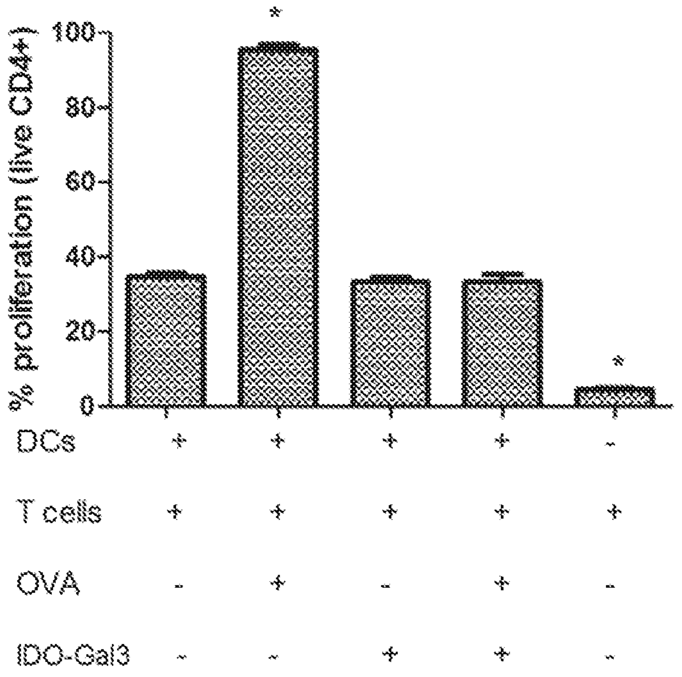
FIG. 32 shows a graph that can demonstrate DCs treated with IDO-Gal3 suppress antigen specific T cell proliferation. DCs were incubated IDO-Gal3 for 24 h. After 24 h DCs were washed and relevant groups treated with ovalbumin for 3 h. After 3 h, DCs were washed and co-cultured with CD4+ CFSE labeled T cells isolated from OT-II mice for 4 days. After 4 days T cells were stained with LIVE/DEAD Fixable Near-IR Dead Cell Stain Kit and CD4 and proliferation assessed via CFSE dilution by flow cytometry. Pair-wise significant difference (by ANOVA and Tukey's post hoc) is denoted by * where $p<0.05$.

FIG. 32 shows a graph demonstrating DCs treated with IDO-Gal3 suppress antigen specific T cell proliferation. DCs were incubated IDO-Gal3 for 24 h. After 24 h DCs were washed and relevant groups treated with ovalbumin for 3 h. After 3 h, DCs were washed and co-cultured with CD4+ CFSE labeled T cells isolated from OT-II mice for 4 days. After 4 days T cells were stained with LIVE/DEAD Fixable Near-IR Dead Cell Stain Kit and CD4 and proliferation assessed via CFSE dilution by flow cytometry. Pair-wise significant difference (by ANOVA and Tukey's post hoc) is denoted by * where $p<0.05$.

Figure 33:
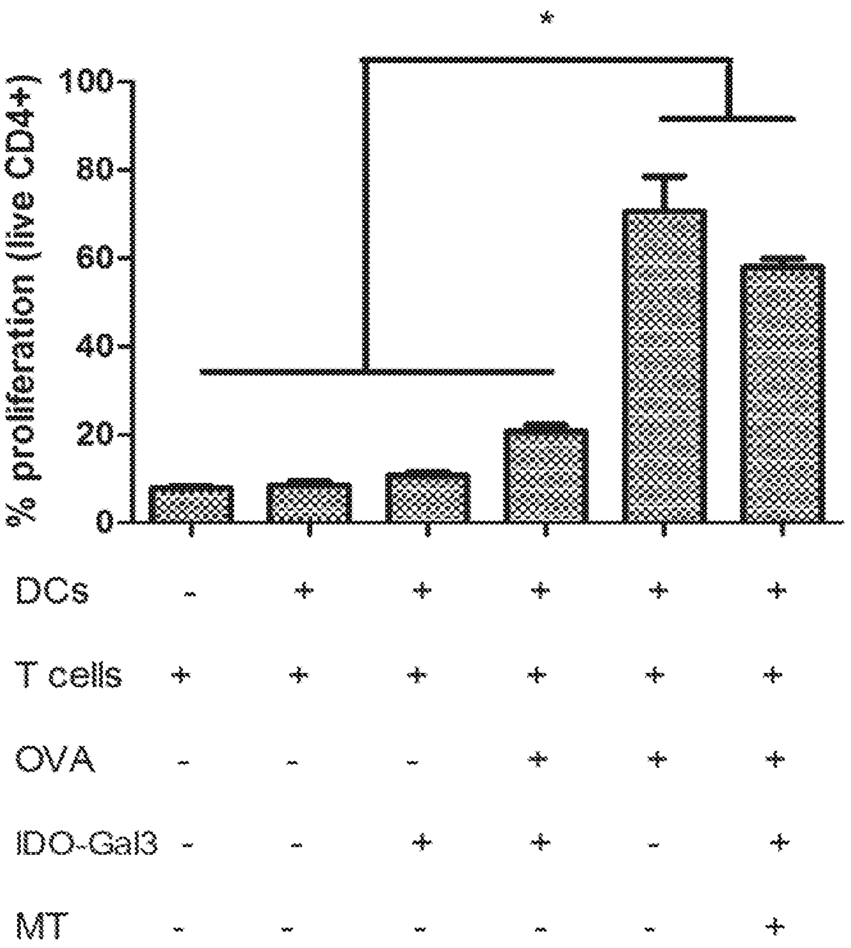
FIG. 33 shows a graph that can demonstrate fusion-treated DC mediated T cell suppression is active enzyme dependent. DCs were incubated with IDO-Gal3 fusion and methyl tryptophan, an IDO inhibitor, for 24 h. After 24 h DCs were washed and relevant groups treated with ovalbumin for 3 h. After 3 h, DCs were washed and co-cultured with CD4+ CFSE labeled T cells isolated from OT-II mice for 4 days. T cells were stained with LIVE/DEAD Fixable Near-IR Dead Cell Stain Kit and CD4 and proliferation assessed via CFSE dilution by flow cytometry. Pair-wise significant difference (by ANOVA and Tukey's post hoc) is denoted by * where $p<0.05$.

FIG. 33 shows a graph demonstrating fusion-treated DC mediated T cell suppression is active enzyme dependent. DCs were incubated with IDO-Gal3 fusion and methyl tryptophan, an IDO inhibitor, for 24 h. After 24 h DCs were washed and relevant groups treated with ovalbumin for 3 h. After 3 h, DCs were washed and co-cultured with CD4+ CFSE labeled T cells isolated from OT-II mice for 4 days. T cells were stained with LIVE/DEAD Fixable Near-IR Dead Cell Stain Kit and CD4 and proliferation assessed via CFSE dilution by flow cytometry. Pair-wise significant difference (by ANOVA and Tukey's post hoc) is denoted by * where $p<0.05$.

Figure 34:
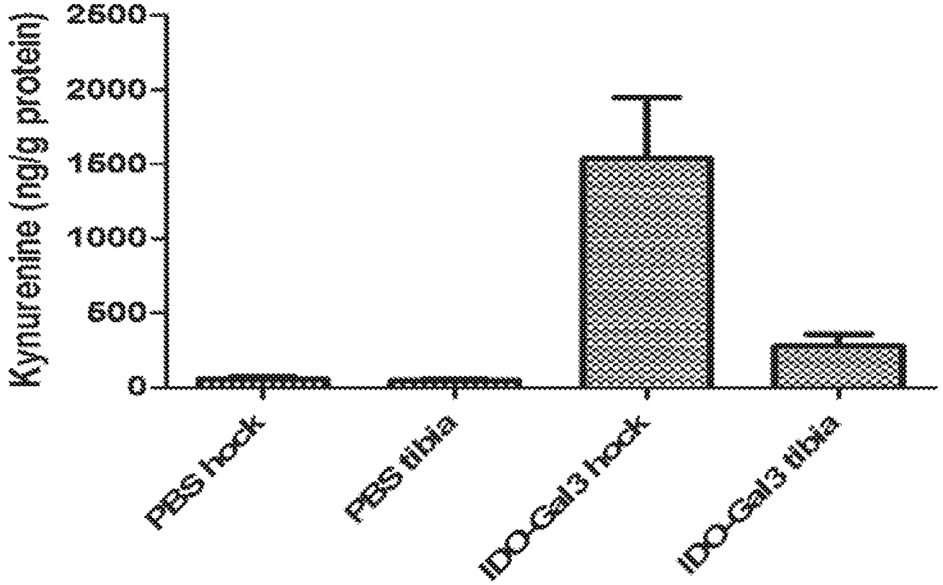
FIGS. 34-36 show graphs that can demonstrate that IDO-Gal3 modulates metabolism in vivo at the injection site and adjacent tissues. IDO-Gal3 was injected into the hock of C57BL/6 mice. 1 h post injection the hock and tibia regions were harvested, de-boned and flash frozen for mass spectrometry analysis of kynurenine (FIG. 34), tryptophan (FIG. 35), and the K/T ratio (FIG. 36).
Figure 35:
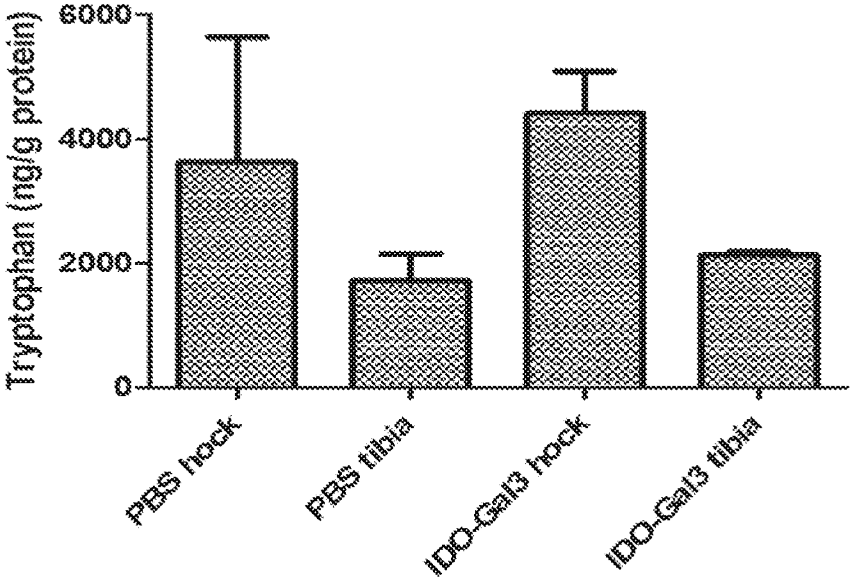
Figure 36:
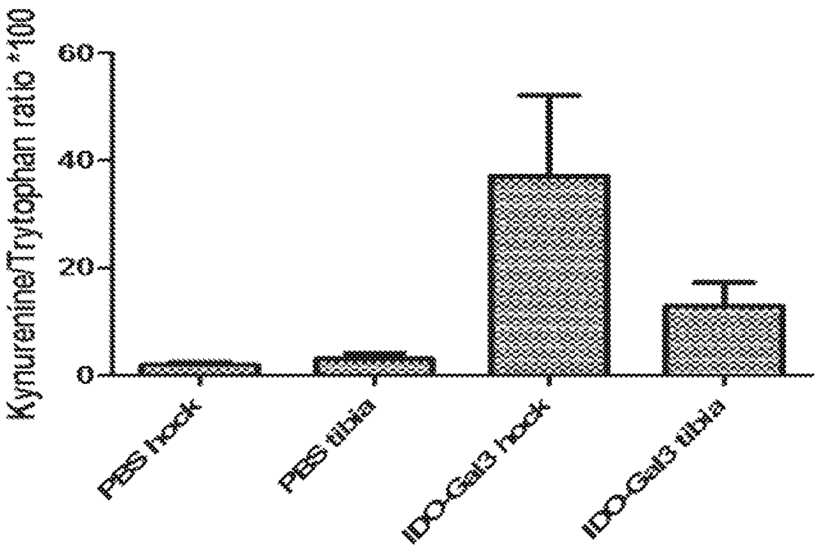

FIGS. 34-36 show graphs demonstrating IDO-Gal3 modulates metabolism in vivo at the injection site and adjacent tissues. IDO-Gal3 was injected into the hock of C57BL/6 mice. 1 h post injection the hock and tibia regions were harvested, de-boned and flash frozen for mass spectrometry analysis of kynurenine (FIG. 34), tryptophan (FIG. 35), and the K/T ratio (FIG. 36).

Figure 37:
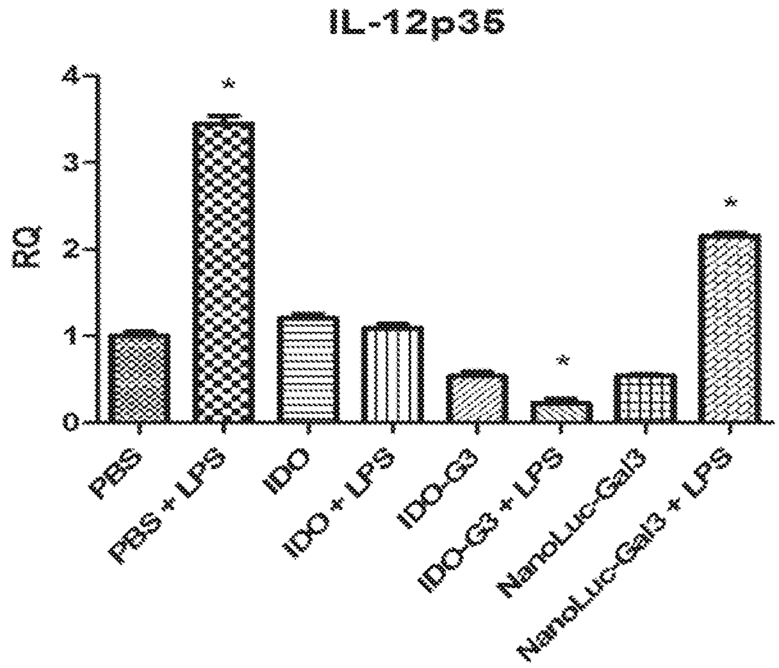
FIG. 37-42 shows a graph that can demonstrate that IDO-Gal3 suppresses inflammatory cytokine gene expression in vivo at 24 hours. IDO-Gal3 or relevant controls were injected in the hock of C57BL/6 mice and challenged with LPS 24 hours post fusion protein administration. Two hours post LPS challenge the injection site was harvested, de-boned and its genetic profile analyzed through qPCR (as measured using the relative quantification (RQ) method). Pair-wise significant difference (by ANOVA and Tukey's post hoc) is denoted by * where $p<0.05$.
Figure 38:
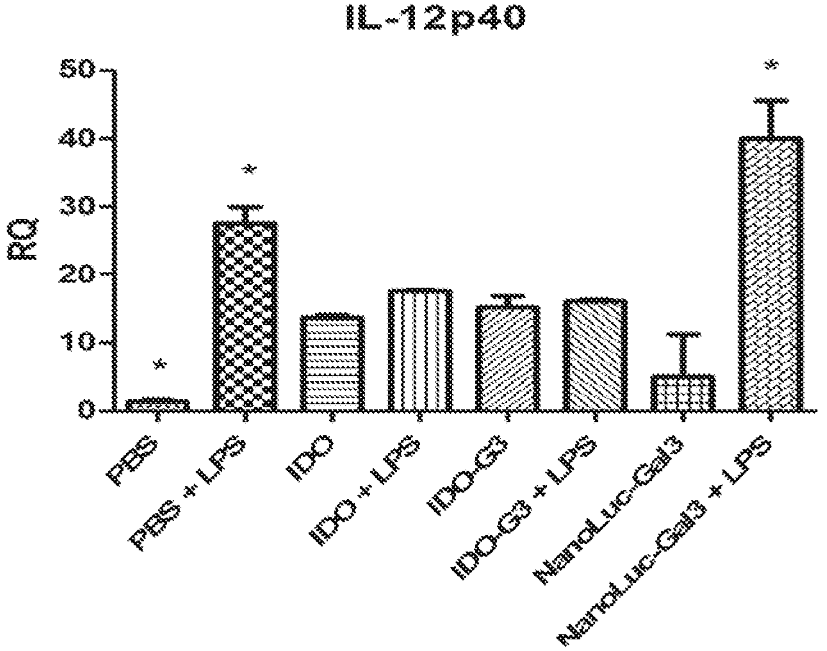
Figure 39:
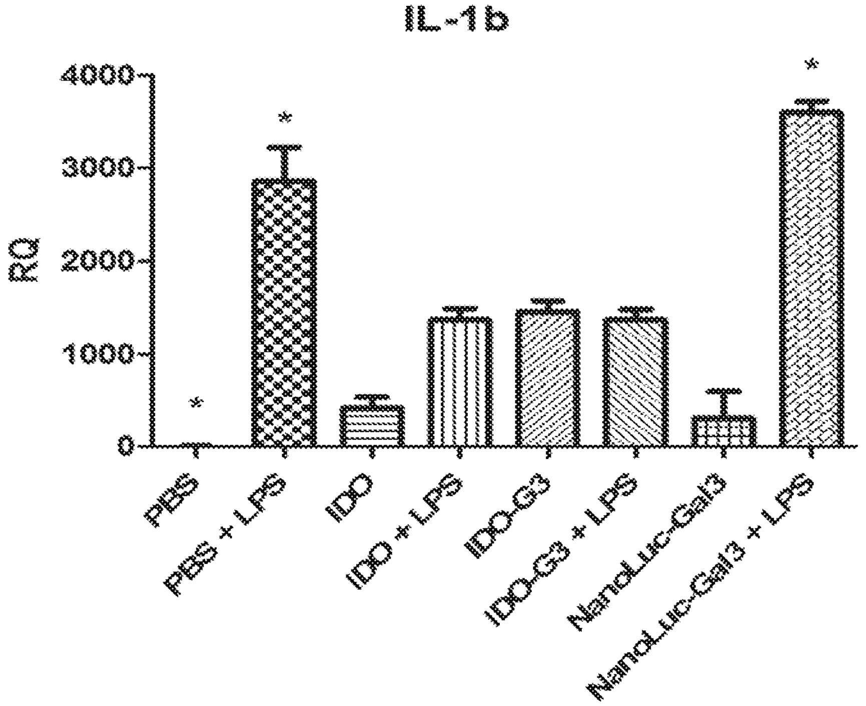
Figure 40:
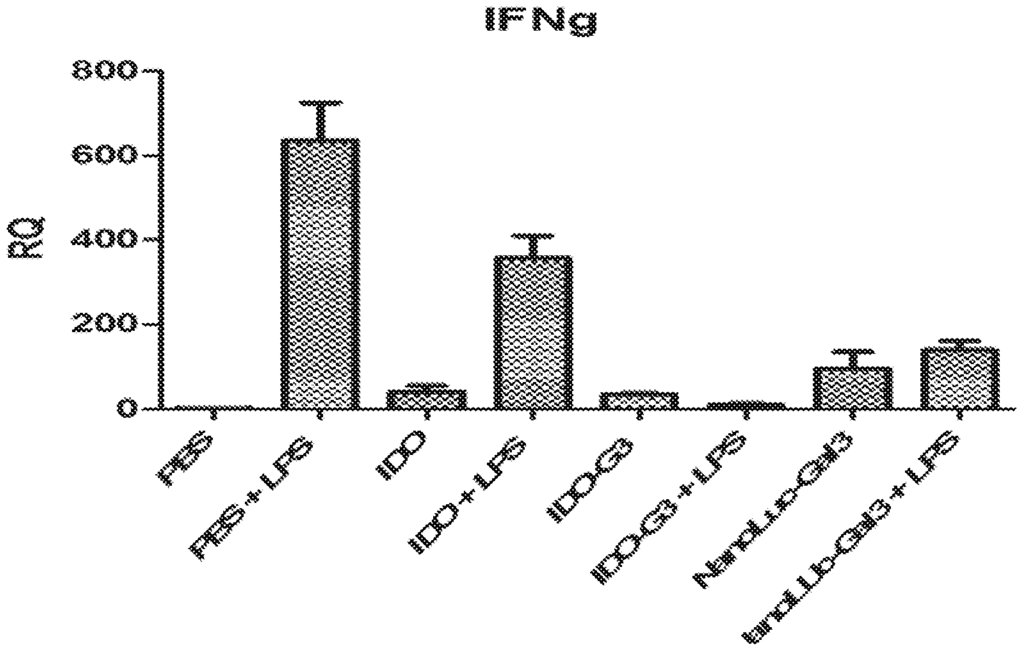
Figure 41:
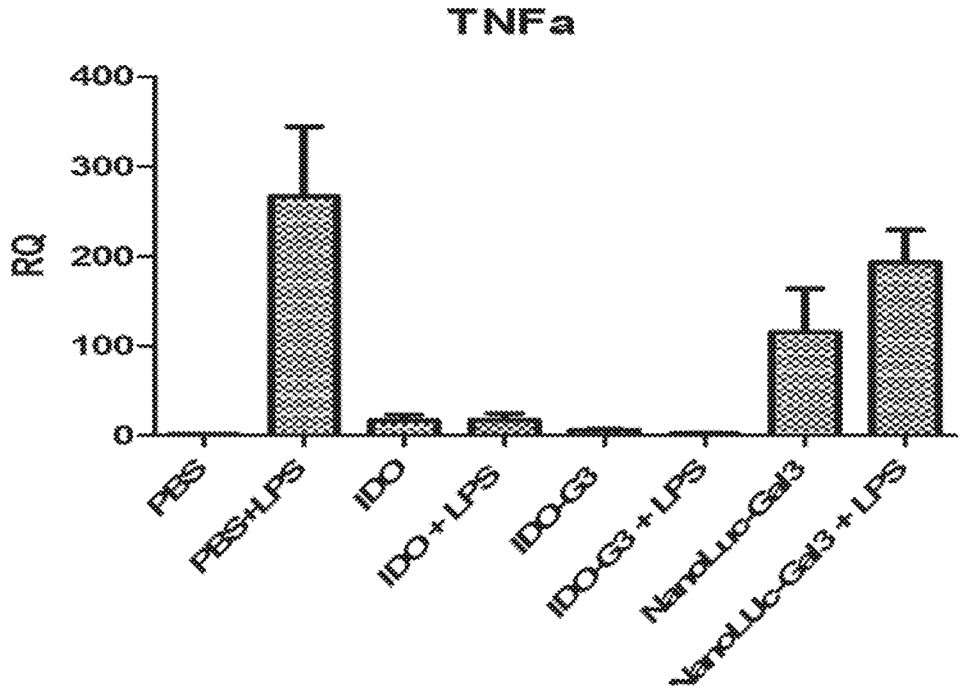
Figure 42:
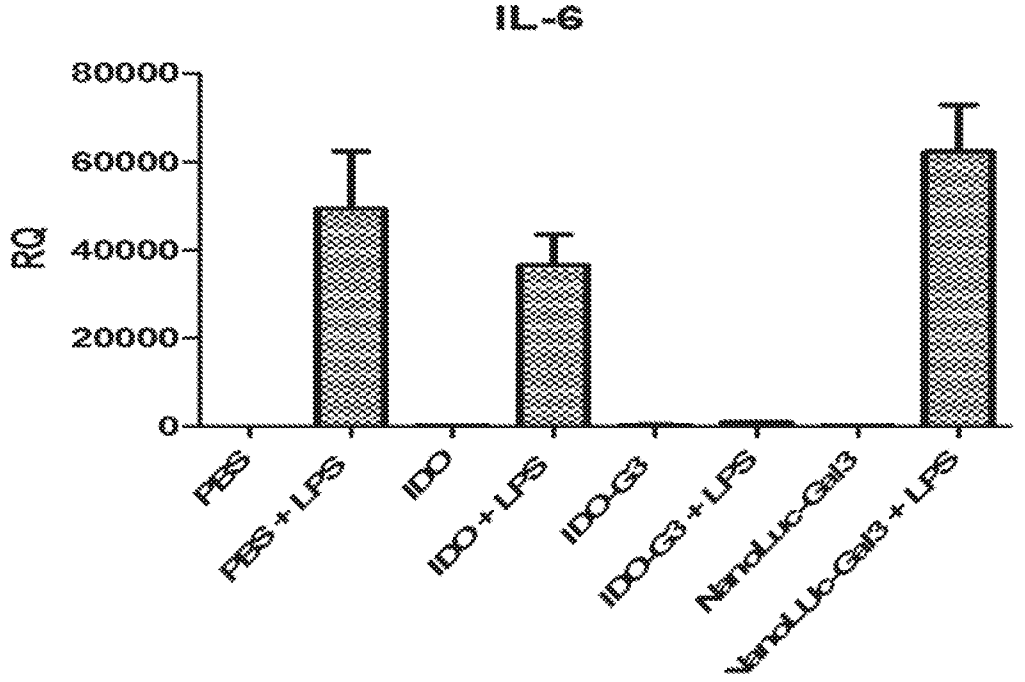

FIGS. 37-42 show graphs demonstrating IDO-Gal3 suppresses inflammatory cytokine gene expression in vivo at 24 hours. IDO-Gal3 or relevant controls were injected in the hock of C57BL/6 mice and challenged with LPS 24 hours post fusion protein administration. Two hours post LPS challenge the injection site was harvested, de-boned and its genetic profile analyzed through qPCR (as measured using the relative quantification (RQ) method). Pair-wise significant difference (by ANOVA and Tukey's post hoc) is denoted by * where $p<0.05$. FIG. 37 demonstrates RQ of IL-12p35 expression. FIG. 38 demonstrates RQ of IL-12p40. FIG. 39 demonstrates RQ of IL-1b. FIG. 40 demonstrates RQ of IFNg. FIG. 41 demonstrates RQ of TNFa. FIG. 42 demonstrates RQ of IL-6.

Figure 43:
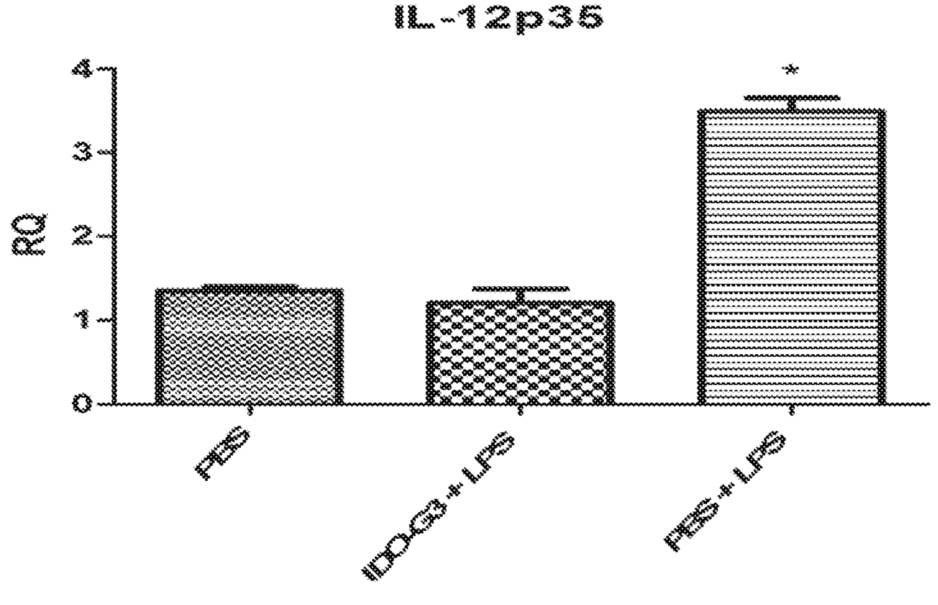
FIGS. 43-45 show graphs that can demonstrate that IDO-Gal3 suppression of inflammatory cytokine gene expression in vivo at 72 hours. IDO-Gal3 or relevant controls were injected in the hock of C57BL/6 mice and challenged with LPS 72 hours post IDO-Gal3 administration. Two hours post LPS challenge the injection site was harvested, de-boned and its genetic profile analyzed through qPCR. Pair-wise significant difference (by ANOVA and Tukey's post hoc) is denoted by * where $p<0.05$.
Figure 44:
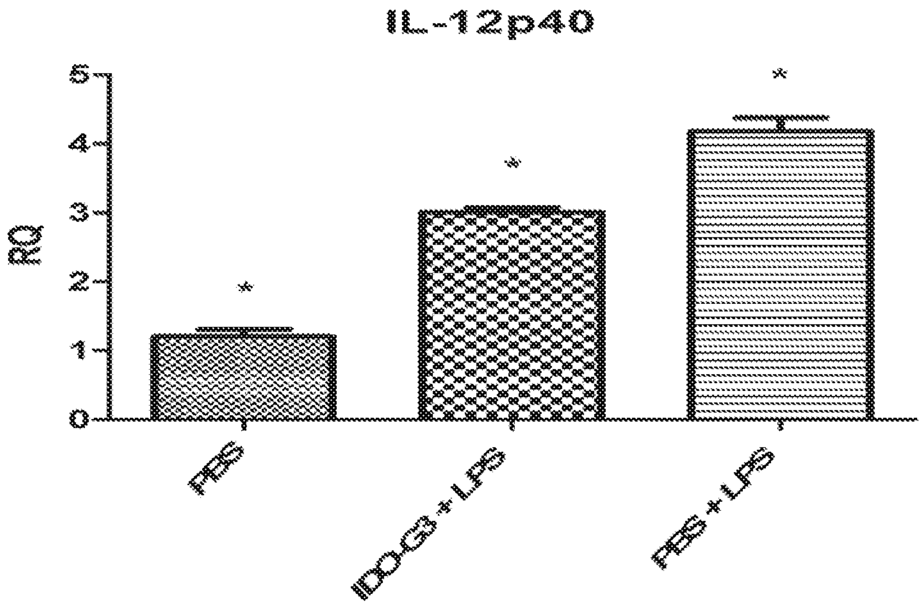
Figure 45:
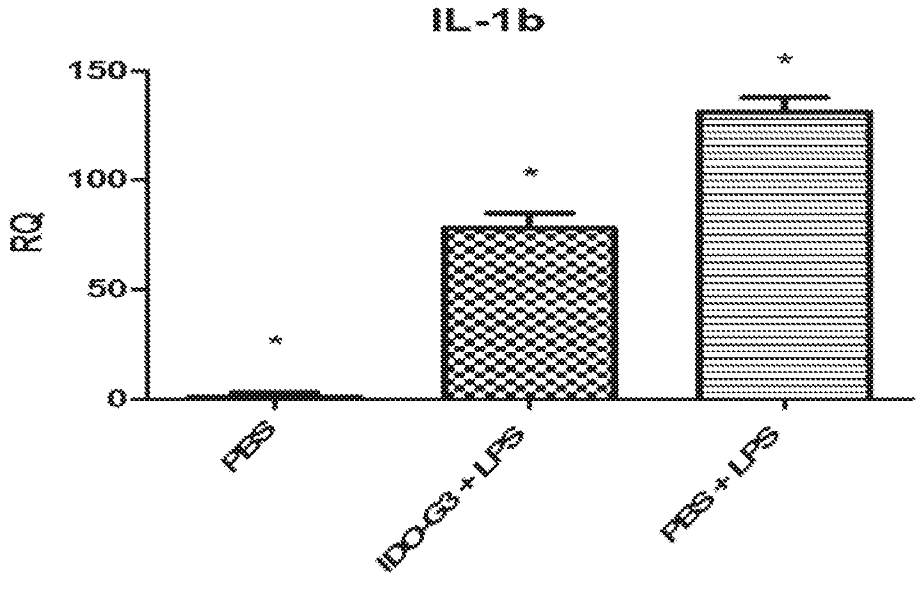
Figure 48:
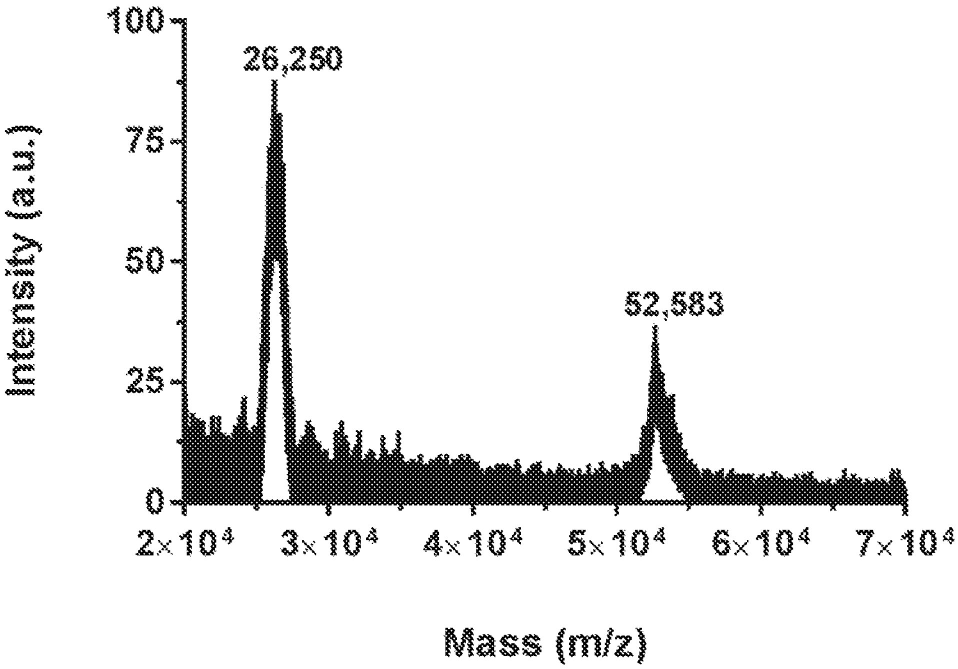
Figure 49:
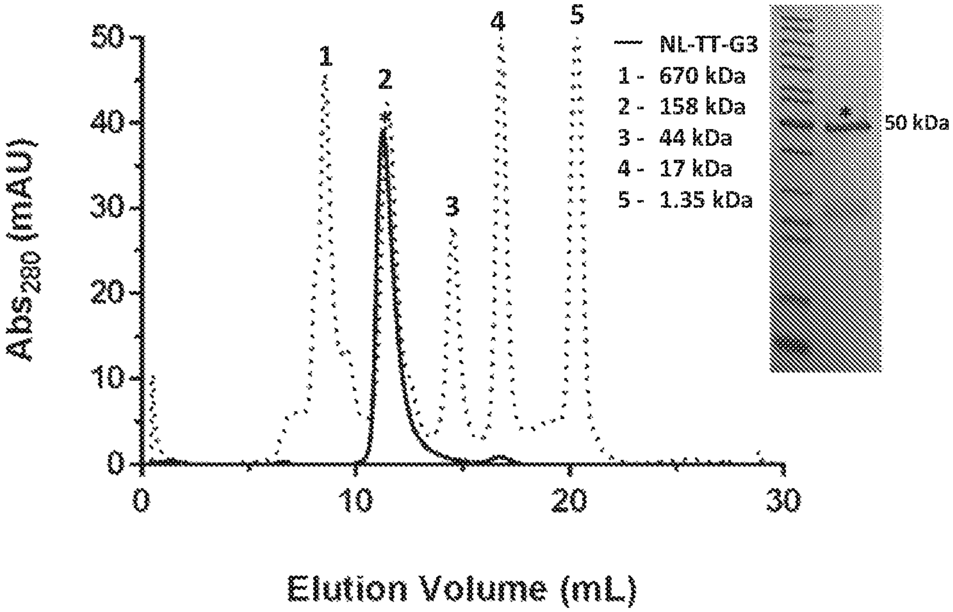
Figure 50:
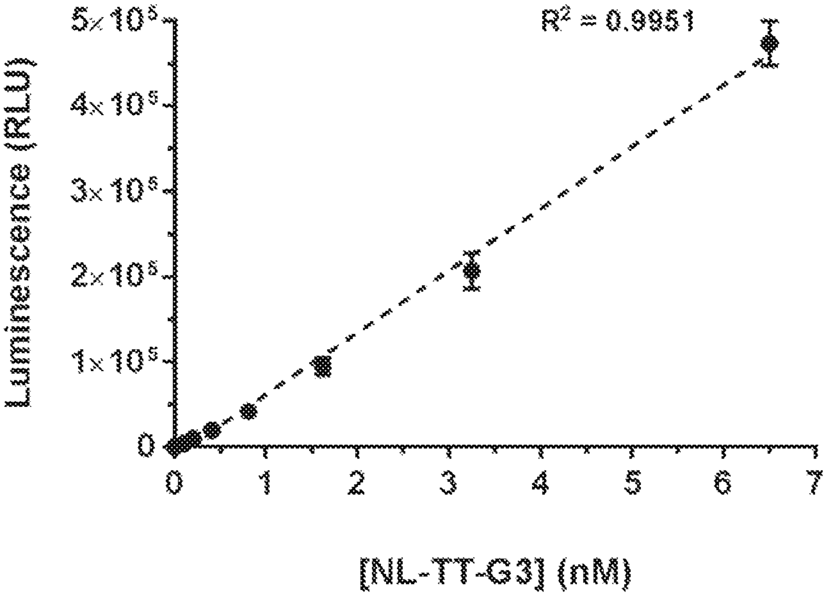
Figure 51:
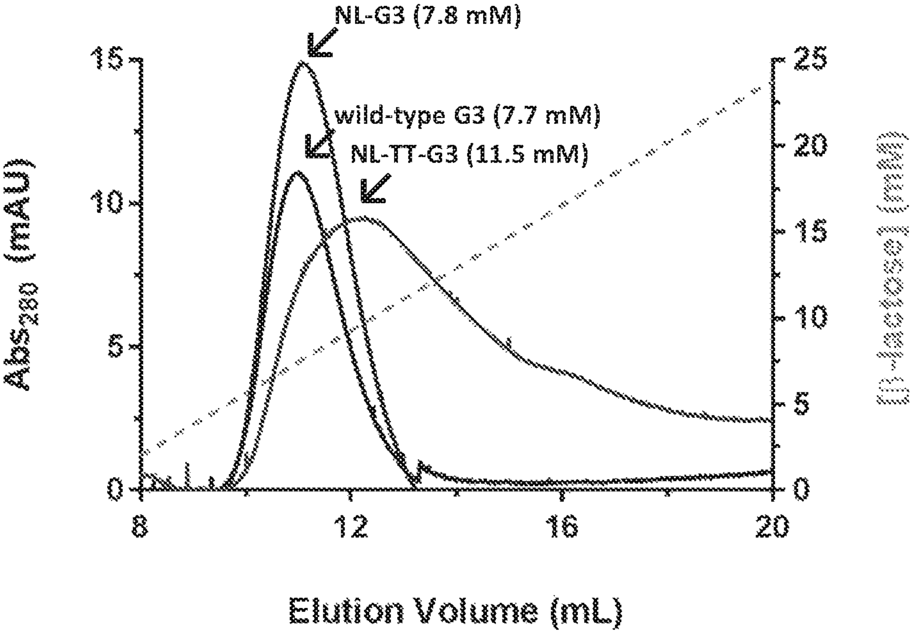
Figure 52:
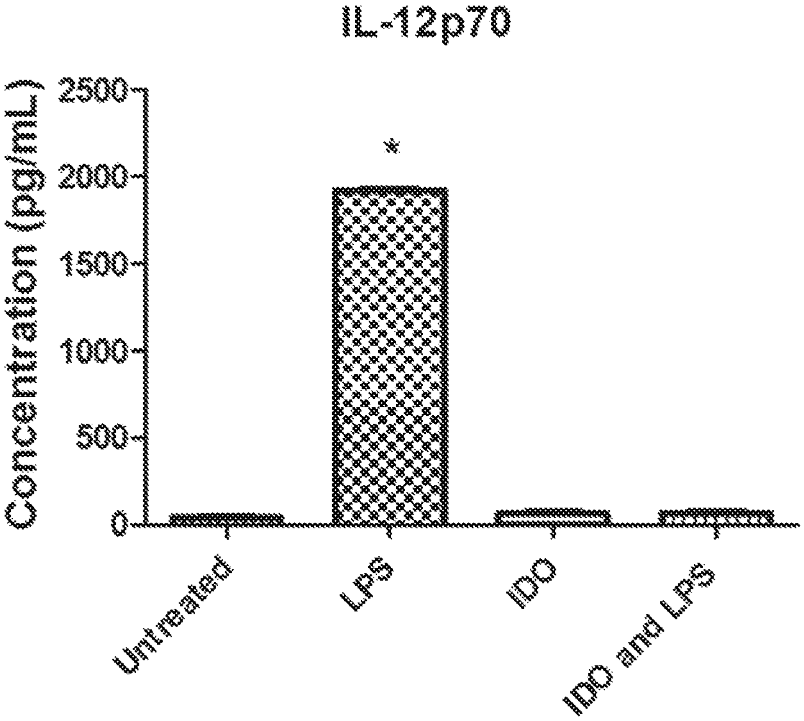
FIGS. 52-53 can demonstrate the effect(s) of IDO alone on cytokine secretion from dendritic cells (DCs). Briefly, bone marrow derived were treated with IDO for about 24 hours and challenged with lipopolysaccharide (LPS). Cytokine secretion was evaluated via ELISA and statistical significance was defined by * where $p<0.05$.
Figure 53:
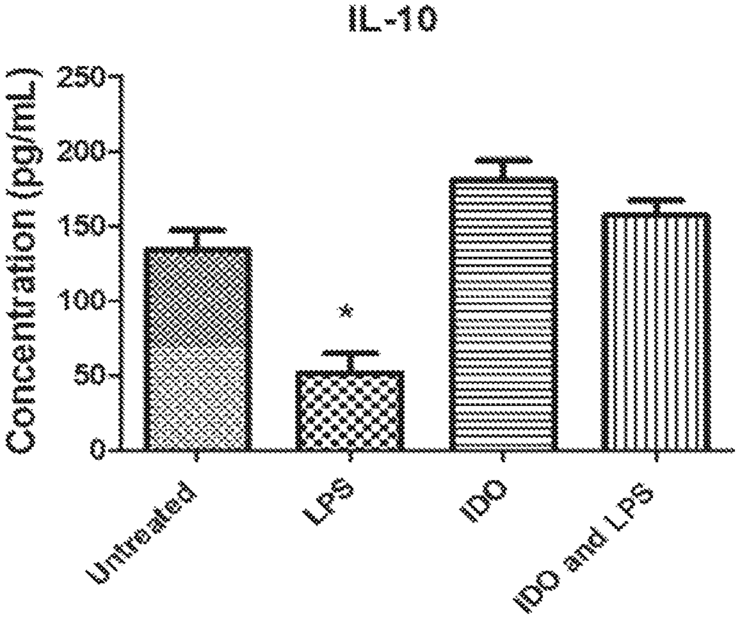
Figure 54A:
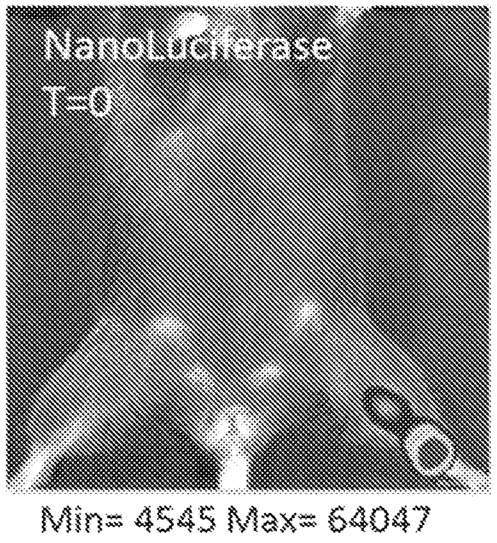
FIGS. 54A-54H show images demonstrating the luminescence at various time intervals after initial subcutaneous injections of Nanoluciferase or NanoLuc-Gal3 at the hock.
Figure 54B:
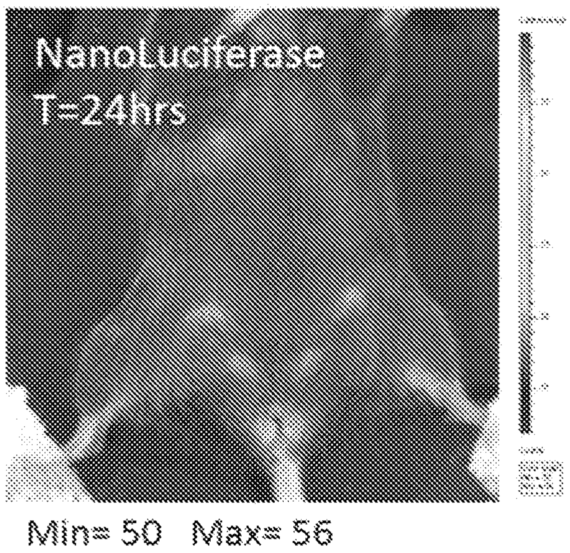
Figure 54C:
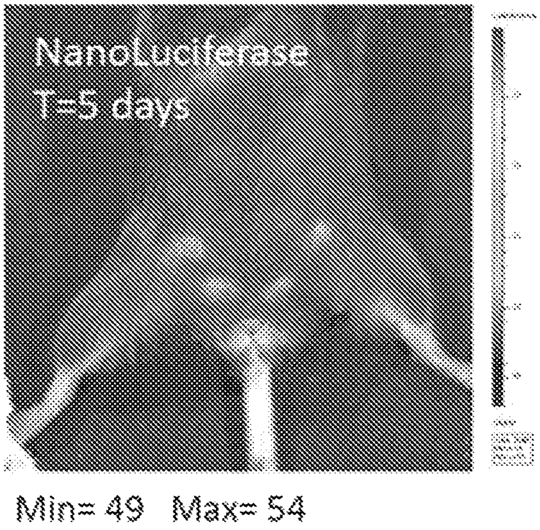
Figure 54D:
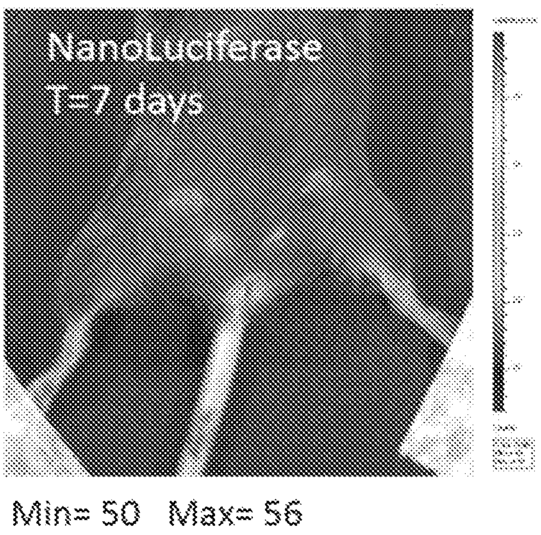
Figure 54E:
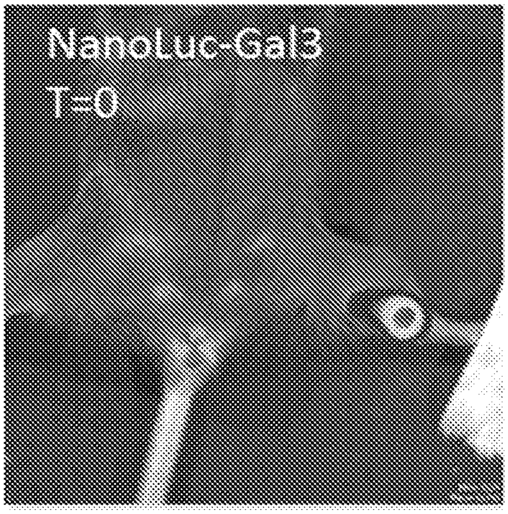
Figure 54F:
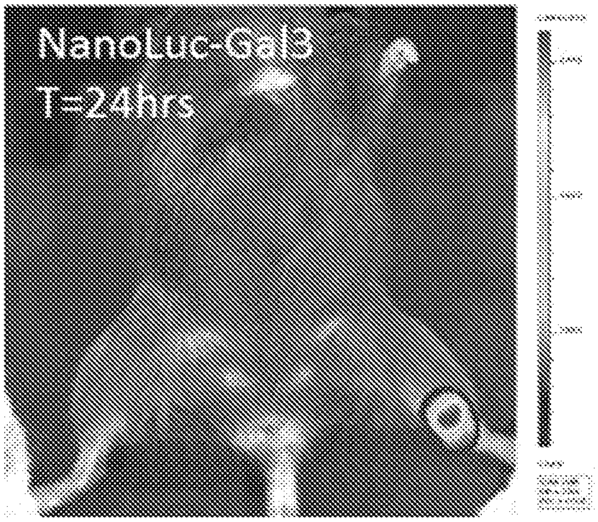
Figure 54G:
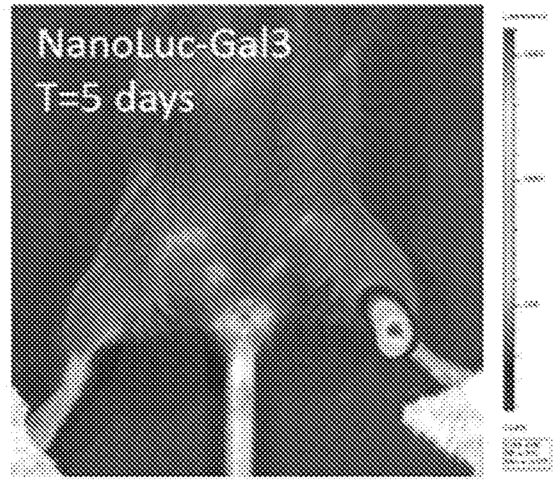
Figure 54H:
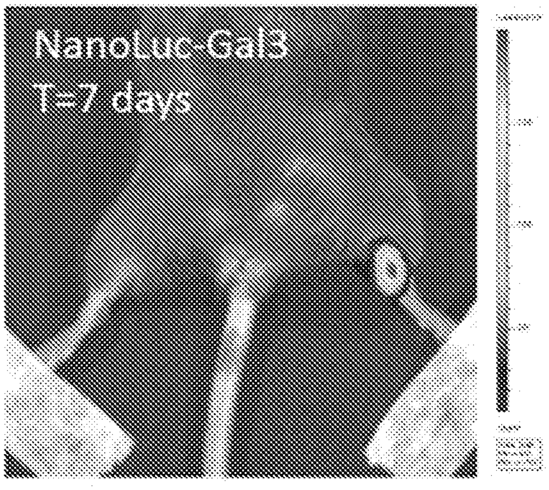
Figures 55A, 55B, 55C, 55D, 55E, 55F:
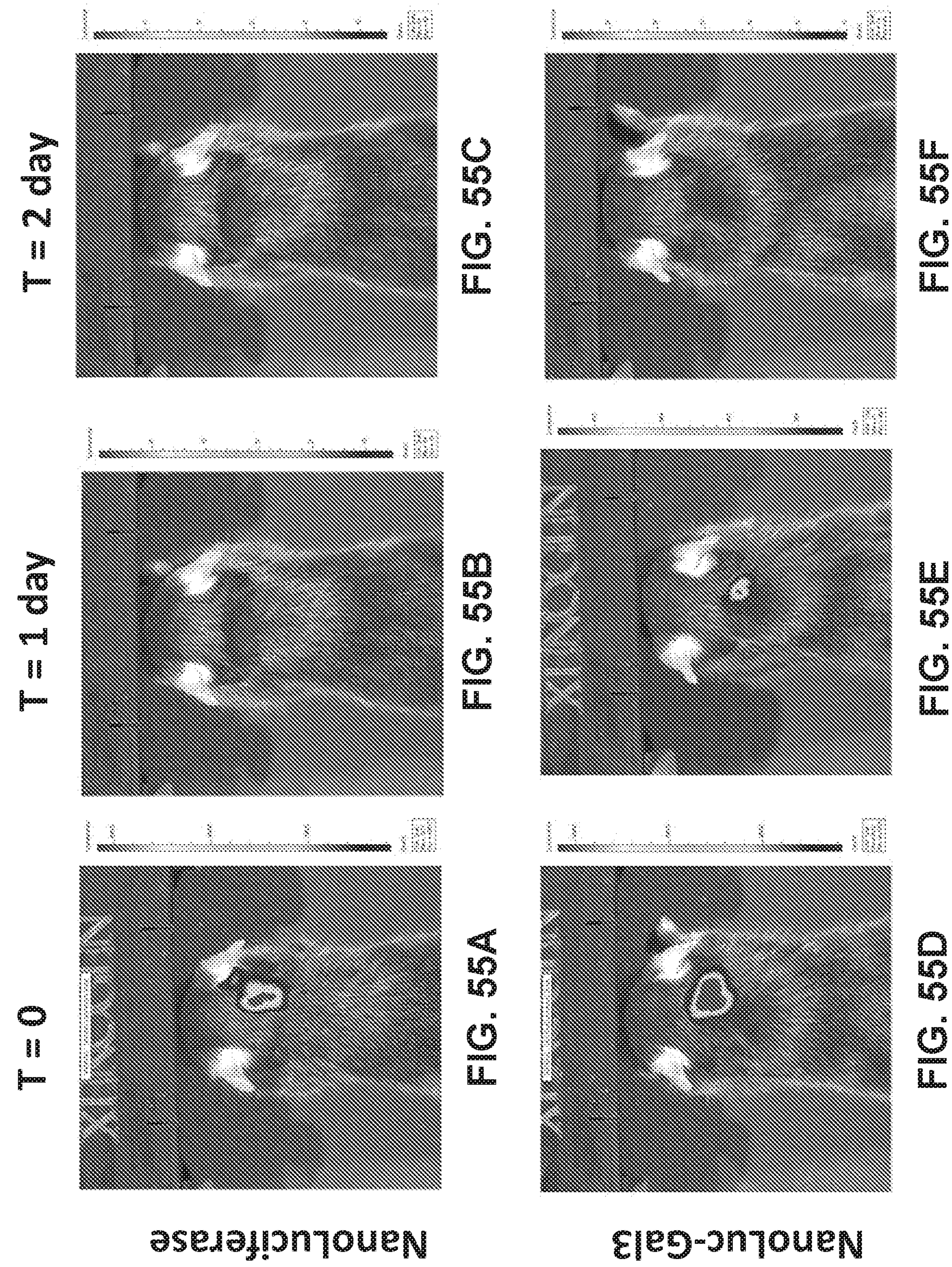
FIGS. 55A-55F show images demonstrating the luminescence at various time intervals after initial subcutaneous injections of Nanoluciferase or NanoLuc-Gal3 at the scruff.
Figure 56A:
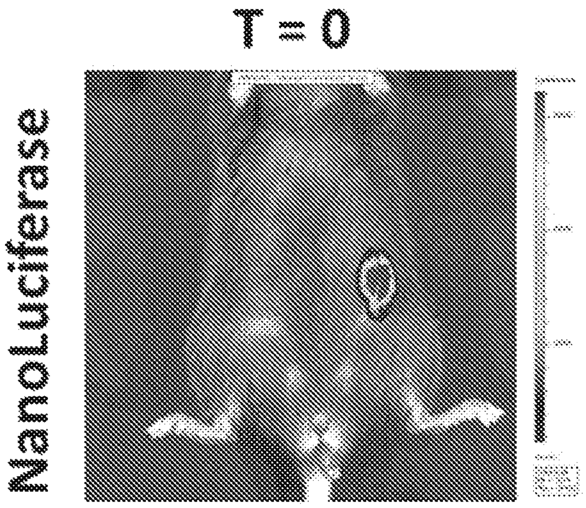
FIGS. 56A-56H show images demonstrating the luminescence at various time intervals after initial subcutaneous injections of Nanoluciferase or NanoLuc-Gal3 at the abdomen.
Figure 56B:
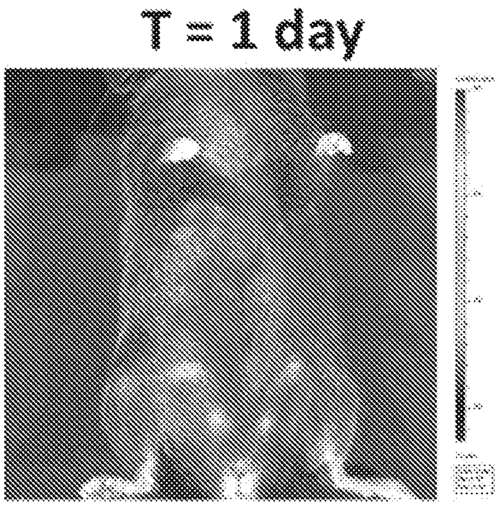
Figure 56C:
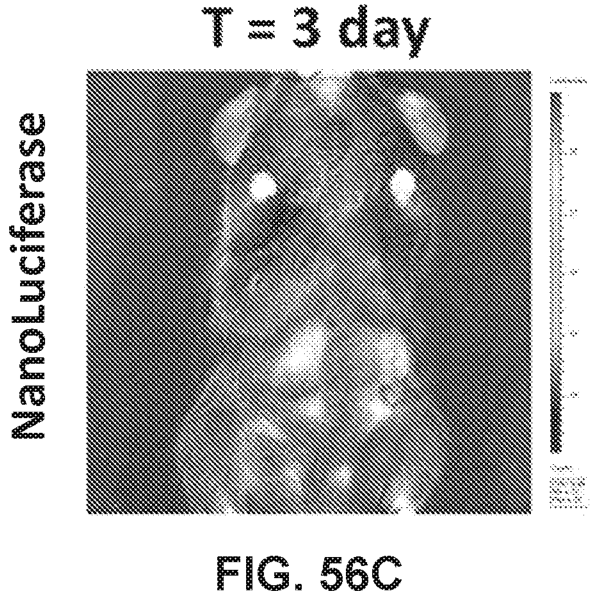
Figure 56D:
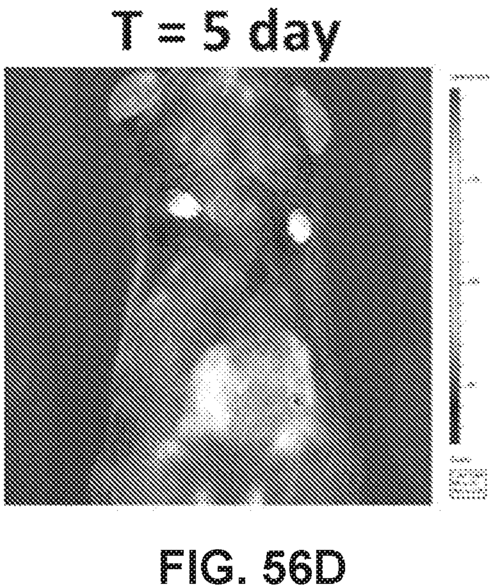
Figure 56E:
Figure 56F:
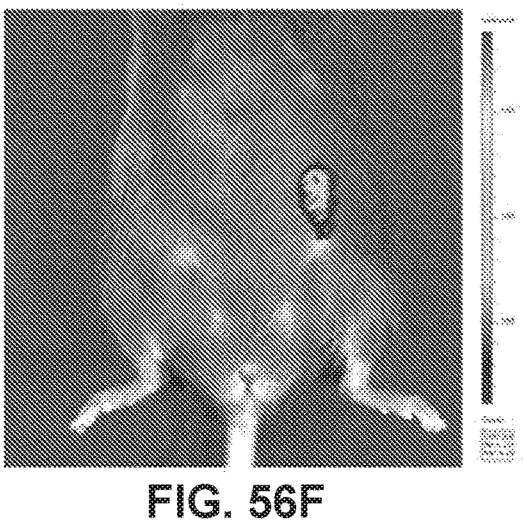
Figure 56G:
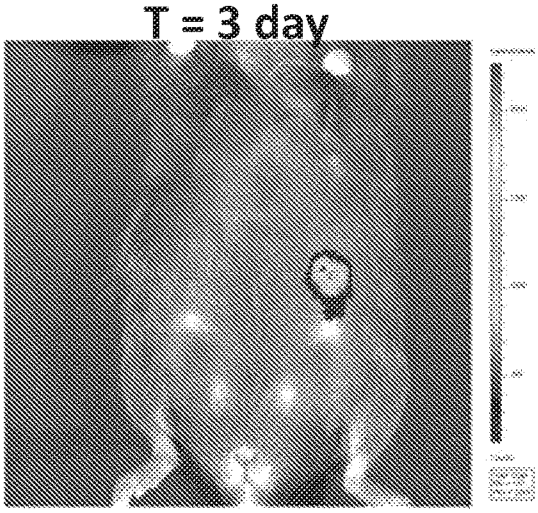
Figure 56H:
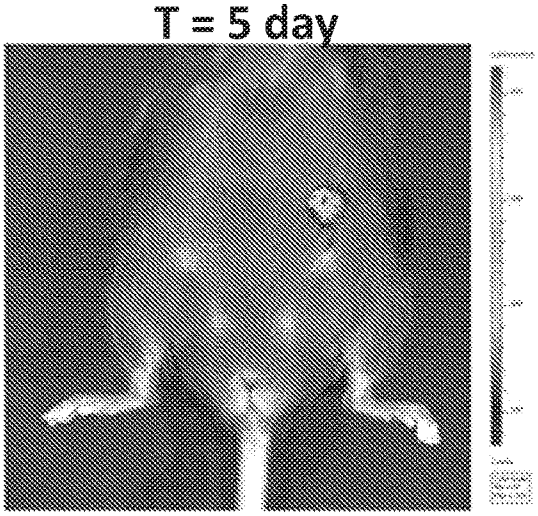

FIGS. 43-45 show graphs demonstrating IDO-Gal3 suppression of inflammatory cytokine gene expression in vivo at 72 hours. IDO-Gal3 or relevant controls were injected in the hock of C57BL/6 mice and challenged with LPS 72 hours post IDO-Gal3 administration. Two hours post LPS challenge the injection site was harvested, de-boned and its genetic profile analyzed through qPCR. Pair-wise significant difference (by ANOVA and Tukey's post hoc) is denoted by * where $p<0.05$. FIG. 43 demonstrates RQ in IL-12p35. FIG. 44 demonstrates RQ in IL-2p40. FIG. 45 demonstrates RQ in IL-1b.

FIGS. 59A-59L show images demonstrating histology of the hock after injection of IDO, IDO-G3 or a control (PBS) with and without LPS induced inflammation.

FIGS. 60A-60D show graphs demonstrating cellular infiltration (FIGS. 65A-65B) and epidermis hypertrophy (FIGS. 65C-65D) at various times post injection.

FIGS. 67A-67F shows images that can demonstrate the in vivo bioluminescence after localized injection of NL or NL-G3 into the subgingiva at various times after injection and can demonstrate retention at the site of injection.

Figure 68:
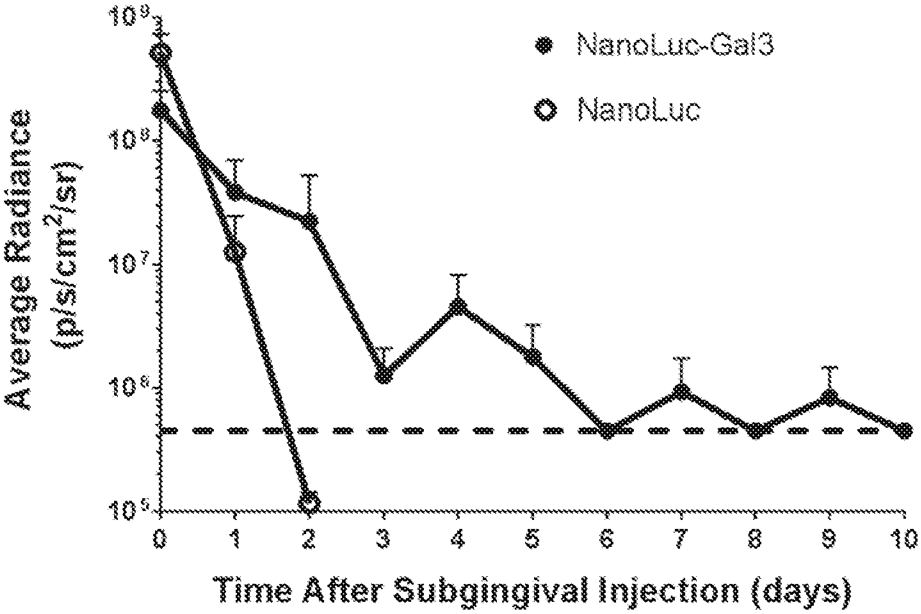
FIG. 68 shows a graph that can demonstrate the average radiance after subgingival injection of NL (NanoLuc) or NL-Gal3 (NanoLuc-Gal3).

FIG. 68 shows a graph that can demonstrate the average radiance after subgingival injection of NL (NanoLuc) or NL-Gal3 (NanoLuc-Gal3).

Figure 69:
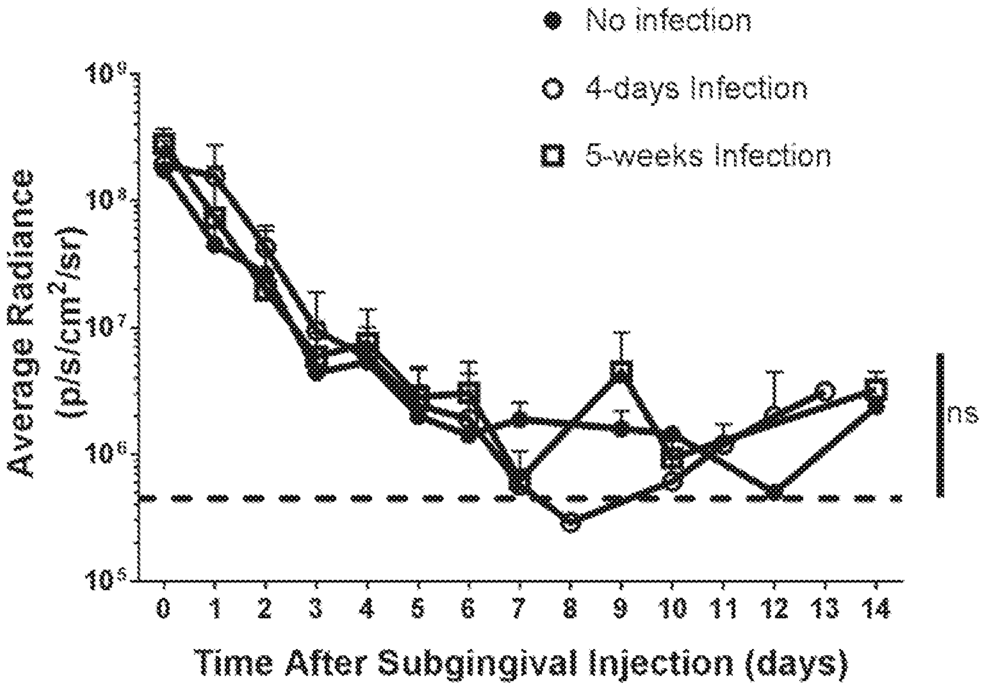
FIG. 69 shows a graph that can demonstrate the average radiance after subgingival injection of NL (NanoLuc) or NL-Gal3 (NanoLuc-Gal3) in infected and after 4 or 5 days of bacterial infection.

FIG. 69 shows a graph that can demonstrate the average radiance after subgingival injection of NL (NanoLuc) or NL-Gal3 (NanoLuc-Gal3) in infected and after 4 or 5 days of bacterial infection.

Figure 70:
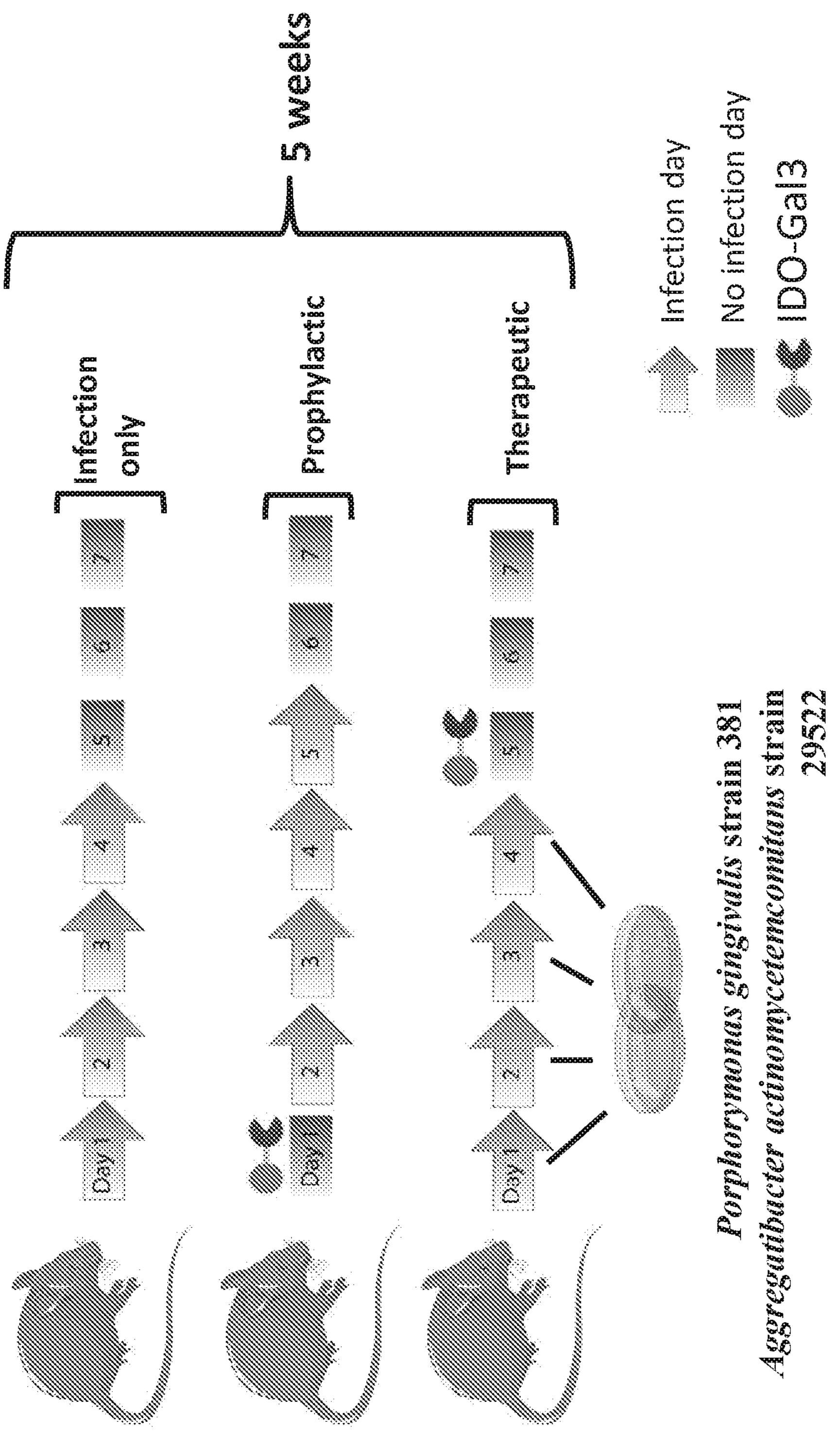
FIG. 70 shows a schematic of an experimental design and model of periodontal disease that can evaluate the effect of the various compounds and formulations thereof described herein and equivalents thereof on periodontal disease.
Figure 71:
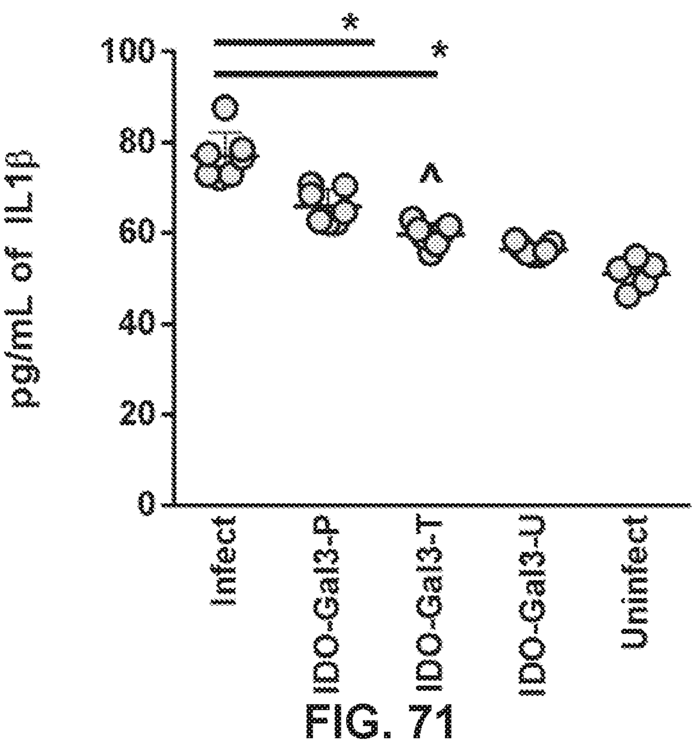
FIGS. 71-79 show graphs that can demonstrate the amount of various cytokines and other immunologically relevant compounds after subgingival injection of IDO-Gal3-P, IDO-Gal3-T, IDO-Gal3-U in a polymicrobial model of periodontal disease (see e.g.
Figure 72:
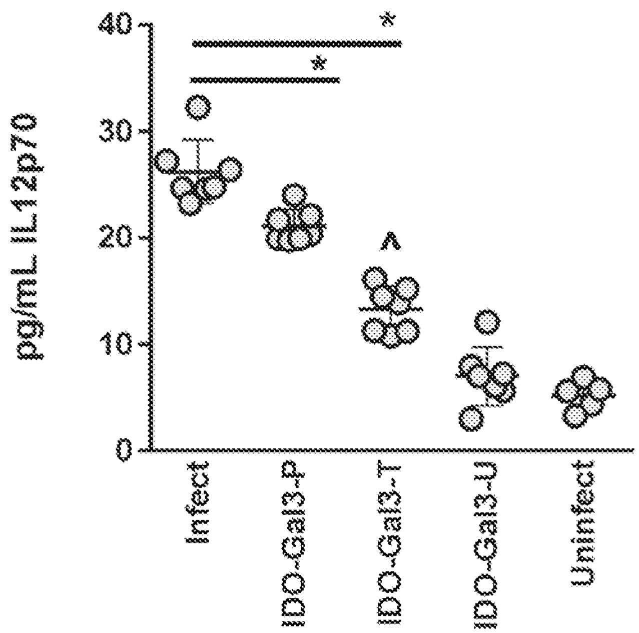
Figure 73:
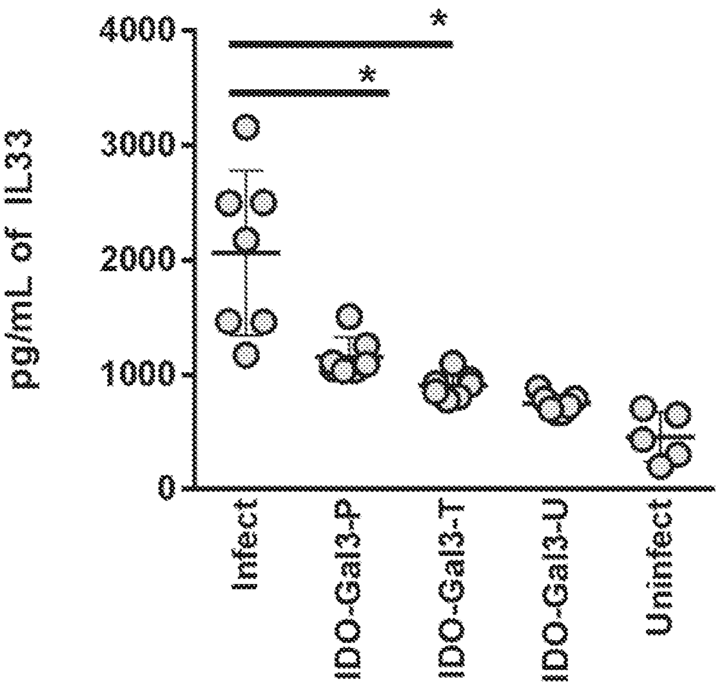
Figure 74:
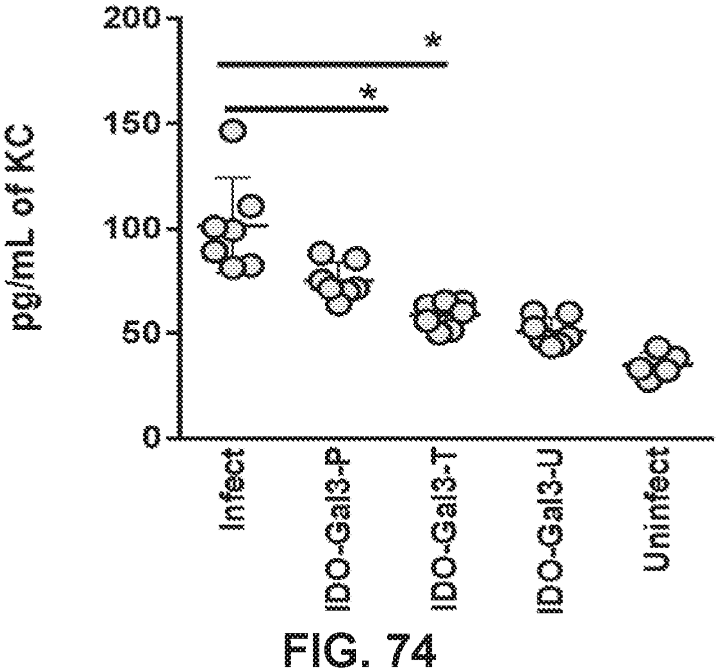
Figure 75:
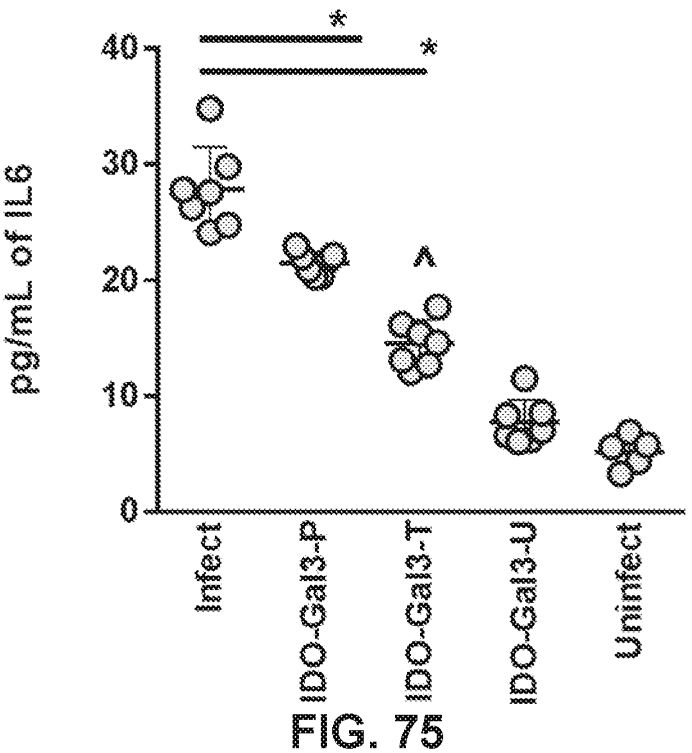
Figure 76:
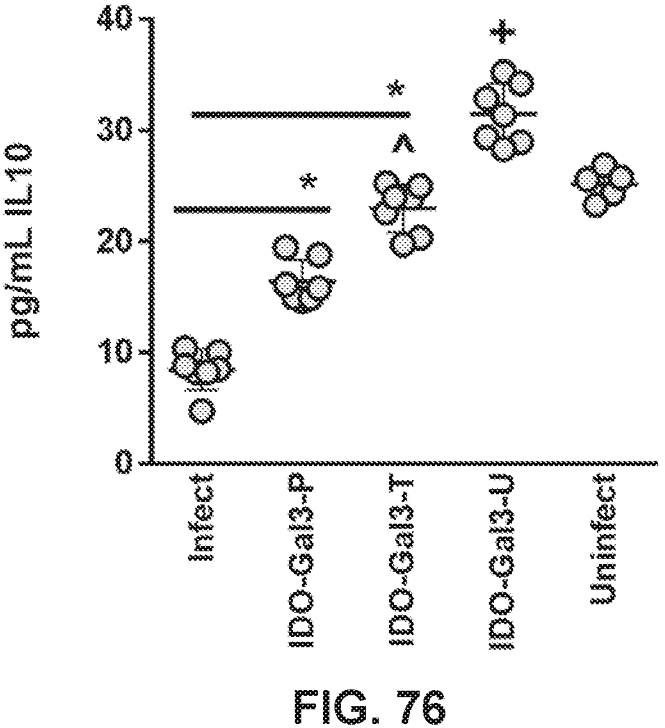
Figure 77:
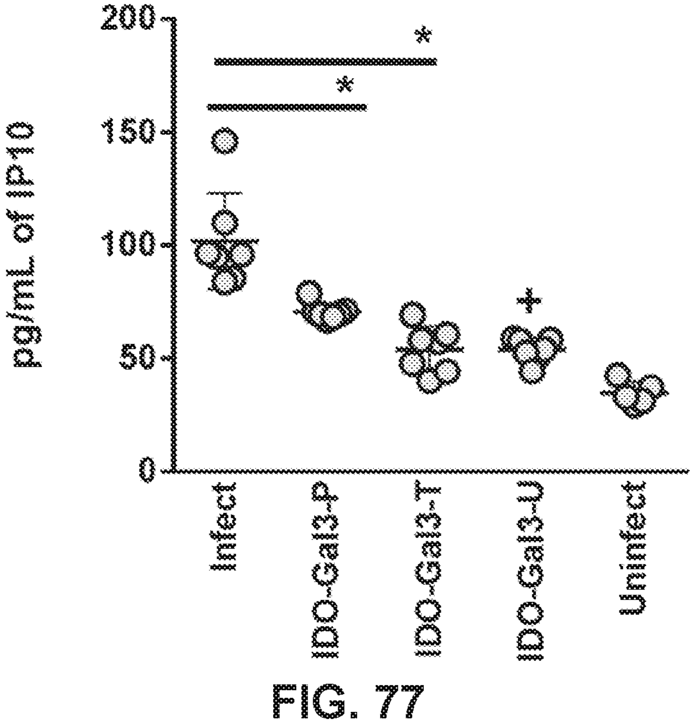
Figure 78:
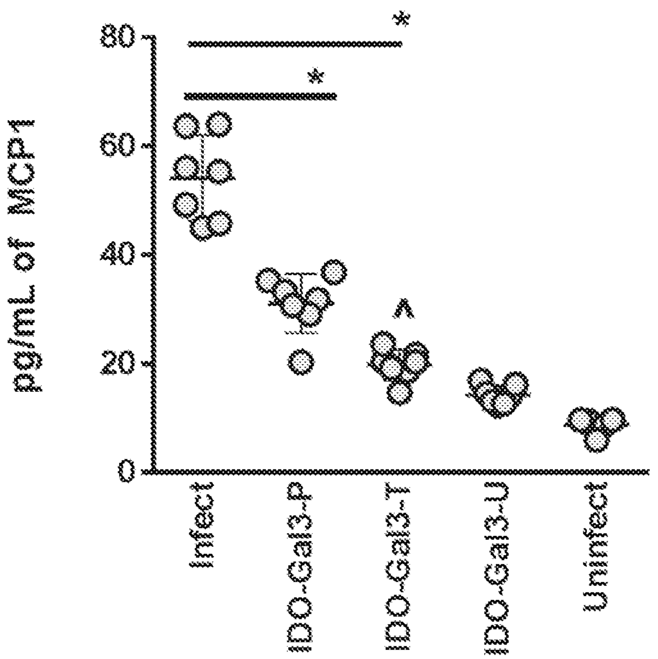

FIG. 70 shows a schematic of an experimental design and model of periodontal disease that can evaluate the effect of the various compounds and formulations thereof described herein and equivalents thereof on periodontal disease.

FIGS. 71-79 show graphs that can demonstrate the amount of various cytokines and other immunologically relevant compounds after subgingival injection of IDO-Gal3-P, IDO-Gal3-T, IDO-Gal3-U in a polymicrobial model of periodontal disease (see e.g. FIG. 77). * $p<0.05$ as indicated, A $p<0.05$ IDO-Gal3-P v. IDO-Gal3T, +$p<0.05$ IDO-Gal-3-U v. uninfected.

Example 2

FIGS. 46-51 demonstrate the design and characterization of nanoluciferase-galectin3 fusion proteins that self-assemble into multivalent structures. (FIG. 46) General design of a fusion protein of nanoluciferase (NL) and galectin-3 (G3) connected by a "self-assembling linker domain" that mediates association of fusion proteins into a structure having 3 copies of G3 and NL (referred to herein as a "homotrimeric structure"). These fusion protein assemblies are expressed and recovered from microbial hosts in the assembled state and retain the 'functional activity' of the G3 and NL domains. (FIG. 47) A monomer of NL-TT-G3 is comprised of 496 residues and estimated to have a mass of 52.7 kDa. At the N-terminus, nanoluciferase (blue) is linked by serine and glycine residues (black) to the "TriggerTrimer" (TT) sequence (green), also denoted as an alpha-helix domain. Galectin-3 (orange) is fused via a second linker to the C-terminus of TT. Furthermore, a his-tag domain (red) was incorporated at the C-terminus to allow for purification by immobilized metal-affinity chromatography (IMAC). (FIG. 48) The molecular weight of this fusion protein was verified with matrix-assisted laser desorption/ionization-time of flight (MALDI-TOF). (FIG. 49) Gel filtration chromatography reveals the molecular weight of the homotrimer NL-TT-G3 (solid line) near that of protein standard 2, gamma globulin, among the five protein standards (dashed line). Molecular weights of protein standards: 1, thyroglobulin—670 kDa; 2, gamma globulin—158 kDa; 3, ovalbumin—44 kDa; 4, myoglobin—17 kDa, 5; vitamin B12—1.35 kDa. From this elution profile, the molecular weight of NL-TT-G3 is calculated to be approximately 175 kDa. SDS-PAGE reveals a band near 50 kDa, denoted by (*), for NL-TT-G3 collected from gel filtration. (FIG. 50) Nanoluciferase remains active after purification of NL-TT-G3 via IMAC and gel filtration. (FIG. 51) NL-TT-G3 has carbohydrate-binding activity, as shown by its interaction with β-galactosides (e.g. α- and β-lactose) immobilized on affinity chromatography resin. NL-TT-G3 eluted from the affinity chromatography resin at a soluble β-lactose concentration of 11.5 mM, whereas wild-type G3 and NL-G3 ("monomeric fusion", no TT assembly domain) eluted at soluble β-lactose concentrations of 7.7 and 7.8 mM, respectively, demonstrating that NL-TT-G3 has higher carbohydrate-binding affinity than wild-type G3 and NL-G3 (green dashed line, soluble β-lactose gradient).

Figure 60A:
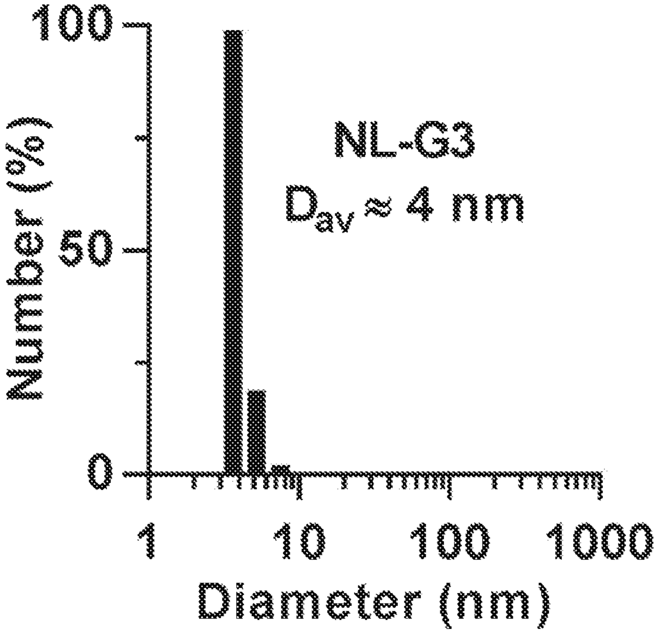
FIGS. 60A-60B show graphs that can demonstrate the dynamic light scattering results from the NL-G3 monomer (FIG. 60A) and NL-TT-G3 (FIG. 60B).
Figure 60B:
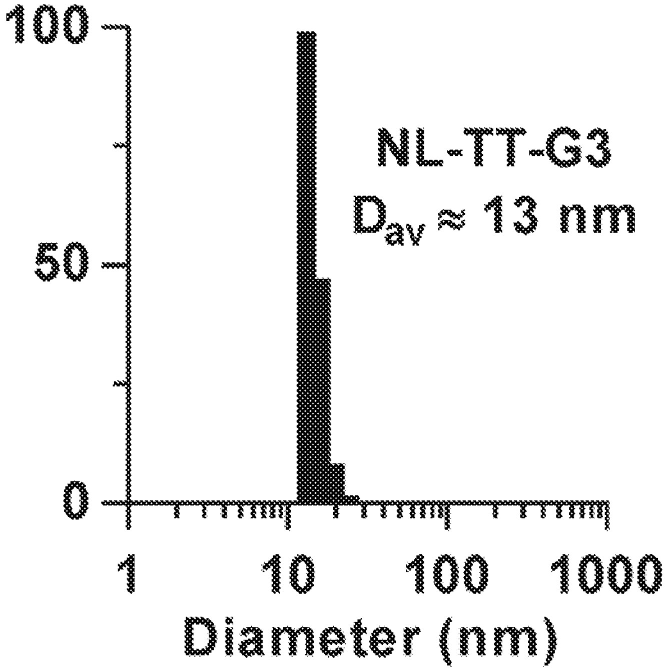

FIGS. 60A-60B show graphs that can demonstrate the dynamic light scattering results from the NL-G3 monomer (FIG. 60A) and NL-TT-G3 (FIG. 60B).

Figure 61A:
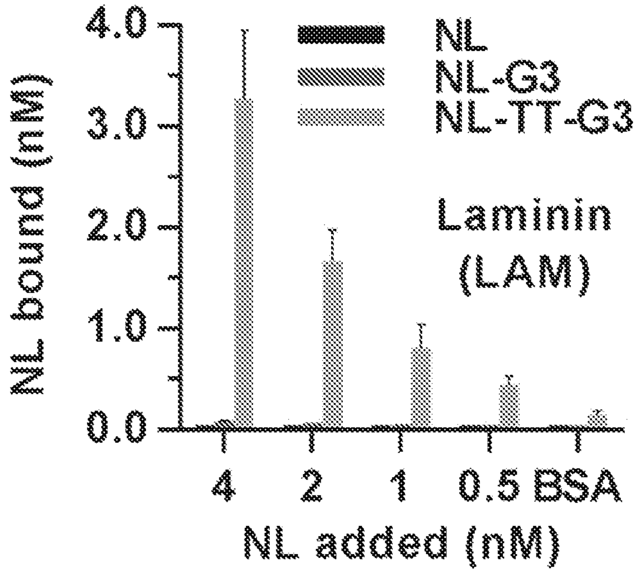
FIGS. 61A-61C show graphs that can demonstrate binding of NL, NL-G3, and NL-TT-G3 to (FIG. 61A) laminin, (FIG. 61B) alpha-2-macroglobulin, and (FIG. 61C) type-1 collagen. "BSA" denotes negative control plates coated with bovine serum albumin, which lacks Gal3-binding glycans.
Figure 61B:
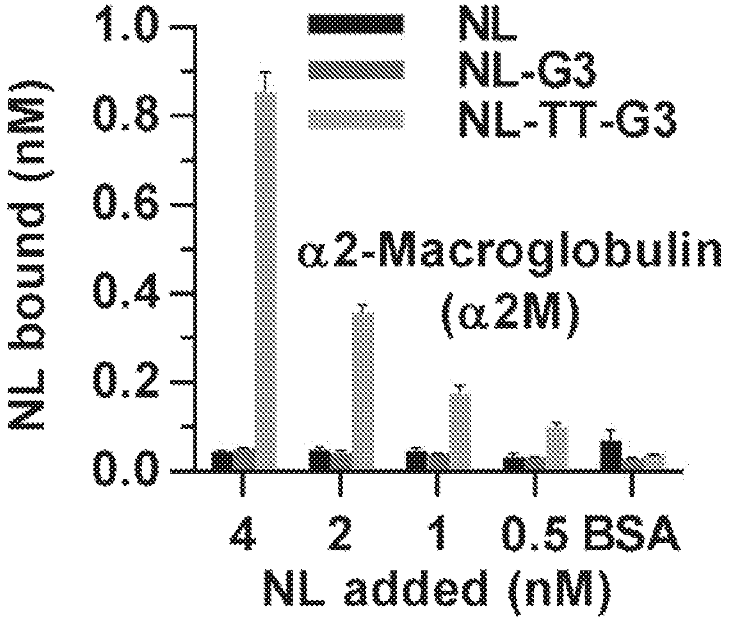
Figure 61C:
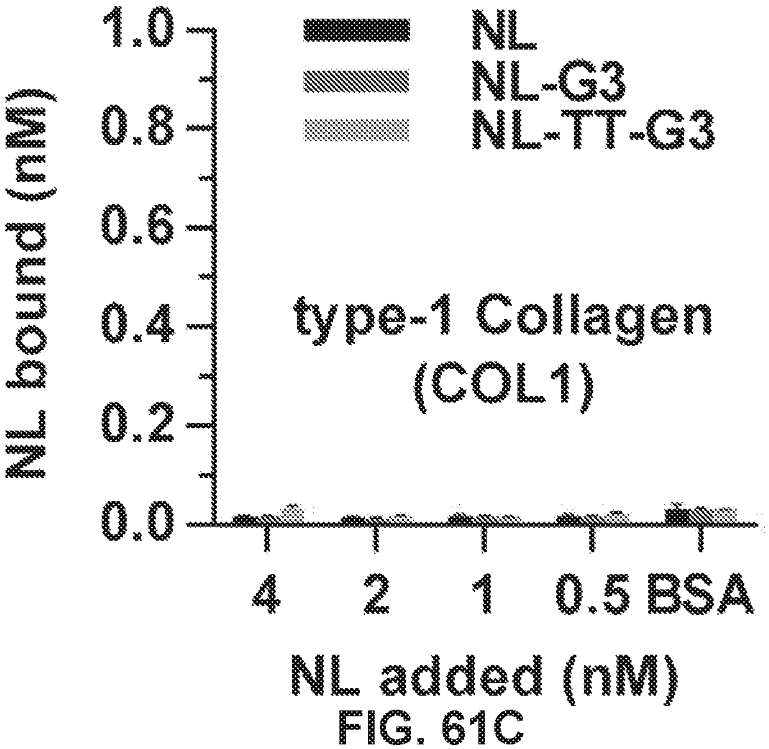

FIGS. 61A-61C show graphs that can demonstrate binding of NL, NL-G3, and NL-TT-G3 to (FIG. 61A) laminin, (FIG. 61B) alpha-2-macroglobulin, and (FIG. 61C) type-1 collagen. "BSA" denotes negative control plates coated with bovine serum albumin, which lacks Gal3-binding glycans.

Figure 62A:
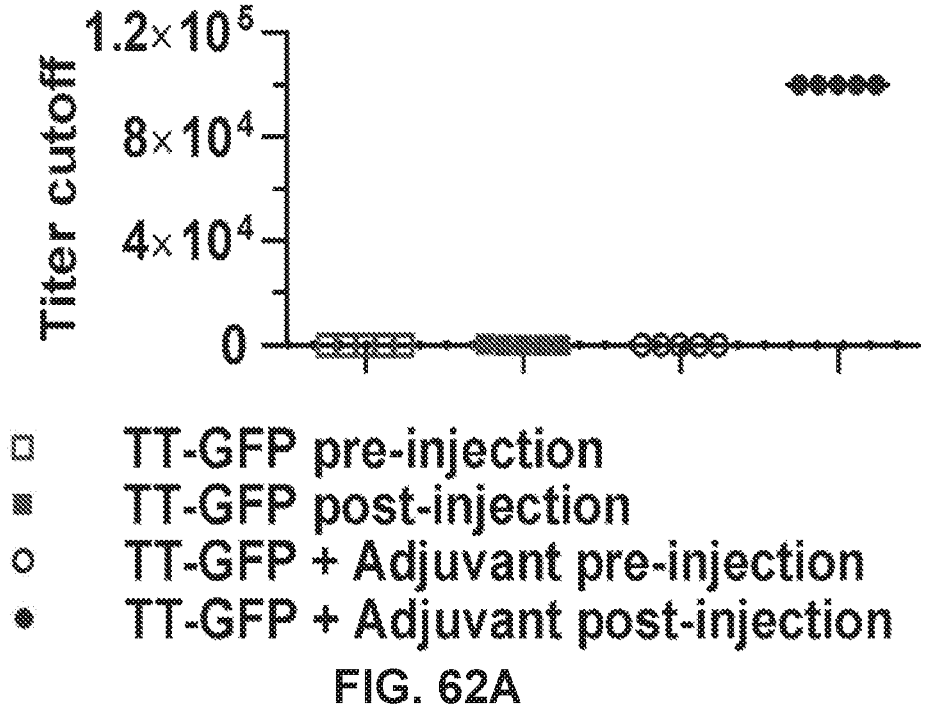
FIGS. 62A-62B show graphs that can demonstrate the generation of anti-fusion antibodies.
Figure 62B:
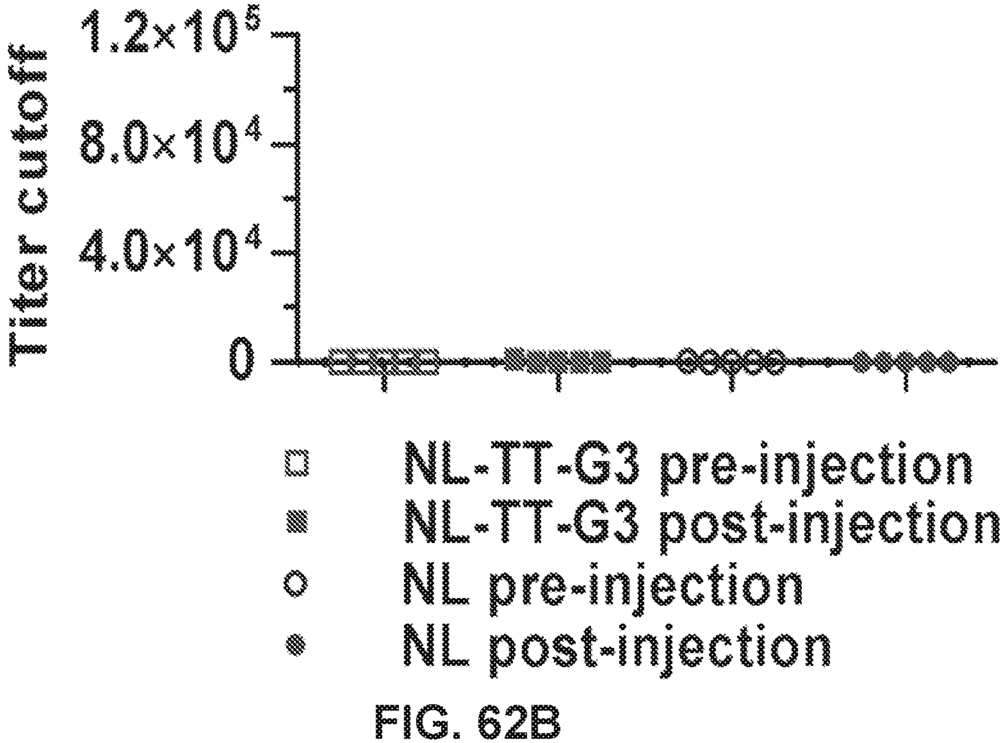

FIGS. 62A-62B show graphs that can demonstrate the generation of anti-fusion antibodies. FIG. 62A can demonstrate anti-GFP total IgG generated by C57BL/6 mice after injection of the model trimeric fusion TT-Green Fluorescent Protein (TT-GFP) in 1×PBS (red) or emulsified in TiterMax adjuvant (blue). FIG. 62B can demonstrate anti-NL-TT-Gal3 and anti-NL total IgG generated by C57BL/6 mice after injection of protein in 1×PBS. "Pre-Injection" denotes serum samples from naïve mice collected prior to injection, "post-injection" denotes serum samples from mice on day 35, after injections on days 0 and 28.

Figure 63:
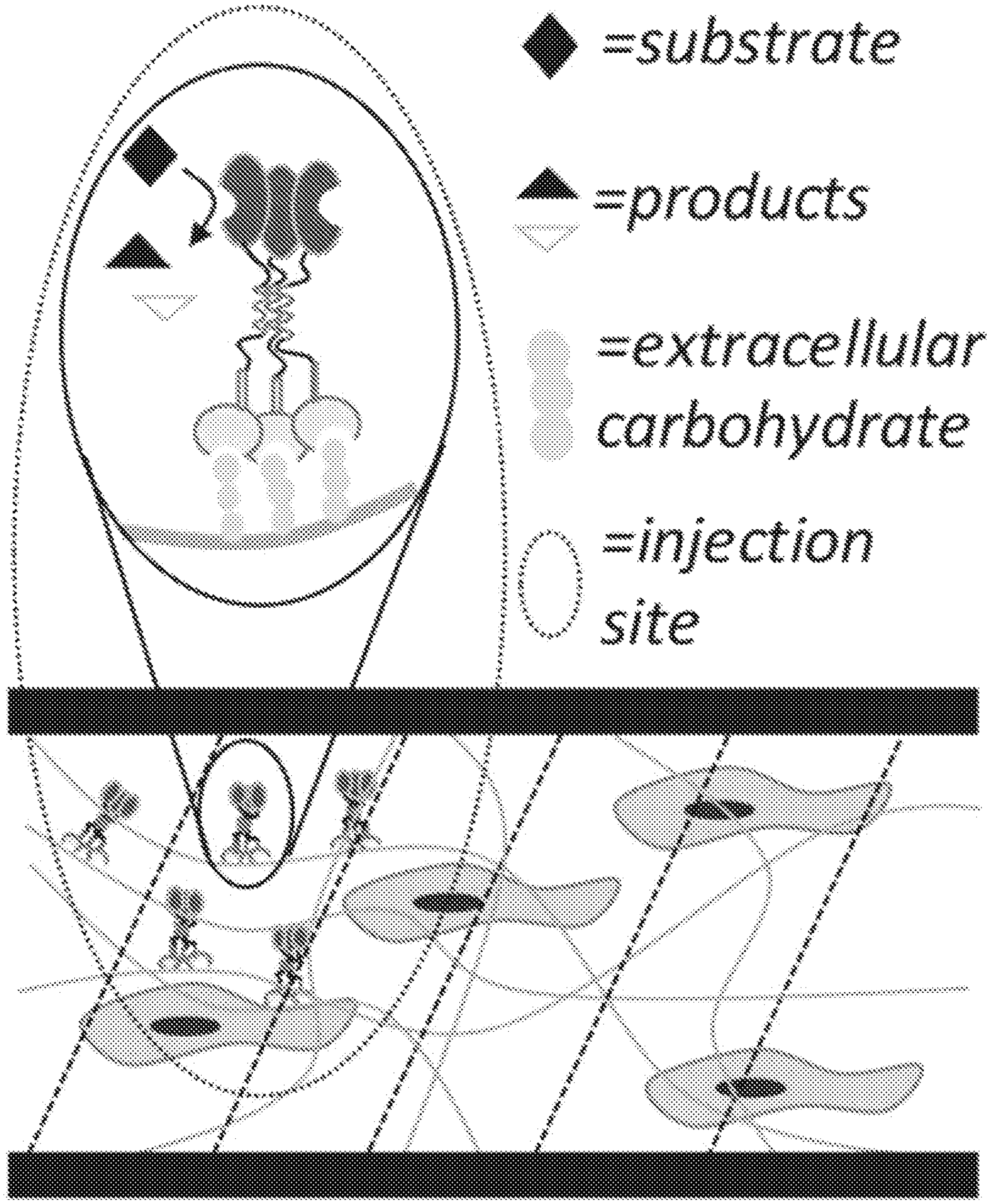
FIG. 63 shows a schematic overview of enzyme G-3 fusions retained in proximity of an injection site via binding to extracellular carbohydrates.

FIG. 63 shows a schematic overview of enzyme G-3 fusions retained in proximity of an injection site via binding to extracellular carbohydrates.

Figure 64A:
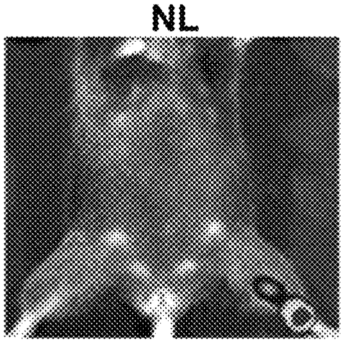
Figure 64B:
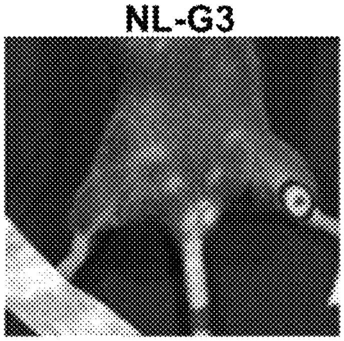
Figure 64C:
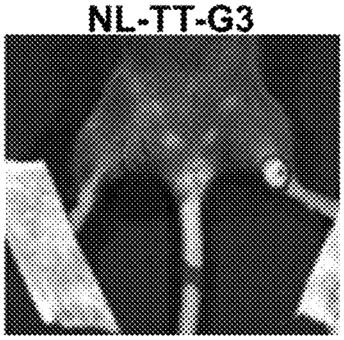
Figure 64D:
Figure 64E:
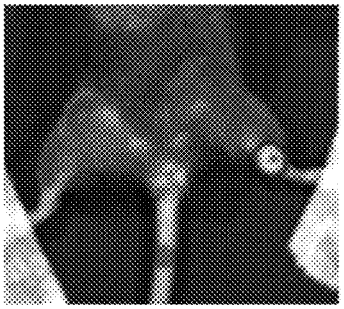
Figure 64F:
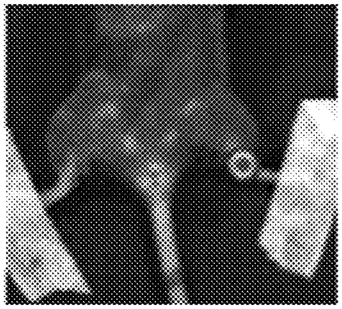
Figure 64G:
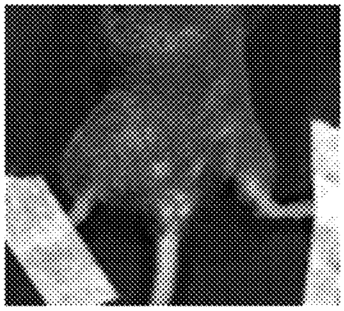
Figure 64H:
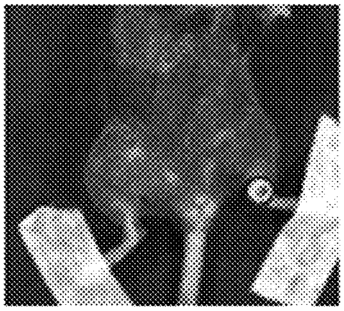
Figure 64I:
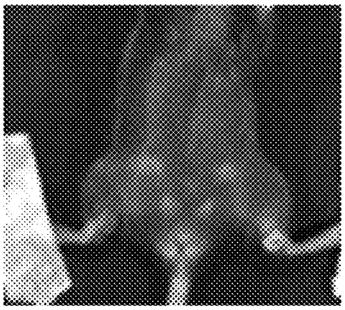

FIGS. 64A-641 show in vivo images of bioluminescence in the hock over time after local injection of NL, NL-G3, or NL-TT-G3.

Figure 65:
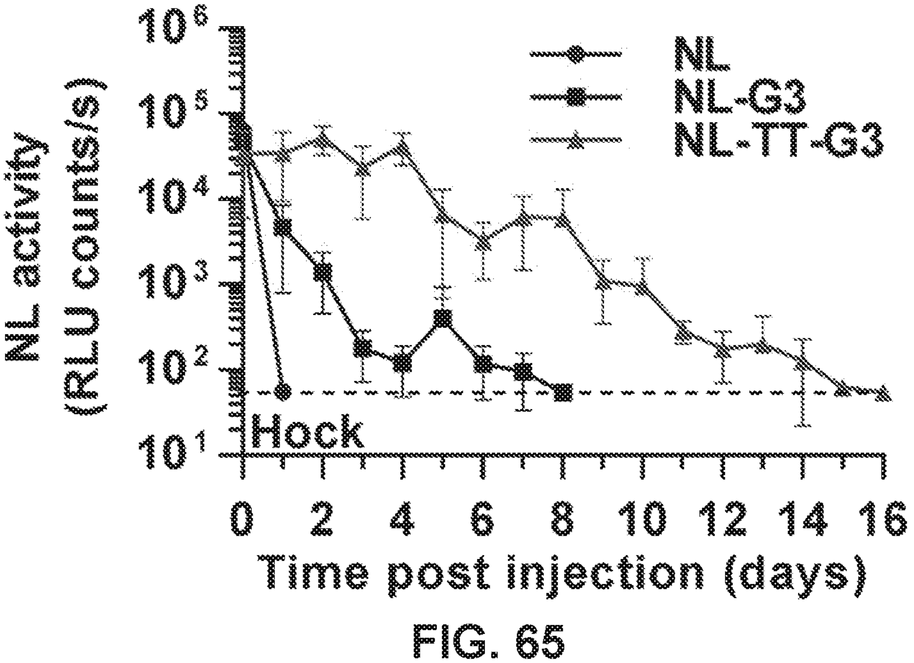
FIG. 65 shows a graph that can demonstrate local bioluminescence in the hock after local injection of NL, NL-G3, or NL-TT-G3 measured via in vivo imaging.

FIG. 65 shows a graph that can demonstrate local bioluminescence in the hock after local injection of NL, NL-G3, or NL-TT-G3 measured via in vivo imaging.

Example 3

Figures 79, 80:
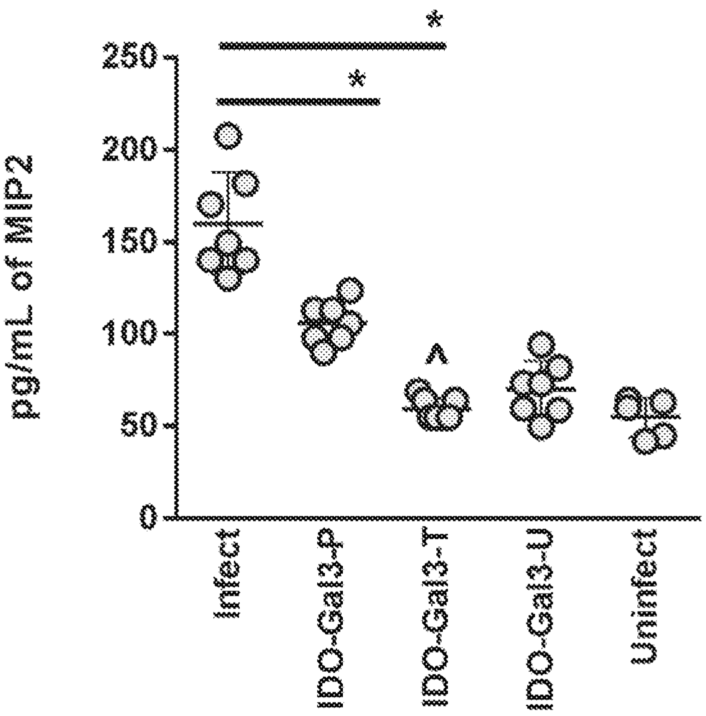
FIG. 80 shows the amino acid sequence of three peptides (CC1, CC2, and CC3) that assemble into heterotrimeric coiled-coils.

FIG. 80 shows the amino acid sequence of three peptides (CC1, CC2, and CC3) that assemble into heterotrimeric coiled-coils. FIG. 87 shows example amino acid sequence of three peptides (CC1, CC2, and CC3) that can assemble into heterotrimeric coiled-coils. The amino acid sequences of these peptides follow the canonical heptad repeat motif found in coiled-coil peptide assemblies. The heptad repeat is as follows: h-x-x-h-c-x-c which represent hydrophobic (h) and charged (c) residues. The number of heptad repeats to achieve a coiled-coil assembly is restricted to three. FIG. 87 demonstrates four heptad repeats allow the coiled-coil assembly of CC1, CC2, CC3.

Figure 81:
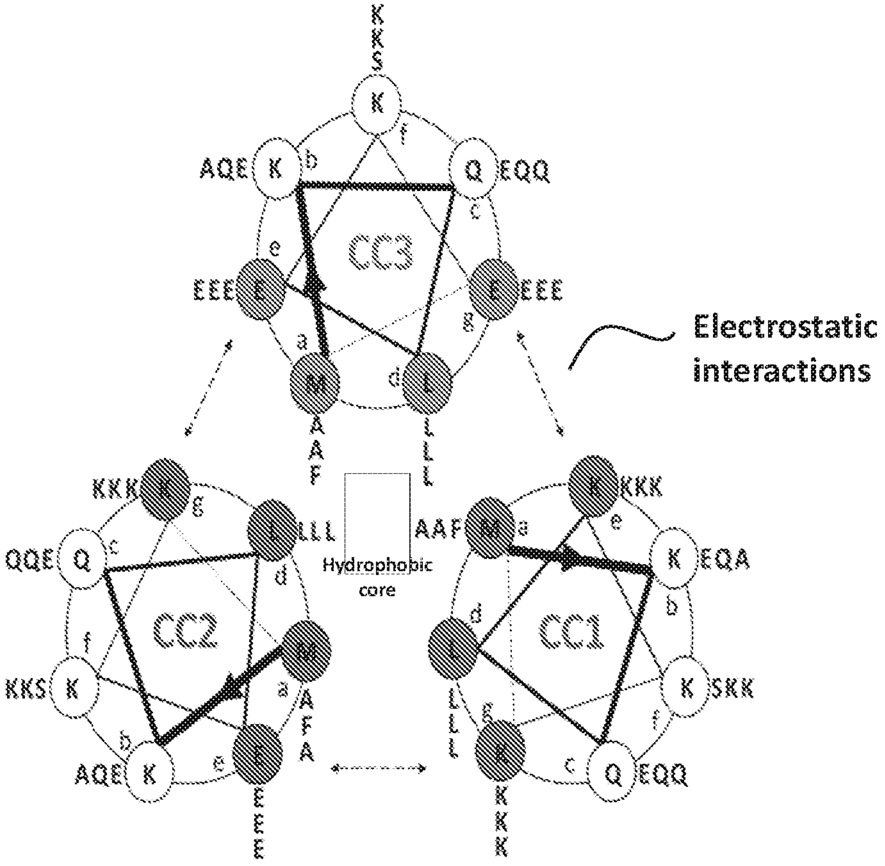
FIG. 81 shows a helical wheel diagram that illustrates the assembly of the CC1, CC2, and CC3 peptides of FIG. 80 into heterotrimeric coils.

FIG. 81 shows a helical wheel diagram that illustrates the assembly of the CC1, CC2, and CC3 peptides of FIG. 80 into heterotrimeric coils. FIG. 81 shows one embodiment of the non-covalent interactions that occurs between repeating heptads in the amino acid sequence of each peptide: CC1, CC2, and CC3.

Figure 82:
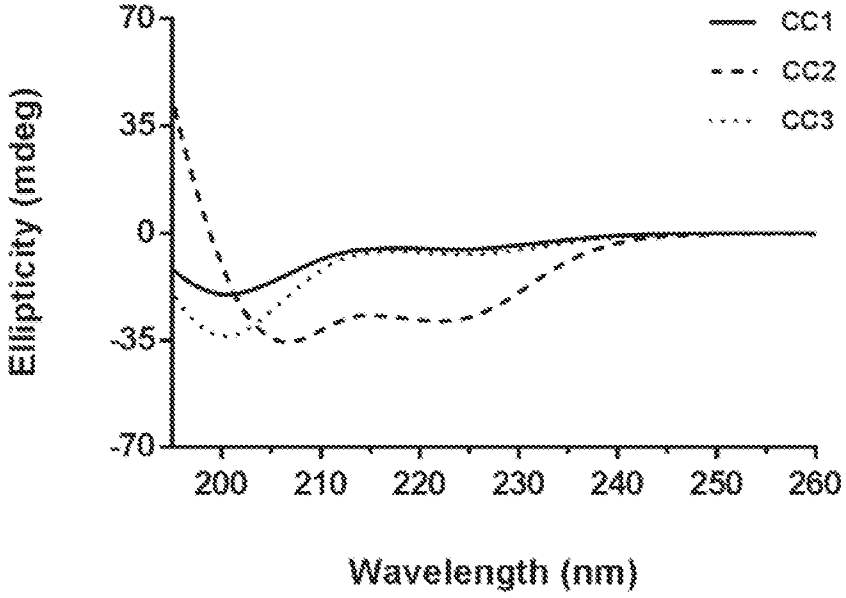
FIG. 82 shows a graph demonstrating circular dichroism data that can represent the secondary structures of CC1, CC2, and CC3 individually in aqueous solution.

FIG. 82 shows a graph demonstrating circular dichroism data that demonstrates the secondary structures of CC1, CC2, and CC3 individually in aqueous solution. CC1 and CC3 demonstrated a more random coil signature than an alpha helix. CC2 had a profile that most closely represents it as an alpha helical peptide or homodimeric coiled-coil. Peptides for CD experiments were synthesized by solid-phase peptide synthesis (CS Bio) and purified using high pressure liquid chromatography. Samples were prepared in aqueous buffer solution suitable for CD.

Figure 83:
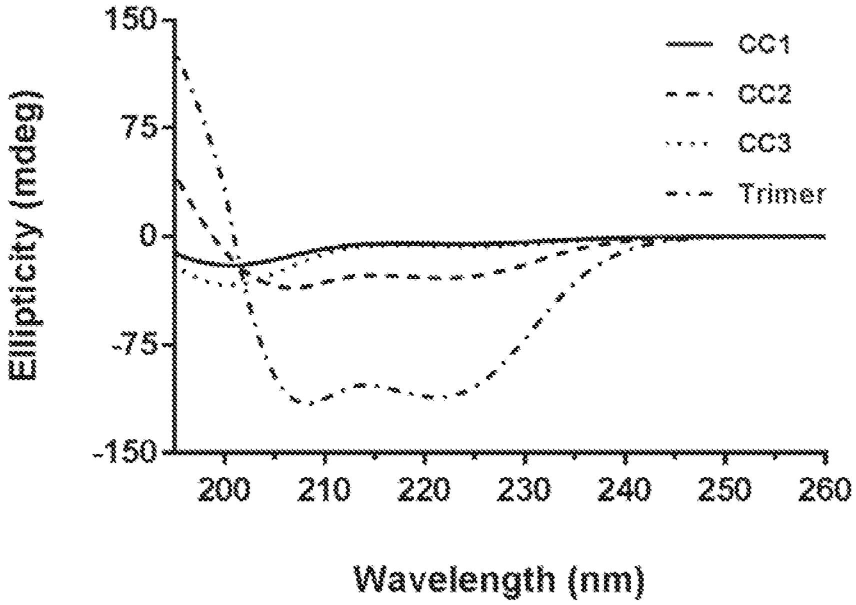
FIG. 83 shows a graph demonstrating circular dichroism data that represents the secondary structures of CC1, CC2, and CC3 individually versus combined (black trace) in aqueous solution.

FIG. 83 shows a graph demonstrating circular dichroism data that represents the secondary structures of CC1, CC2, and CC3 individually versus combined peptides in aqueous solution. The combination of CC1, CC2, and CC3 shows a very strong representation of a coiled-coil assembly that appears similar to an alpha helical secondary structure. The shift from random-coil signature of CC1 and CC3 can indicate that all three peptides are interacting to form the curve denoted as "trimer".

Figure 84:
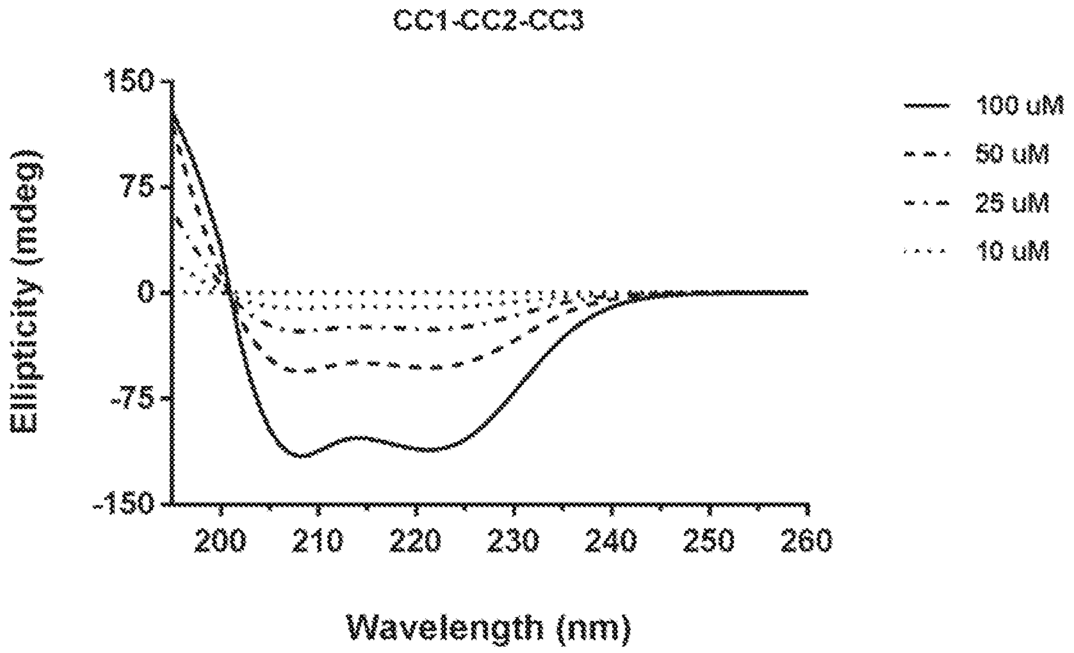
FIG. 84 shows a graph demonstrating circular dichroism data that represents the secondary structures of CC1, CC2, and CC3 combined in aqueous solution at varying concentrations.

FIG. 84 shows a graph demonstrating circular dichroism data that represents the secondary structures of CC1, CC2, and CC3 combined in aqueous solution at varying concentrations. This graph demonstrates that the combined peptides can maintain their heterotrimeric assembled state down to concentrations that are within the detection limit of CD.

Figure 85:
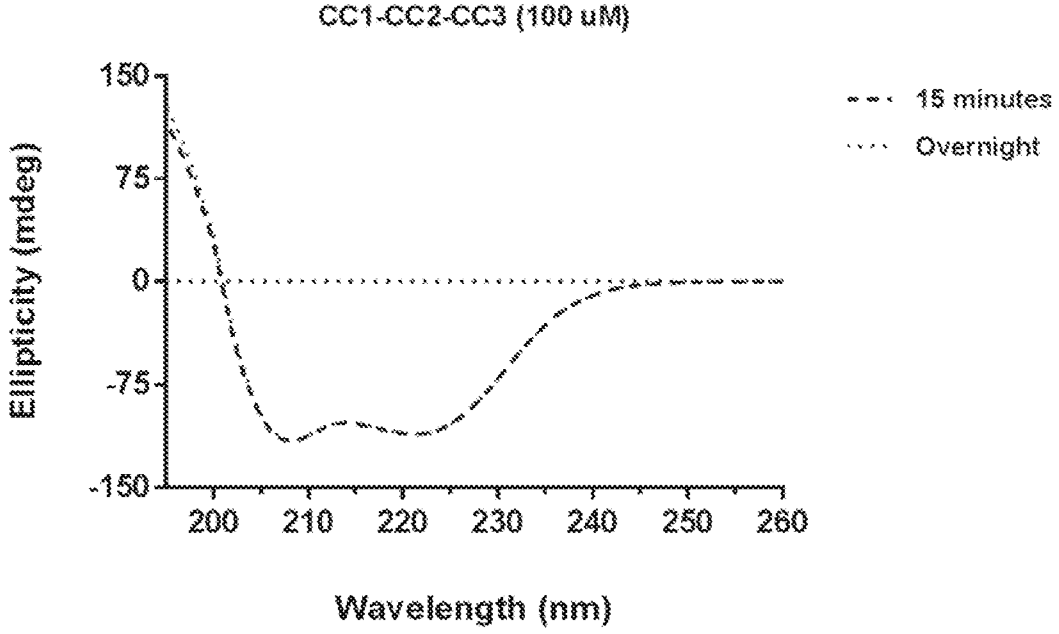
FIG. 85 shows a graph demonstrating circular dichroism data that represents the secondary structures of CC1, CC2, and CC3 combined in aqueous solution when mixed immediately or overnight.

FIG. 85 shows a graph demonstrating circular dichroism data that represents the secondary structures of CC1, CC2, and CC3 combined in aqueous solution when mixed immediately or overnight. This data shows that the formation of the CC heterotrimer can occur instantly (<about 10 min) and remains assembled for a long period of time (about 18 h) in aqueous solution.

Figure 86:
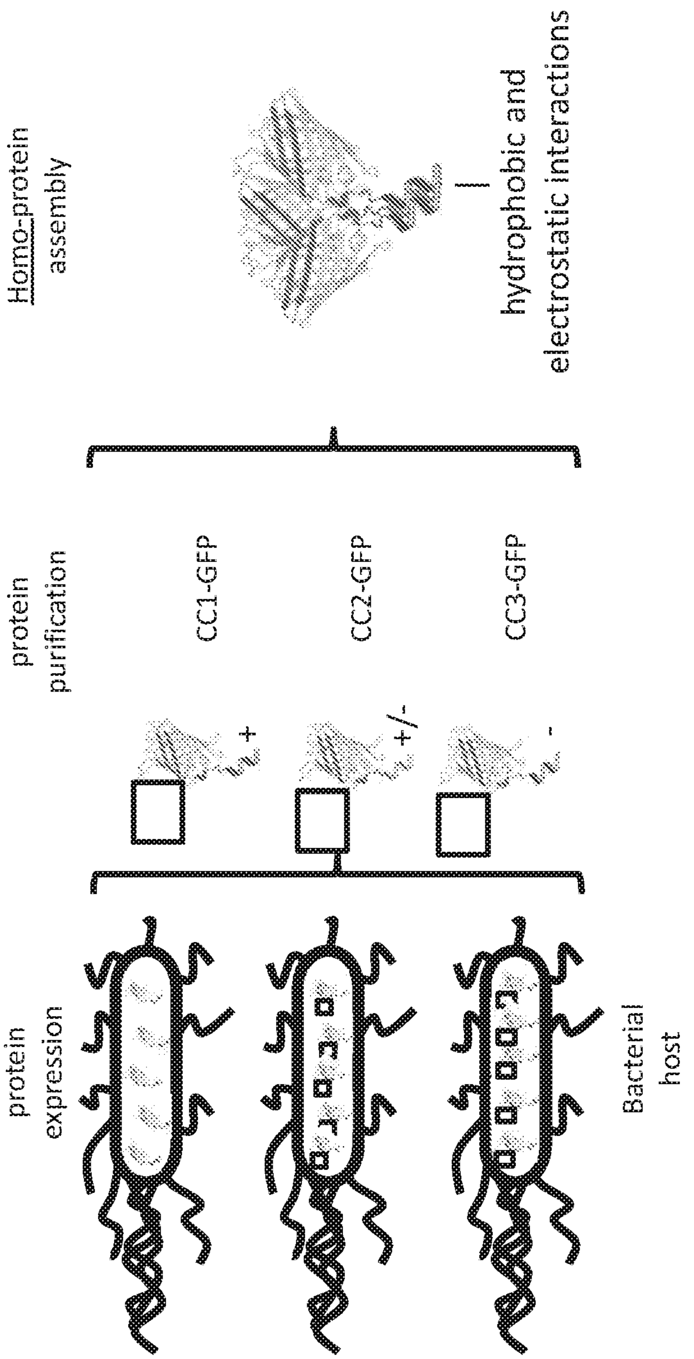
FIG. 86 shows a schematic representation of CC1, CC2, and CC3 fusion proteins expressed from bacteriological cultures, and an embodiment of a coiled-coil fusion protein assembly as provided herein.

FIG. 86 shows a schematic representation of CC1, CC2, and CC3 fusion proteins expressed from bacteriological cultures, and an embodiment of a heterotrimeric coiled-coil homomeric fusion protein assembly as provided herein. These proteins were named CC1-sfGFP, CC2-sfGFP, and CC3-sfGFP, or CC1-GFP, CC2-GFP, and CC3-GFP. Genes encoding CC fusion proteins were designed and inserted into pET-21d vectors. Recombinant plasmids were then transformed into One Shot TOP10 Chemically Competent *E. coli* (ThermoFisher) and plated on ampicillin (about 100 μg/mL) doped LB/agar plates overnight at about 37° C. Isolated colonies from the plates were selected and cultured in 5 mL LB broth with ampicillin (about 100 μg/mL) overnight in an orbital shaker at about 37° C., 225 RPM. Recombinant DNA was recovered with a plasmid miniprep kit (Qiagen) and sequenced using the Sanger method. Positive DNA sequences were then transformed into Origami B (DE3) *E. coli* Competent Cells (Novagen) and plated on ampicillin (about 100 μg/mL) and kanamycin B (about 50 μg/mL) doped LB/agar plates overnight at about 37° C. Positive clones were picked and used to inoculate 5 mL of LB broth containing ampicillin (about 100 μg/mL) and kanamycin B (about 50 μg/mL). Cultures were grown overnight at about 37° C., 225 rpm on an orbital shaker and then sub-cultured into 1 L 2×TY media (about 16 g tryptone, about 10 g yeast extract, about 5 g NaCl) with ampicillin (about 100 μg/mL) and kanamycin B (about 50 μg/mL) at about 37° C., 225 rpm in an orbital shaker until an O.D. at 600 nm=0.6-0.8 was reached. Cultures were then spiked with about 0.5 mM isopropyl β-D-1-thiogalactopyranoside and incubated for about 18 h in an orbital shaker at about 18° C., 225 rpm. Bacteria were washed three times with 1×PBS via centrifugation (24,600×g at about 4° C. for 10 min) and then lysed with B-PER bacterial protein extraction reagent, 1 Pierce protease inhibitor tablet, 2,400 units/mL DNAse I, and about 50 mg/mL lysozyme (ThermoFisher) for about 20 min. Lysate was centrifuged at 47,700×g for about 15 min at about 4° C. to remove insoluble material, and the supernatant was collected by decanting. His-tagged proteins were recovered from the soluble fraction via metal ion affinity chromatography using HisTrap FF Crude Prepacked Columns (GE Healthcare). Purified CC fusion proteins were mixed together at equimolar concentrations and allowed to assemble into heterotrimers at about 4° C. overnight.

FIGS. 87A-87C shows the amino acid sequences of the CC fusion proteins. The C-terminus of CC1, CC2, or CC3 is linked by serine and glycine residues to the green fluorescent protein variant, sfGFP, at its N-terminus. Histidines were incorporated at the C-terminus of fused protein to allow for purification by immobilized metal-affinity chromatography.

FIG. 88 shows an SDS-PAGE analysis of CC fusion proteins appearing relatively close to their theoretical molecular weights which are 33, 34, and 33-kDa for CC1, CC2, and CC3-sfGFP, respectively.

Figure 89:
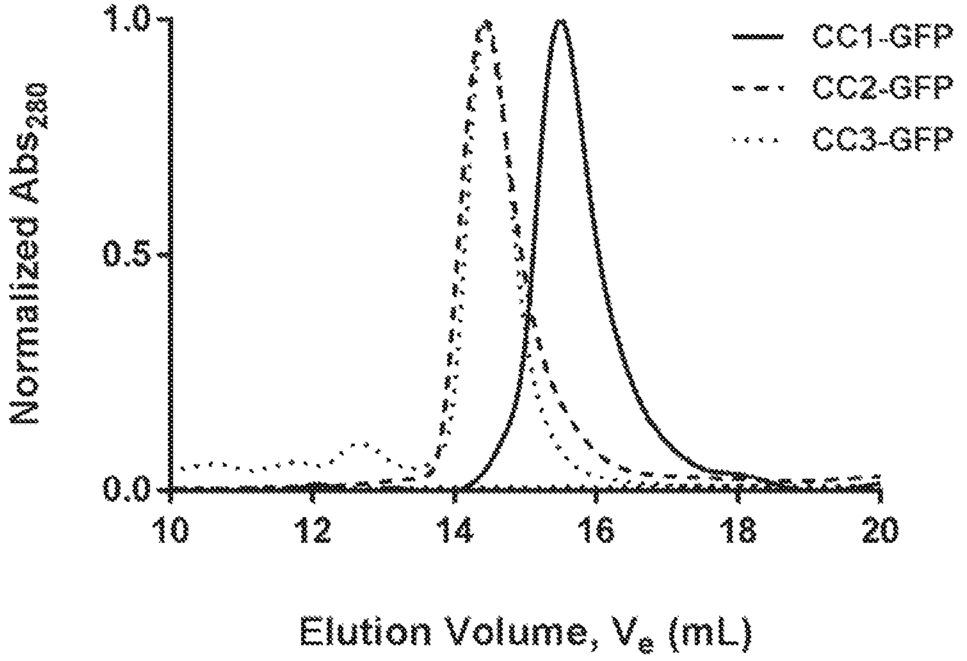
FIG. 89 shows a graph demonstrating an overlay of gel filtration chromatograms of individual CC-GFP. Approximate molecular weights were calculated at 29 kDa, 47 kDa, and 47 kDa for CC1-GFP, CC2-GFP, and CC3-GFP, respectively. Molecular weights of protein standards: 1, thyroglobulin—670 kDa; 2, gamma globulin—158 kDa; 3, ovalbumin—44 kDa; 4, myoglobin—17 kDa.

FIG. 89 shows a graph demonstrating an overlay of gel filtration chromatograms of individual CC fusion proteins. After purification via IMAC, CC fusion proteins were concentrated to 30 μM in PBS using Amicon centrifugal filters with a 10 kDa cut-off and passed through a gel filtration column to determine their approximate molecular weight. The approximate molecular weights were calculated to be about 29 kDa, about 47 kDa, and about 47 kDa for CC1-GFP, CC2-GFP, and CC3-GFP, respectively by interpolation using the following protein standards: 1, thyroglobulin—670 kDa; 2, gamma globulin—158 kDa; 3, ovalbumin—44 kDa; 4, myoglobin—17 kDa.

Figure 90:
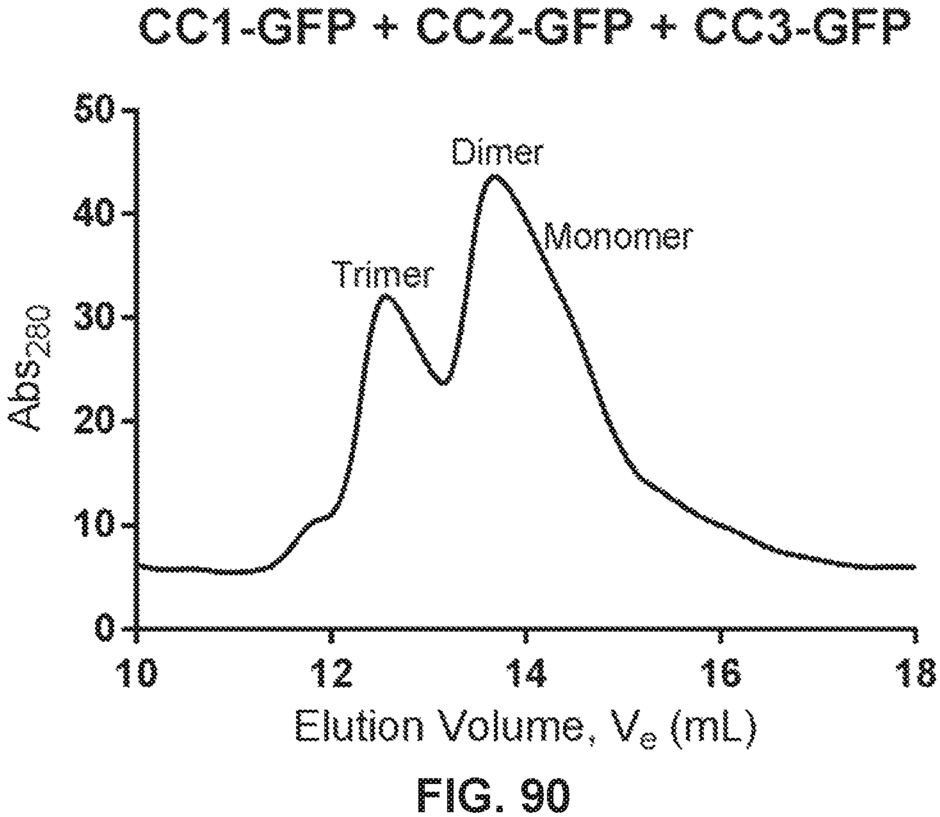
FIG. 90 shows a graph demonstrating a gel filtration chromatogram of combined CC-GFP. Approximate molecular weights were calculated at 107 kDa, 65 kDa, and 36 kDa for trimer peak, dimer peak, and monomer peak, respectively. Molecular weights of protein standards: 1, thyroglobulin—670 kDa; 2, gamma globulin—158 kDa; 3, ovalbumin—44 kDa; 4, myoglobin—17 kDa.
Figure 91A:
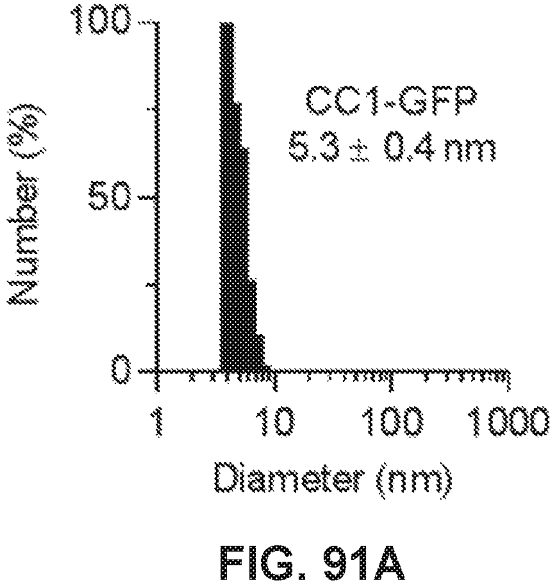
FIGS. 91A-91G shows graphs that can demonstrate the average hydrodynamic diameters of CC fusion proteins, individually or combined, using dynamic light scattering technique.
Figure 91B:
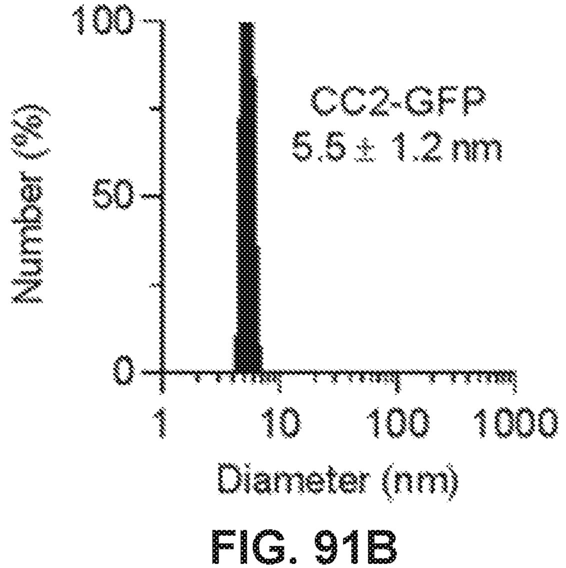
Figure 91C:
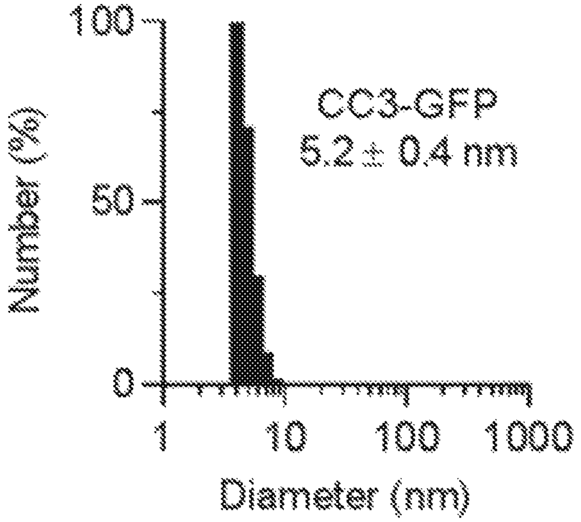
Figure 91D:
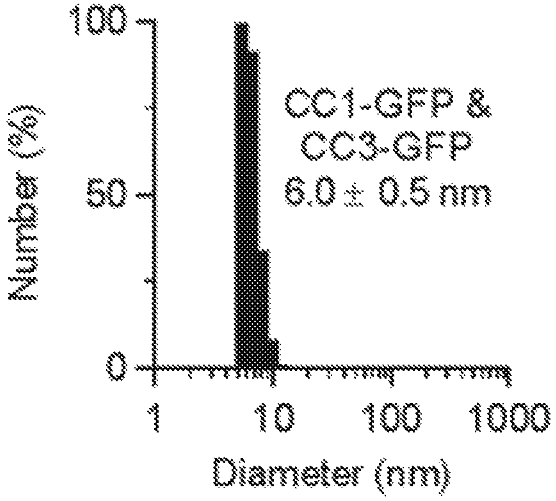
Figure 91E:
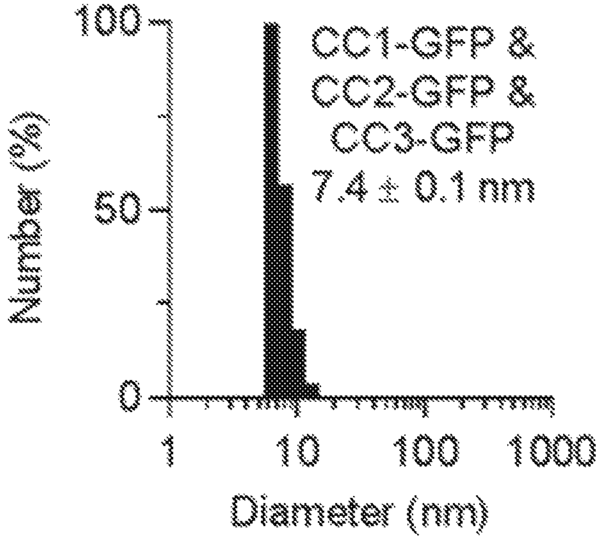
Figure 91F:
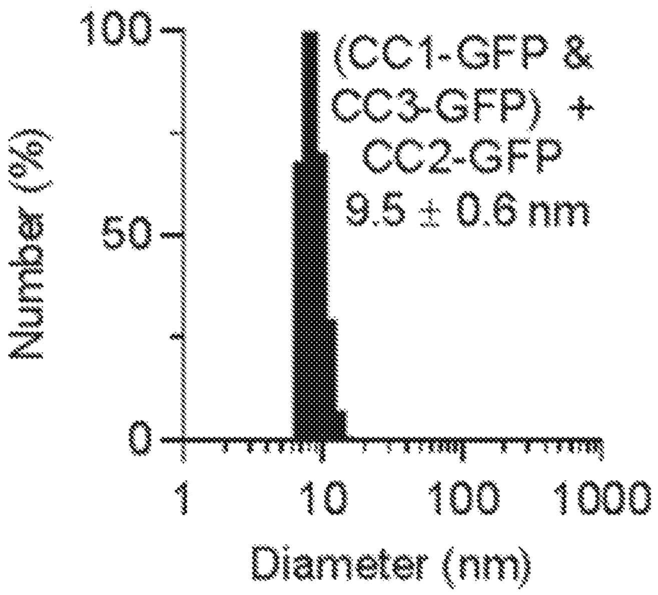
Figure 91G:
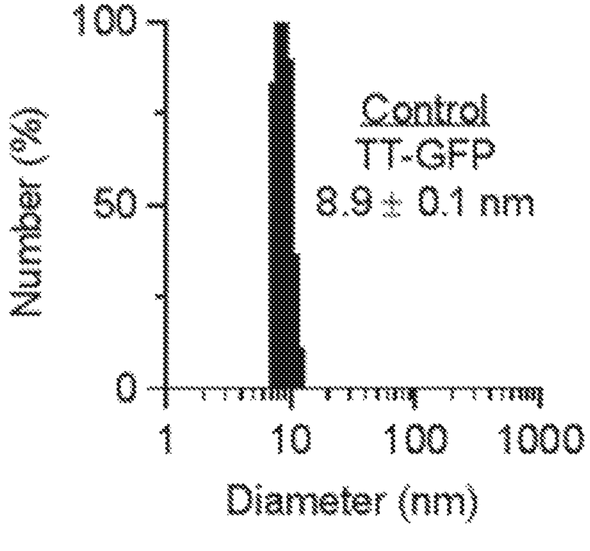

FIG. 90 shows a graph demonstrating a gel filtration chromatogram of combined CC fusion proteins. Purified CC fusion proteins were mixed together at equimolar concentrations and allowed to assemble at 4° C. overnight before being flown through the gel filtration column. Approximate molecular weights were calculated at 107 kDa, 65 kDa, and 36 kDa for trimer peak, dimer peak, and monomer peak, respectively. Molecular weights of protein standards: 1, thyroglobulin—670 kDa; 2, gamma globulin—158 kDa; 3, ovalbumin—44 kDa; 4, myoglobin—17 kDa.

FIGS. 91A-91G shows graphs that can demonstrate the average hydrodynamic diameters of CC fusion proteins, individually or combined, using dynamic light scattering technique. Prior to this, proteins were filtered using low-binding 0.22 μm sterile filters. The concentration of protein or trimer to perform this technique was 20 μM. The instrument collected data for 10 cycles. This data was measured a total of three times to calculate a total average and standard deviation.

Figure 92:
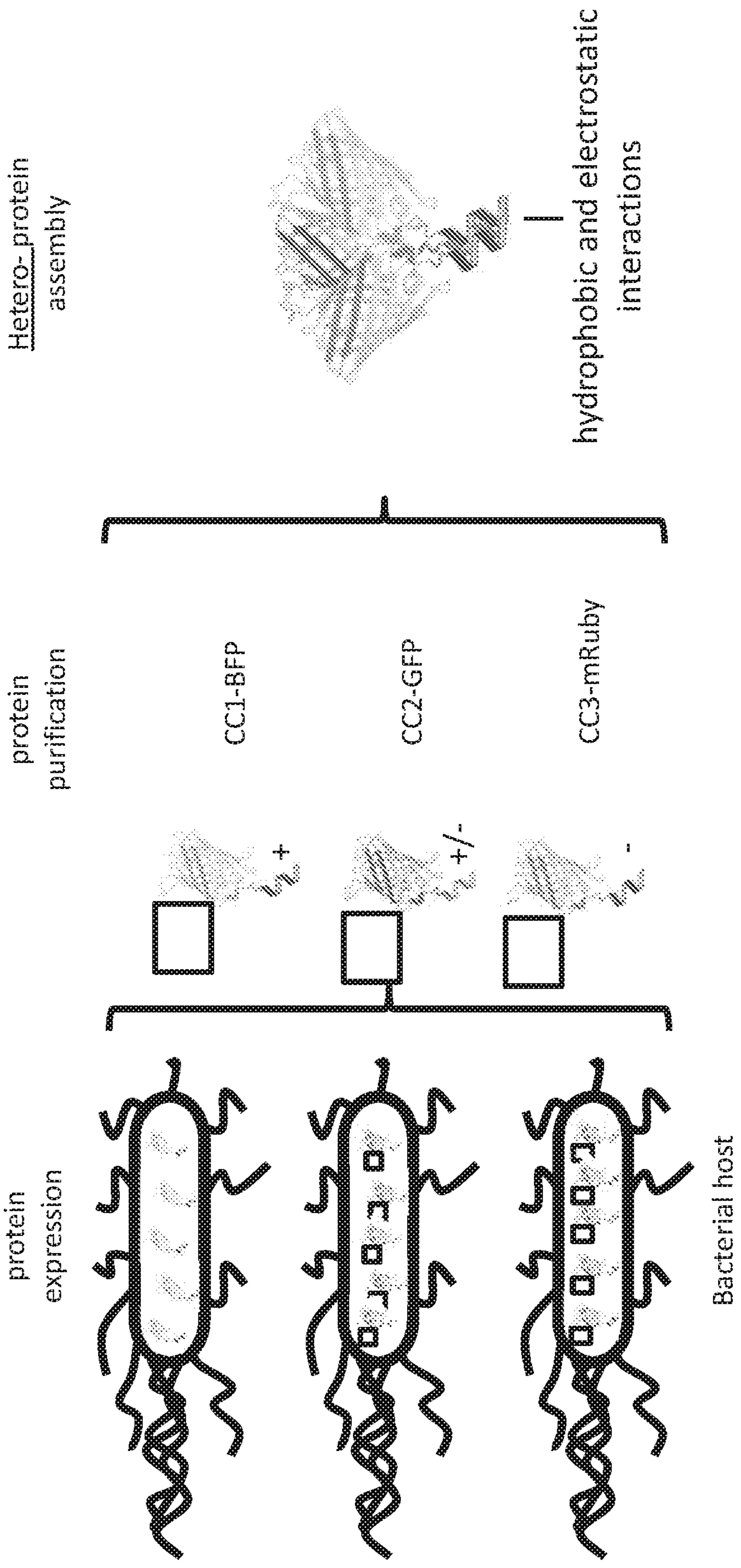
FIG. 92 shows a schematic representation of CC1, CC2, and CC3 fused to three different proteins, and an embodiment of a heterotrimeric coiled-coil fusion protein assembly as provided herein.

FIG. 92 100 shows a schematic representation of CC1, CC2, and CC3 fused to three different proteins, and an embodiment of a heterotrimeric coiled-coil heteromeric fusion protein assembly as provided herein. Cloning, expression, purification, and assembly are performed as written in the description of FIG. 86.

Figure 93:
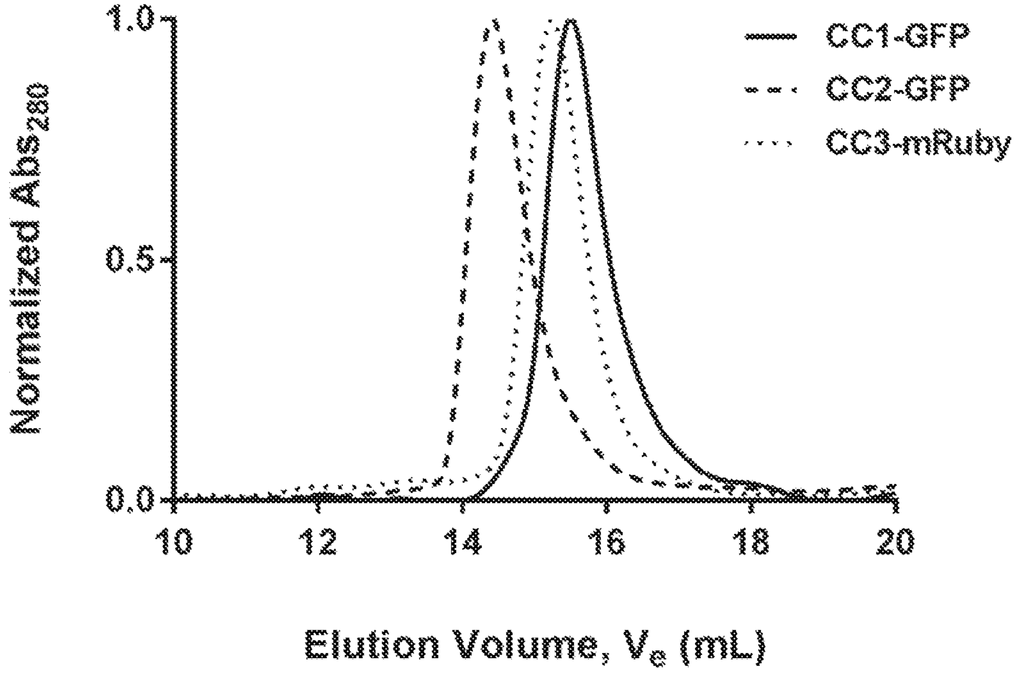
FIG. 93 shows a graph that can demonstrate an overlay of gel filtration chromatograms of individual CC fusion proteins. Approximate molecular weights were calculated at 29 kDa, 47 kDa, and 33 kDa for CC1-GFP, CC2-GFP, and CC3-mRuby, respectively. Molecular weights of protein standards: 1, thyroglobulin—670 kDa; 2, gamma globulin—158 kDa; 3, ovalbumin—44 kDa; 4, myoglobin—17 kDa.

FIG. 93 shows a graph demonstrating an overlay of gel filtration chromatograms of individual CC fusion proteins. After purification via IMAC, CC fusion proteins were concentrated to 30 μM in PBS using Amicon centrifugal filters with a 10 kDa cut-off and passed through a gel filtration column to determine their approximate molecular weight. The approximate molecular weights were calculated to be about 29 kDa, about 47 kDa, and about 33 kDa for CC1-GFP, CC2-GFP, and CC3-mRuby, respectively. Molecular weights of protein standards: 1, thyroglobulin—670 kDa; 2, gamma globulin—158 kDa; 3, ovalbumin—44 kDa; 4, myoglobin—17 kDa.

Figure 94:
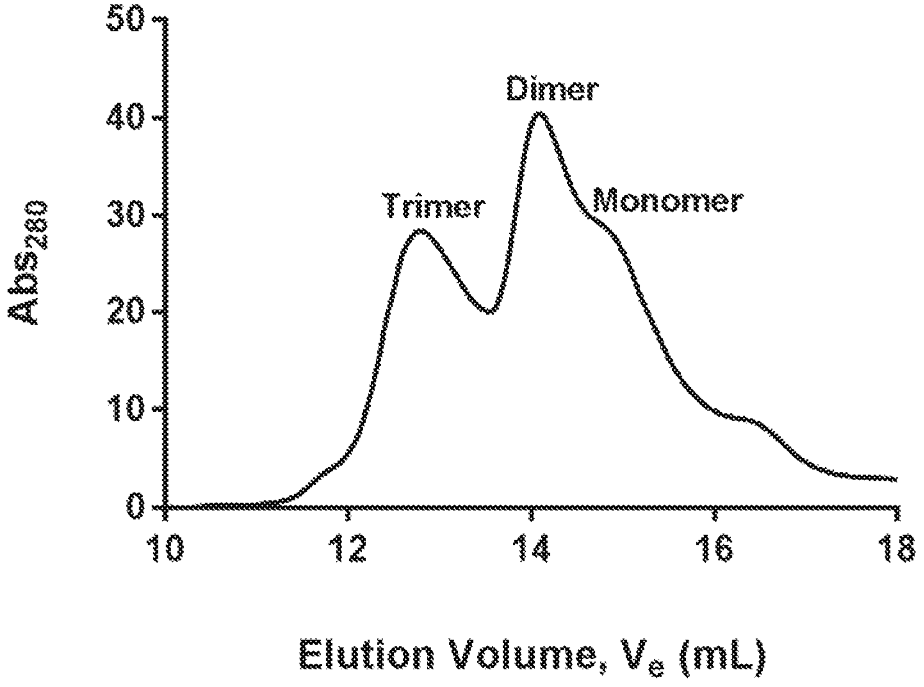
FIG. 94 shows a graph that can demonstrate a gel filtration chromatogram of combined CC fluorescent protein. Approximate molecular weights were calculated at 97 kDa, 58 kDa, and 33 kDa for trimer peak, dimer peak, and monomer peak, respectively. Molecular weights of protein standards: 1, thyroglobulin—670 kDa; 2, gamma globulin—158 kDa; 3, ovalbumin—44 kDa; 4, myoglobin—17 kDa.

FIG. 94 shows a graph that can demonstrate a gel filtration chromatogram of combined CC fluorescent protein. Purified CC fusion proteins were mixed together at equimolar concentrations and allowed to assemble at 4° C. overnight before being flown through the gel filtration column. Approximate molecular weights were calculated at about 97 kDa, about 58 kDa, and about 33 kDa for trimer peak, dimer peak, and monomer peak, respectively. Molecular weights of protein standards: 1, thyroglobulin—670 kDa; 2, gamma globulin—158 kDa; 3, ovalbumin—44 kDa; 4, myoglobin—17 kDa.

Figure 95:
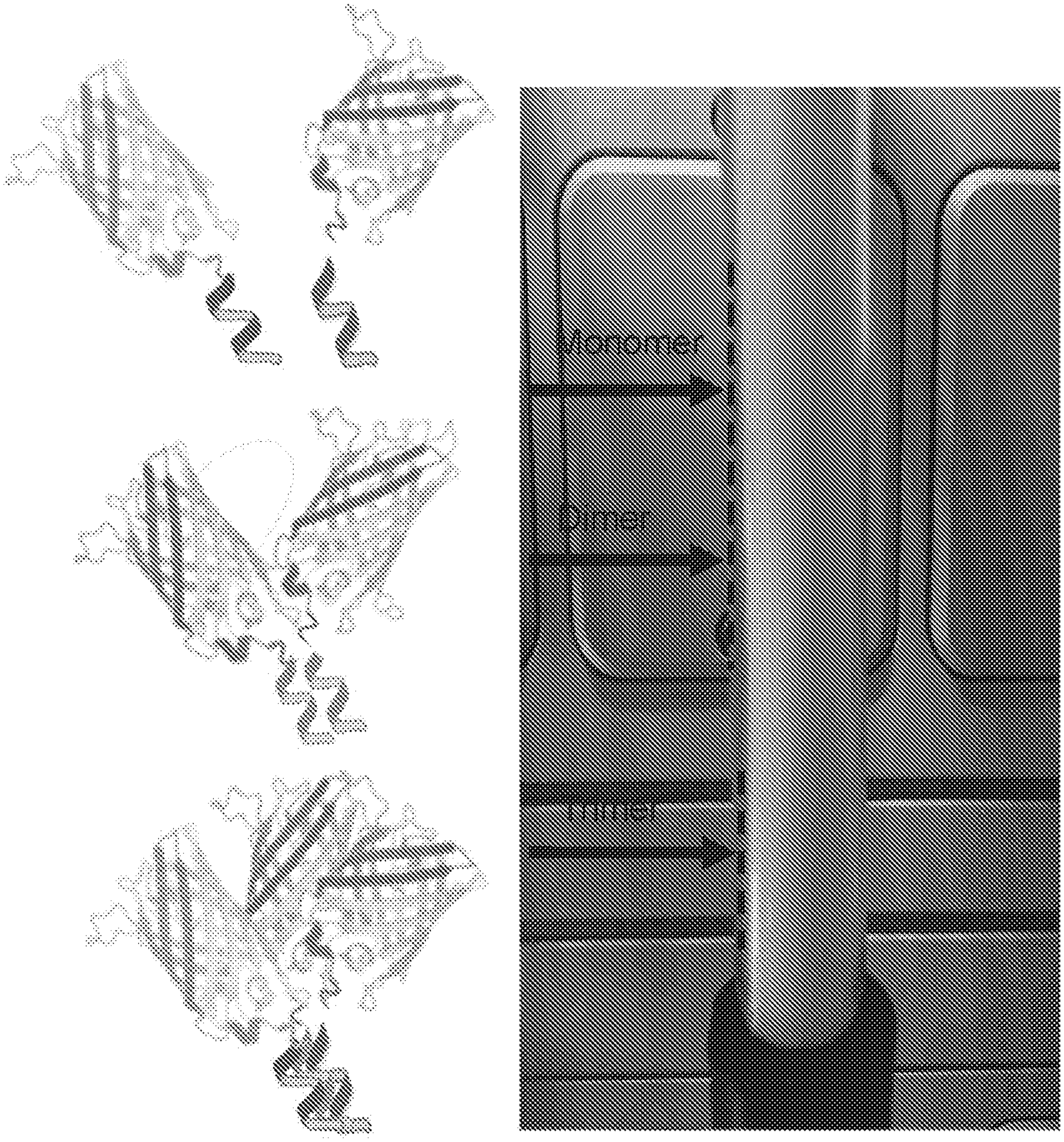
FIG. 95 shows an image taken of the gel filtration column of combined CC fluorescent protein in FIG. 94. Arrows point to regions corresponding with the trimer peak, dimer peak, and monomer peak on the chromatogram.

FIG. 95 shows an image taken of the gel filtration column of combined CC fluorescent protein in FIG. 94. Arrows point to regions corresponding with the trimer peak, dimer peak, and monomer peak on the chromatogram.

Figure 96:
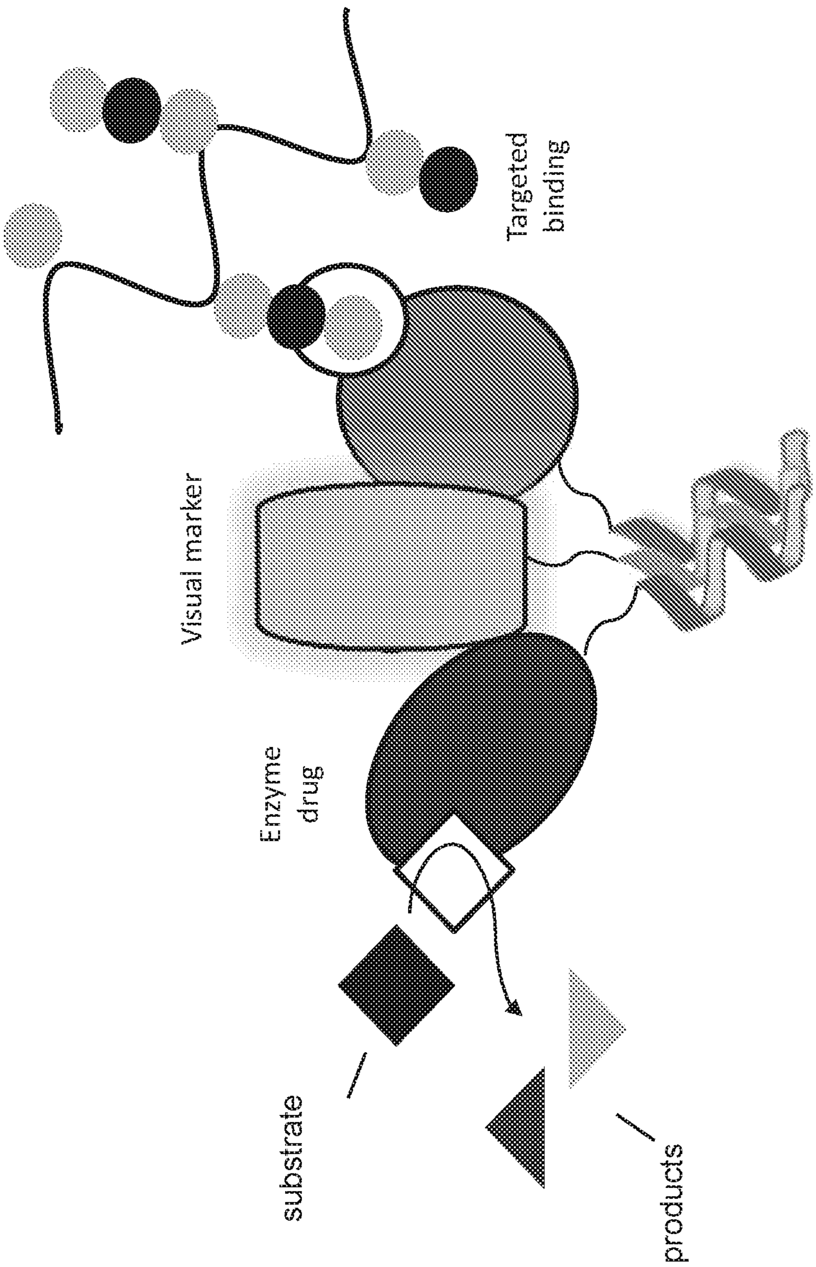
FIG. 96 shows a cartoon demonstrating an embodiment of a heterotrimeric coil assembled from CC1, CC2, and CC3 functional fusion proteins with effector, diagnostic, and targeting capabilities.

FIG. 96 shows a cartoon demonstrating an embodiment of a heterotrimeric coil assembled from CC1, CC2, and CC3 functional fusion proteins with effector, diagnostic, and targeting capabilities. This platform is designed such that the combination or type of fused protein is variable.

We claim:

1. A targeted effector fusion protein comprising:

an effector protein; and a targeting moiety, wherein the targeting moiety is operatively linked to the effector protein via a linker, wherein the linker comprises a polypeptide sequence that is about 90 to 100% identical to any one of SEQ ID NOs: 2-16.

2. The targeted effector fusion protein of claim 1, wherein the linker is a flexible linker or a rigid linker.

3. The targeted effector fusion protein of claim 2, wherein the targeting moiety is capable of specifically binding to a carbohydrate.

4. The targeted effector fusion protein of claim 1, wherein the effector protein is an enzyme.

5. The targeted effector fusion protein of claim 4, wherein the enzyme is indoleamine 2,3 dioxygenase.

6. The targeted effector fusion protein of claim 1, wherein the targeting moiety is a galectin protein.

7. The targeted effector fusion protein of claim 6, wherein the targeting moiety is galectin-3.

8. The targeted effector protein of claim 1, wherein the linker is an alpha coil polypeptide or a random coil polypeptide.

9. The targeted effector protein of claim 8, wherein the alpha coil polypeptide comprises one or more heptads, where each heptad has the general formula of AB C D E F G, wherein amino acids A and D are each a hydrophobic amino acid, wherein amino acids B, C, E, F, and G, are each independently selected from a hydrophilic amino acid, a polar amino acid, or a charged amino acid.

10. The targeted effector protein of claim 8, wherein the alpha coil polypeptide is capable of multimerizing with one or more other alpha coils that are integrated in one or more other targeted effector proteins.

11. The targeted effector fusion protein of claim 8, wherein the targeting moiety is capable of specifically binding to a carbohydrate.

12. The targeted effector fusion protein of claim 8, wherein the effector protein is an enzyme.

13. The targeted effector fusion protein of claim 12, wherein the enzyme is indoleamine 2,3 dioxygenase.

14. The targeted effector fusion protein of claim 8, wherein the targeting moiety is a galectin protein.

15. The targeted effector fusion protein of claim 14, wherein the targeting moiety is galectin-3.

16. A multimeric targeted effector fusion protein complex comprising:

at least two targeted effector fusion proteins according to claim 8, wherein the at least two targeted effector proteins are conjugated to each other by binding between the alpha coil polypeptide or random coil polypeptide in each of the at least two targeted effector proteins.

17. The multimeric targeted effector fusion protein complex of claim 16, wherein the multimeric targeted effector fusion protein complex is homogeneous.

18. The multimeric targeted effector fusion protein complex of claim 16, wherein the multimeric targeted effector fusion protein complex is heterogeneous.

19. A pharmaceutical formulation comprising:

a targeted effector fusion protein as in claim 1; and a pharmaceutically acceptable carrier.

20. A pharmaceutical formulation comprising:

a multimeric targeted effector fusion protein complex as in claim 16; and a pharmaceutically acceptable carrier.

21. A targeted effector fusion protein comprising:

an effector protein; and a targeting moiety, wherein the targeting moiety is operatively linked to the effector protein via a linker, wherein the effector protein is indoleamine 2,3 dioxygenase, and wherein the targeting moiety is a galectin protein.

22. The targeted effector fusion protein of claim 21, wherein the targeting moiety is galectin-3.

23. The targeted effector protein of claim 21, wherein the linker is an alpha coil polypeptide or a random coil polypeptide.

24. A multimeric targeted effector fusion protein complex comprising:

at least two targeted effector fusion proteins according to claim 23, wherein the at least two targeted effector proteins are conjugated to each other by binding between the alpha coil polypeptide or random coil polypeptide in each of the at least two targeted effector proteins.

25. The multimeric targeted effector fusion protein complex of claim 24, wherein the multimeric targeted effector fusion protein complex is homogeneous.

26. The multimeric targeted effector fusion protein complex of claim 24, wherein the multimeric targeted effector fusion protein complex is heterogeneous.

* * * * *

SEQUENCE LISTING

```
<160> NUMBER OF SEQ ID NOS: 25

<210> SEQ ID NO 1
<211> LENGTH: 496
<212> TYPE: PRT
<213> ORGANISM: Artificial Sequence
<220> FEATURE:
<223> OTHER INFORMATION: A fustion protein as described herein

<400> SEQUENCE: 1

Met Ala Val Phe Thr Leu Glu Asp Phe Val Gly Asp Trp Arg Gln Thr
1               5                   10                  15

Ala Gly Tyr Asn Leu Asp Gln Val Leu Glu Gln Gly Gly Val Ser Ser
            20                  25                  30

Leu Phe Gln Asn Leu Gly Val Ser Val Thr Pro Ile Gln Arg Ile Val
        35                  40                  45

Leu Ser Gly Glu Asn Gly Leu Lys Ile Asp Ile His Val Ile Ile Pro
    50                  55                  60

Tyr Glu Gly Leu Ser Gly Asp Gln Met Gly Gln Ile Glu Lys Ile Phe
65                  70                  75                  80

Lys Val Val Tyr Pro Val Asp Asp His His Phe Lys Val Ile Leu His
                85                  90                  95

Tyr Gly Thr Leu Val Ile Asp Gly Val Thr Pro Asn Met Ile Asp Tyr
            100                 105                 110
```

-continued

```
Phe Gly Arg Pro Tyr Glu Gly Ile Ala Val Phe Asp Gly Lys Lys Ile
        115                 120                 125

Thr Val Thr Gly Thr Leu Trp Asn Gly Asn Lys Ile Ile Asp Glu Arg
    130                 135                 140

Leu Ile Asn Pro Asp Gly Ser Leu Leu Phe Arg Val Thr Ile Asn Gly
145                 150                 155                 160

Val Thr Gly Trp Arg Leu Cys Glu Arg Ile Leu Ala Gly Ser Gly Gly
                165                 170                 175

Gly Ser Gly Gly Ser Gly Gly Ser Gly Gly Met Ala Arg Met Lys Gln
            180                 185                 190

Leu Glu Asp Lys Val Glu Glu Leu Leu Ser Lys Asn Tyr His Leu Glu
        195                 200                 205

Asn Arg Val Ala Arg Leu Glu Lys Leu Val Gly Glu Arg Gly Gly Gly
    210                 215                 220

Ser Gly Gly Ser Gly Gly Gly Gly Ser Gly Gly Ser Gly Glu Phe Ala
225                 230                 235                 240

Asp Asn Phe Ser Leu His Asp Ala Leu Ser Gly Ser Gly Asn Pro Asn
                245                 250                 255

Pro Gln Gly Trp Pro Gly Ala Trp Gly Asn Gln Pro Ala Gly Ala Gly
            260                 265                 270

Gly Tyr Pro Gly Ala Ser Tyr Pro Gly Ala Tyr Pro Gly Gln Ala Pro
        275                 280                 285

Pro Gly Ala Tyr Pro Gly Gln Ala Pro Pro Gly Ala Tyr Pro Gly Ala
    290                 295                 300

Pro Gly Ala Tyr Pro Gly Ala Pro Ala Pro Gly Val Tyr Pro Gly Pro
305                 310                 315                 320

Pro Ser Gly Pro Gly Ala Tyr Pro Ser Ser Gly Gln Pro Ser Ala Pro
                325                 330                 335

Gly Ala Tyr Pro Ala Thr Gly Pro Tyr Gly Ala Pro Ala Gly Pro Leu
            340                 345                 350

Ile Val Pro Tyr Asn Leu Pro Leu Pro Gly Gly Val Val Pro Arg Met
        355                 360                 365

Leu Ile Thr Ile Leu Gly Thr Val Lys Pro Asn Ala Asn Arg Ile Ala
    370                 375                 380

Leu Asp Phe Gln Arg Gly Asn Asp Val Ala Phe His Phe Asn Pro Arg
385                 390                 395                 400

Phe Asn Glu Asn Asn Arg Arg Val Ile Val Cys Asn Thr Lys Leu Asp
                405                 410                 415

Asn Asn Trp Gly Arg Glu Glu Arg Gln Ser Val Phe Pro Phe Glu Ser
            420                 425                 430

Gly Lys Pro Phe Lys Ile Gln Val Leu Val Glu Pro Asp His Phe Lys
        435                 440                 445

Val Ala Val Asn Asp Ala His Leu Leu Gln Tyr Asn His Arg Val Lys
    450                 455                 460

Lys Leu Asn Glu Ile Ser Lys Leu Gly Ile Ser Gly Asp Ile Asp Leu
465                 470                 475                 480

Thr Ser Ala Ser Tyr Asn Met Ile Leu Glu His His His His His His
                485                 490                 495
```

<210> SEQ ID NO 2
<211> LENGTH: 35
<212> TYPE: PRT
<213> ORGANISM: Artificial Sequence
<220> FEATURE:

<223> OTHER INFORMATION: An alpha-helix trimer domain (an alpha-helix coil).

<400> SEQUENCE: 2

Met Ala Arg Met Lys Gln Leu Glu Asp Lys Val Glu Glu Leu Leu Ser
1 5 10 15

Lys Asn Tyr His Leu Glu Asn Arg Val Ala Arg Leu Glu Lys Leu Val
20 25 30

Gly Glu Arg
35

<210> SEQ ID NO 3
<211> LENGTH: 34
<212> TYPE: PRT
<213> ORGANISM: Artificial Sequence
<220> FEATURE:
<223> OTHER INFORMATION: An alpha-helix trimer domain.
<220> FEATURE:
<221> NAME/KEY: misc_feature
<222> LOCATION: (1)..(1)
<223> OTHER INFORMATION: Xaa can be any naturally occurring amino acid

<400> SEQUENCE: 3

Xaa Arg Met Lys Gln Leu Glu Asp Lys Val Glu Glu Leu Leu Ser Lys
1 5 10 15

Asn Tyr His Leu Glu Asn Glu Val Ala Arg Leu Lys Lys Leu Val Gly
20 25 30

Glu Arg

<210> SEQ ID NO 4
<211> LENGTH: 757
<212> TYPE: PRT
<213> ORGANISM: Artificial Sequence
<220> FEATURE:
<223> OTHER INFORMATION: Pentamer Alpha-helix domain (full sequence of cartilage-oligomeric matrix protein, or fragments thereof):

<400> SEQUENCE: 4

Met Val Pro Asp Thr Ala Cys Val Leu Leu Leu Thr Leu Ala Ala Leu
1 5 10 15

Gly Ala Ser Gly Gln Gly Gln Ser Pro Leu Gly Ser Asp Leu Gly Pro
20 25 30

Gln Met Leu Arg Glu Leu Gln Glu Thr Asn Ala Ala Leu Gln Asp Val
35 40 45

Arg Asp Trp Leu Arg Gln Gln Val Arg Glu Ile Thr Phe Leu Lys Asn
50 55 60

Thr Val Met Glu Cys Asp Ala Cys Gly Met Gln Gln Ser Val Arg Thr
65 70 75 80

Gly Leu Pro Ser Val Arg Pro Leu Leu His Cys Ala Pro Gly Phe Cys
85 90 95

Phe Pro Gly Val Ala Cys Ile Gln Thr Glu Ser Gly Gly Arg Cys Gly
100 105 110

Pro Cys Pro Ala Gly Phe Thr Gly Asn Gly Ser His Cys Thr Asp Val
115 120 125

Asn Glu Cys Asn Ala His Pro Cys Phe Pro Arg Val Arg Cys Ile Asn
130 135 140

Thr Ser Pro Gly Phe Arg Cys Glu Ala Cys Pro Pro Gly Tyr Ser Gly
145 150 155 160

Pro Thr His Gln Gly Val Gly Leu Ala Phe Ala Lys Ala Asn Lys Gln
165 170 175

-continued

```
Val Cys Thr Asp Ile Asn Glu Cys Glu Thr Gly Gln His Asn Cys Val
            180                 185                 190

Pro Asn Ser Val Cys Ile Asn Thr Arg Gly Ser Phe Gln Cys Gly Pro
        195                 200                 205

Cys Gln Pro Gly Phe Val Gly Asp Gln Ala Ser Gly Cys Gln Arg Gly
    210                 215                 220

Ala Gln Arg Phe Cys Pro Asp Gly Ser Pro Ser Glu Cys His Glu His
225                 230                 235                 240

Ala Asp Cys Val Leu Glu Arg Asp Gly Ser Arg Ser Cys Val Cys Arg
                245                 250                 255

Val Gly Trp Ala Gly Asn Gly Ile Leu Cys Gly Arg Asp Thr Asp Leu
            260                 265                 270

Asp Gly Phe Pro Asp Glu Lys Leu Arg Cys Pro Glu Pro Gln Cys Arg
        275                 280                 285

Lys Asp Asn Cys Val Thr Val Pro Asn Ser Gly Gln Glu Asp Val Asp
    290                 295                 300

Arg Asp Gly Ile Gly Asp Ala Cys Asp Pro Asp Ala Asp Gly Asp Gly
305                 310                 315                 320

Val Pro Asn Glu Lys Asp Asn Cys Pro Leu Val Arg Asn Pro Asp Gln
                325                 330                 335

Arg Asn Thr Asp Glu Asp Lys Trp Gly Asp Ala Cys Asp Asn Cys Arg
            340                 345                 350

Ser Gln Lys Asn Asp Asp Gln Lys Asp Thr Asp Gln Asp Gly Arg Gly
        355                 360                 365

Asp Ala Cys Asp Asp Asp Ile Asp Gly Asp Arg Ile Arg Asn Gln Ala
    370                 375                 380

Asp Asn Cys Pro Arg Val Pro Asn Ser Asp Gln Lys Asp Ser Asp Gly
385                 390                 395                 400

Asp Gly Ile Gly Asp Ala Cys Asp Asn Cys Pro Gln Lys Ser Asn Pro
                405                 410                 415

Asp Gln Ala Asp Val Asp His Asp Phe Val Gly Asp Ala Cys Asp Ser
            420                 425                 430

Asp Gln Asp Gln Asp Gly Asp Gly His Gln Asp Ser Arg Asp Asn Cys
        435                 440                 445

Pro Thr Val Pro Asn Ser Ala Gln Glu Asp Ser Asp His Asp Gly Gln
    450                 455                 460

Gly Asp Ala Cys Asp Asp Asp Asp Asp Asn Asp Gly Val Pro Asp Ser
465                 470                 475                 480

Arg Asp Asn Cys Arg Leu Val Pro Asn Pro Gly Gln Glu Asp Ala Asp
                485                 490                 495

Arg Asp Gly Val Gly Asp Val Cys Gln Asp Asp Phe Asp Ala Asp Lys
            500                 505                 510

Val Val Asp Lys Ile Asp Val Cys Pro Glu Asn Ala Glu Val Thr Leu
        515                 520                 525

Thr Asp Phe Arg Ala Phe Gln Thr Val Val Leu Asp Pro Glu Gly Asp
    530                 535                 540

Ala Gln Ile Asp Pro Asn Trp Val Val Leu Asn Gln Gly Arg Glu Ile
545                 550                 555                 560

Val Gln Thr Met Asn Ser Asp Pro Gly Leu Ala Val Gly Tyr Thr Ala
                565                 570                 575

Phe Asn Gly Val Asp Phe Glu Gly Thr Phe His Val Asn Thr Val Thr
            580                 585                 590
```

-continued

```
Asp Asp Asp Tyr Ala Gly Phe Ile Phe Gly Tyr Gln Asp Ser Ser Ser
        595                 600                 605

Phe Tyr Val Val Met Trp Lys Gln Met Glu Gln Thr Tyr Trp Gln Ala
    610                 615                 620

Asn Pro Phe Arg Ala Val Ala Glu Pro Gly Ile Gln Leu Lys Ala Val
625                 630                 635                 640

Lys Ser Ser Thr Gly Pro Gly Glu Gln Leu Arg Asn Ala Leu Trp His
                645                 650                 655

Thr Gly Asp Thr Glu Ser Gln Val Arg Leu Leu Trp Lys Asp Pro Arg
            660                 665                 670

Asn Val Gly Trp Lys Asp Lys Lys Ser Tyr Arg Trp Phe Leu Gln His
        675                 680                 685

Arg Pro Gln Val Gly Tyr Ile Arg Val Arg Phe Tyr Glu Gly Pro Glu
    690                 695                 700

Leu Val Ala Asp Ser Asn Val Val Leu Asp Thr Thr Met Arg Gly Gly
705                 710                 715                 720

Arg Leu Gly Val Phe Cys Phe Ser Gln Glu Asn Ile Ile Trp Ala Asn
                725                 730                 735

Leu Arg Tyr Arg Cys Asn Asp Thr Ile Pro Glu Asp Tyr Glu Thr His
            740                 745                 750

Gln Leu Arg Gln Ala
        755


<210> SEQ ID NO 5
<211> LENGTH: 34
<212> TYPE: PRT
<213> ORGANISM: Artificial Sequence
<220> FEATURE:
<223> OTHER INFORMATION: A tetramer Alpha-helix domain: GCN4-pVe/GCN4-
      pVg HETEROTETRAMER; GCN4-pVe SEQUENCE

<400> SEQUENCE: 5

Met Lys Val Lys Gln Leu Val Asp Lys Val Glu Glu Leu Leu Ser Lys
1               5                   10                  15

Asn Tyr His Leu Val Asn Glu Val Ala Arg Leu Val Lys Leu Val Gly
            20                  25                  30

Glu Arg


<210> SEQ ID NO 6
<211> LENGTH: 34
<212> TYPE: PRT
<213> ORGANISM: Artificial Sequence
<220> FEATURE:
<223> OTHER INFORMATION: Tetramer Alpha-helix domains: GCN4-pVe/GCN4-pVg
      HETEROTETRAMER:GCN4-pVg

<400> SEQUENCE: 6

Met Lys Val Lys Gln Leu Glu Asp Val Val Glu Glu Leu Leu Ser Val
1               5                   10                  15

Asn Tyr His Leu Glu Asn Val Val Ala Arg Leu Lys Lys Leu Val Gly
            20                  25                  30

Glu Arg


<210> SEQ ID NO 7
<211> LENGTH: 34
<212> TYPE: PRT
<213> ORGANISM: Artificial Sequence
<220> FEATURE:
<223> OTHER INFORMATION: Tetramer Alpha-helix domains:GCN4-pVe/GCN4-pVg
      HETEROTETRAMER: GCN4-pAe SEQUENCE
```

<400> SEQUENCE: 7

Met Lys Val Lys Gln Leu Ala Asp Lys Val Glu Glu Leu Leu Ser Lys
1 5 10 15

Asn Tyr His Leu Ala Asn Glu Val Ala Arg Leu Ala Lys Leu Val Gly
20 25 30

Glu Arg

<210> SEQ ID NO 8
<211> LENGTH: 34
<212> TYPE: PRT
<213> ORGANISM: Artificial Sequence
<220> FEATURE:
<223> OTHER INFORMATION: Tetramer Alpha-helix domains: GCN4-pVe/GCN4-pVg HETEROTETRAMER: GCN4-pAg SEQUENCE

<400> SEQUENCE: 8

Met Lys Val Lys Gln Leu Glu Asp Ala Val Glu Glu Leu Leu Ser Ala
1 5 10 15

Asn Tyr His Leu Glu Asn Ala Val Ala Arg Leu Lys Lys Leu Val Gly
20 25 30

Glu Arg

<210> SEQ ID NO 9
<211> LENGTH: 31
<212> TYPE: PRT
<213> ORGANISM: Artificial Sequence
<220> FEATURE:
<223> OTHER INFORMATION: A heptamer Alpha-helix domain (CC-Hept)
<220> FEATURE:
<221> NAME/KEY: misc_feature
<222> LOCATION: (1)..(1)
<223> OTHER INFORMATION: Xaa can be any naturally occurring amino acid

<400> SEQUENCE: 9

Xaa Gly Glu Ile Ala Gln Ala Leu Lys Glu Ile Ala Lys Ala Leu Lys
1 5 10 15

Glu Ile Ala Trp Ala Leu Lys Glu Ile Ala Gln Ala Leu Lys Gly
20 25 30

<210> SEQ ID NO 10
<211> LENGTH: 31
<212> TYPE: PRT
<213> ORGANISM: Artificial Sequence
<220> FEATURE:
<223> OTHER INFORMATION: A Heptamer Alpha-helix domain (CC-Hept-homoCys-H-E)
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 10

Xaa Gly Glu Ile Ala Lys Ala Leu Arg Glu Ile Ala Lys Ala Leu Arg
1 5 10 15

Glu Xaa Ala Trp Ala His Arg Glu Glu Ala Lys Ala Leu Arg Gly
20 25 30

<210> SEQ ID NO 11
<211> LENGTH: 31
<212> TYPE: PRT

<213> ORGANISM: Artificial Sequence
<220> FEATURE:
<223> OTHER INFORMATION: A heptamer Alpha-helix domain (CC-Hept-I18betaMeCys-L22H-I25E)
<220> FEATURE:
<221> NAME/KEY: misc_feature
<222> LOCATION: (1)..(1)
<223> OTHER INFORMATION: Xaa can be any naturally occurring amino acid

<400> SEQUENCE: 11

```
Xaa Gly Glu Ile Ala Lys Ala Leu Arg Glu Ile Ala Lys Ala Leu Arg
1               5                   10                  15

Glu Cys Ala Trp Ala His Arg Glu Glu Ala Lys Ala Leu Arg Gly
            20                  25                  30
```

<210> SEQ ID NO 12
<211> LENGTH: 31
<212> TYPE: PRT
<213> ORGANISM: Artificial Sequence
<220> FEATURE:
<223> OTHER INFORMATION: A Heptamer Alpha-helix domain (CC-Hept-I18C-L22H-I25E )
<220> FEATURE:
<221> NAME/KEY: misc_feature
<222> LOCATION: (1)..(1)
<223> OTHER INFORMATION: Xaa can be any naturally occurring amino acid

<400> SEQUENCE: 12

```
Xaa Gly Glu Ile Ala Lys Ala Leu Arg Glu Ile Ala Lys Ala Leu Arg
1               5                   10                  15

Glu Cys Ala Trp Ala His Arg Glu Glu Ala Lys Ala Leu Arg Gly
            20                  25                  30
```

<210> SEQ ID NO 13
<211> LENGTH: 31
<212> TYPE: PRT
<213> ORGANISM: Artificial Sequence
<220> FEATURE:
<223> OTHER INFORMATION: A Heptamer Alpha-helix domain (CC-Hept-I18C-L22H )
<220> FEATURE:
<221> NAME/KEY: misc_feature
<222> LOCATION: (1)..(1)
<223> OTHER INFORMATION: Xaa can be any naturally occurring amino acid

<400> SEQUENCE: 13

```
Xaa Gly Glu Ile Ala Lys Ala Leu Arg Glu Ile Ala Lys Ala Leu Arg
1               5                   10                  15

Glu Cys Ala Trp Ala His Arg Glu Ile Ala Lys Ala Leu Arg Gly
            20                  25                  30
```

<210> SEQ ID NO 14
<211> LENGTH: 31
<212> TYPE: PRT
<213> ORGANISM: Artificial Sequence
<220> FEATURE:
<223> OTHER INFORMATION: A Heptamer Alpha-helix domain (CC-Hept-I-H-I )
<220> FEATURE:
<221> NAME/KEY: misc_feature
<222> LOCATION: (1)..(1)
<223> OTHER INFORMATION: Xaa can be any naturally occurring amino acid

<400> SEQUENCE: 14

```
Xaa Gly Glu Ile Ala Lys Ala Leu Arg Glu Ile Ala Lys Ala Leu Arg
1               5                   10                  15

Glu Ile Ala Trp Ala His Arg Glu Ile Ala Lys Ala Leu Arg Gly
            20                  25                  30
```

```
<210> SEQ ID NO 15
<211> LENGTH: 31
<212> TYPE: PRT
<213> ORGANISM: Artificial Sequence
<220> FEATURE:
<223> OTHER INFORMATION: A Heptamer Alpha-helix domain (CC-Hept-I-C-I )
<220> FEATURE:
<221> NAME/KEY: misc_feature
<222> LOCATION: (1)..(1)
<223> OTHER INFORMATION: Xaa can be any naturally occurring amino acid

<400> SEQUENCE: 15

Xaa Gly Glu Ile Ala Gln Ala Leu Lys Glu Ile Ala Lys Ala Leu Lys
1               5                   10                  15

Glu Ile Ala Trp Ala Cys Lys Glu Ile Ala Gln Ala Leu Lys Gly
            20                  25                  30


<210> SEQ ID NO 16
<211> LENGTH: 34
<212> TYPE: PRT
<213> ORGANISM: Artificial Sequence
<220> FEATURE:
<223> OTHER INFORMATION: A Heptamer Alpha-helix domain (GCN4-pAA
      SEQUENCE)

<400> SEQUENCE: 16

Met Lys Val Lys Gln Leu Ala Asp Ala Val Glu Glu Leu Ala Ser Ala
1               5                   10                  15

Asn Tyr His Leu Ala Asn Ala Val Ala Arg Leu Ala Lys Ala Val Gly
            20                  25                  30

Glu Arg


<210> SEQ ID NO 17
<211> LENGTH: 170
<212> TYPE: PRT
<213> ORGANISM: Artificial Sequence
<220> FEATURE:
<223> OTHER INFORMATION: A nanoluciferase

<400> SEQUENCE: 17

Val Phe Thr Leu Glu Asp Phe Val Gly Asp Trp Arg Gln Thr Ala Gly
1               5                   10                  15

Tyr Asn Leu Asp Gln Val Leu Glu Gln Gly Gly Val Ser Ser Leu Phe
            20                  25                  30

Gln Asn Leu Gly Val Ser Val Thr Pro Ile Gln Arg Ile Val Leu Ser
        35                  40                  45

Gly Glu Asn Gly Leu Lys Ile Asp Ile His Val Ile Ile Pro Tyr Glu
    50                  55                  60

Gly Leu Ser Gly Asp Gln Met Gly Gln Ile Glu Lys Ile Phe Lys Val
65                  70                  75                  80

Val Tyr Pro Val Asp Asp His His Phe Lys Val Ile Leu His Tyr Gly
                85                  90                  95

Thr Leu Val Ile Asp Gly Val Thr Pro Asn Met Ile Asp Tyr Phe Gly
            100                 105                 110

Arg Pro Tyr Glu Gly Ile Ala Val Phe Asp Gly Lys Lys Ile Thr Val
        115                 120                 125

Thr Gly Thr Leu Trp Asn Gly Asn Lys Ile Ile Asp Glu Arg Leu Ile
    130                 135                 140

Asn Pro Asp Gly Ser Leu Leu Phe Arg Val Thr Ile Asn Gly Val Thr
145                 150                 155                 160
```

-continued

```
Gly Trp Arg Leu Cys Glu Arg Ile Leu Ala
                165                 170


<210> SEQ ID NO 18
<211> LENGTH: 14
<212> TYPE: PRT
<213> ORGANISM: Artificial Sequence
<220> FEATURE:
<223> OTHER INFORMATION: A linker

<400> SEQUENCE: 18

Gly Ser Gly Gly Gly Ser Gly Gly Ser Gly Gly Ser Gly Gly
1               5                   10


<210> SEQ ID NO 19
<211> LENGTH: 16
<212> TYPE: PRT
<213> ORGANISM: Artificial Sequence
<220> FEATURE:
<223> OTHER INFORMATION: A linker

<400> SEQUENCE: 19

Gly Gly Gly Ser Gly Gly Ser Gly Gly Gly Gly Ser Gly Gly Ser Gly
1               5                   10                  15


<210> SEQ ID NO 20
<211> LENGTH: 33
<212> TYPE: PRT
<213> ORGANISM: Artificial Sequence
<220> FEATURE:
<223> OTHER INFORMATION: CC1

<400> SEQUENCE: 20

Met Ala Arg Met Lys Gln Leu Lys Lys Lys Phe Glu Glu Leu Lys Ser
1               5                   10                  15

Lys Ala Gln Gln Leu Lys Lys Lys Ala Ala Gln Leu Lys Lys Lys Val
            20                  25                  30

Gly


<210> SEQ ID NO 21
<211> LENGTH: 33
<212> TYPE: PRT
<213> ORGANISM: Artificial Sequence
<220> FEATURE:
<223> OTHER INFORMATION: CC2

<400> SEQUENCE: 21

Met Ala Arg Met Lys Gln Leu Glu Lys Lys Ala Glu Glu Leu Glu Ser
1               5                   10                  15

Lys Phe Gln Gln Leu Glu Lys Lys Ala Ala Gln Leu Glu Lys Lys Val
            20                  25                  30

Gly


<210> SEQ ID NO 22
<211> LENGTH: 32
<212> TYPE: PRT
<213> ORGANISM: Artificial Sequence
<220> FEATURE:
<223> OTHER INFORMATION: CC3

<400> SEQUENCE: 22

Met Ala Arg Met Lys Gln Leu Glu Lys Glu Ala Glu Glu Leu Glu Ser
1               5                   10                  15

Glu Ala Gln Gln Leu Glu Lys Phe Ala Gln Leu Glu Lys Glu Val Gly
```

20 25 30

<210> SEQ ID NO 23
<211> LENGTH: 298
<212> TYPE: PRT
<213> ORGANISM: Artificial Sequence
<220> FEATURE:
<223> OTHER INFORMATION: CC1-GFP

<400> SEQUENCE: 23

Met Ala Arg Met Lys Gln Leu Lys Lys Lys Phe Glu Glu Leu Lys Ser
1 5 10 15

Lys Ala Gln Gln Leu Lys Lys Lys Ala Ala Gln Leu Lys Lys Lys Val
20 25 30

Gly Gly Ser Gly Gly Gly Ser Gly Gly Ser Gly Gly Gly Gly Ser Gly
35 40 45

Gly Ser Gly Glu Phe Ser Lys Gly Glu Glu Leu Phe Thr Gly Val Val
50 55 60

Pro Ile Leu Val Glu Leu Asp Gly Asp Val Asn Gly His Lys Phe Ser
65 70 75 80

Val Arg Gly Glu Gly Glu Gly Asp Ala Thr Ile Gly Lys Leu Thr Leu
85 90 95

Lys Phe Ile Cys Thr Thr Gly Lys Leu Pro Val Pro Trp Pro Thr Leu
100 105 110

Val Thr Thr Leu Thr Tyr Gly Val Gln Cys Phe Ser Arg Tyr Pro Asp
115 120 125

His Met Lys Arg His Asp Phe Phe Lys Ser Ala Met Pro Glu Gly Tyr
130 135 140

Val Gln Glu Arg Thr Ile Ser Phe Lys Asp Asp Gly Lys Tyr Lys Thr
145 150 155 160

Arg Ala Val Val Lys Phe Glu Gly Asp Thr Leu Val Asn Arg Ile Glu
165 170 175

Leu Lys Gly Thr Asp Phe Lys Glu Asp Gly Asn Ile Leu Gly His Lys
180 185 190

Leu Glu Tyr Asn Phe Asn Ser His Asn Val Tyr Ile Thr Ala Asp Lys
195 200 205

Gln Lys Asn Gly Ile Lys Ala Asn Phe Thr Val Arg His Asn Val Glu
210 215 220

Asp Gly Ser Val Gln Leu Ala Asp His Tyr Gln Gln Asn Thr Pro Ile
225 230 235 240

Gly Asp Gly Pro Val Leu Leu Pro Asp Asn His Tyr Leu Ser Thr Gln
245 250 255

Thr Val Leu Ser Lys Asp Pro Asn Glu Lys Arg Asp His Met Val Leu
260 265 270

His Glu Tyr Val Asn Ala Ala Gly Ile Thr Leu Gly Met Asp Glu Leu
275 280 285

Tyr Lys Leu Glu His His His His His His
290 295

<210> SEQ ID NO 24
<211> LENGTH: 307
<212> TYPE: PRT
<213> ORGANISM: Artificial Sequence
<220> FEATURE:
<223> OTHER INFORMATION: CC2-GFP

<400> SEQUENCE: 24

-continued

```
Met Ala Arg Met Lys Gln Leu Glu Lys Lys Ala Glu Glu Leu Glu Ser
1               5                   10                  15

Lys Phe Gln Gln Leu Glu Lys Lys Ala Ala Gln Leu Glu Lys Lys Val
            20                  25                  30

Gly Gly Gly Gly Ser Gly Gly Gly Ser Gly Gly Gly Ser Gly Gly Gly
        35                  40                  45

Ser Met Ser Lys Gly Glu Glu Leu Phe Thr Gly Val Val Pro Ile Leu
    50                  55                  60

Val Glu Leu Asp Gly Asp Val Asn Gly His Lys Phe Ser Val Arg Gly
65                  70                  75                  80

Glu Gly Glu Gly Asp Ala Thr Asn Gly Lys Leu Thr Leu Lys Phe Ile
                85                  90                  95

Cys Thr Thr Gly Lys Leu Pro Val Pro Trp Pro Thr Leu Val Thr Thr
            100                 105                 110

Leu Thr Tyr Gly Val Gln Cys Phe Ser Arg Tyr Pro Asp His Met Lys
        115                 120                 125

Arg His Asp Phe Phe Lys Ser Ala Met Pro Glu Gly Tyr Val Gln Glu
    130                 135                 140

Arg Thr Ile Ser Phe Lys Asp Asp Gly Thr Tyr Lys Thr Arg Ala Glu
145                 150                 155                 160

Val Lys Phe Glu Gly Asp Thr Leu Val Asn Arg Ile Glu Leu Lys Gly
                165                 170                 175

Ile Asp Phe Lys Glu Asp Gly Asn Ile Leu Gly His Lys Leu Glu Tyr
            180                 185                 190

Asn Phe Asn Ser His Asn Val Tyr Ile Thr Ala Asp Lys Gln Lys Asn
        195                 200                 205

Gly Ile Lys Ala Asn Phe Lys Ile Arg His Asn Val Glu Asp Gly Ser
    210                 215                 220

Val Gln Leu Ala Asp His Tyr Gln Gln Asn Thr Pro Ile Gly Asp Gly
225                 230                 235                 240

Pro Val Leu Leu Pro Asp Asn His Tyr Leu Ser Thr Gln Ser Val Leu
                245                 250                 255

Ser Lys Asp Pro Asn Glu Lys Arg Asp His Met Val Leu Leu Glu Phe
            260                 265                 270

Val Thr Ala Ala Gly Ile Thr His Gly Met Asp Glu Leu Tyr Lys Met
        275                 280                 285

Glu Gln Lys Leu Ile Ser Glu Glu Asp Leu Asn Leu Glu His His His
    290                 295                 300

His His His
305
```

<210> SEQ ID NO 25
<211> LENGTH: 298
<212> TYPE: PRT
<213> ORGANISM: Artificial Sequence
<220> FEATURE:
<223> OTHER INFORMATION: CC3-GFP

<400> SEQUENCE: 25

```
Met Ala Arg Met Lys Gln Leu Glu Lys Glu Ala Glu Glu Leu Glu Ser
1               5                   10                  15

Glu Ala Gln Gln Leu Glu Lys Glu Phe Ala Gln Leu Glu Lys Glu Val
            20                  25                  30

Gly Gly Ser Gly Gly Gly Ser Gly Gly Ser Gly Gly Gly Gly Ser Gly
        35                  40                  45
```

-continued

```
Gly Ser Gly Glu Phe Ser Lys Gly Glu Glu Leu Phe Thr Gly Val Val
    50                  55                  60

Pro Ile Leu Val Glu Leu Asp Gly Asp Val Asn Gly His Lys Phe Ser
65                  70                  75                  80

Val Arg Gly Glu Gly Glu Gly Asp Ala Thr Ile Gly Lys Leu Thr Leu
                85                  90                  95

Lys Phe Ile Cys Thr Thr Gly Lys Leu Pro Val Pro Trp Pro Thr Leu
            100                 105                 110

Val Thr Thr Leu Thr Tyr Gly Val Gln Cys Phe Ser Arg Tyr Pro Asp
        115                 120                 125

His Met Lys Arg His Asp Phe Phe Lys Ser Ala Met Pro Glu Gly Tyr
    130                 135                 140

Val Gln Glu Arg Thr Ile Ser Phe Lys Asp Asp Gly Lys Tyr Lys Thr
145                 150                 155                 160

Arg Ala Val Val Lys Phe Glu Gly Asp Thr Leu Val Asn Arg Ile Glu
                165                 170                 175

Leu Lys Gly Thr Asp Phe Lys Glu Asp Gly Asn Ile Leu Gly His Lys
            180                 185                 190

Leu Glu Tyr Asn Phe Asn Ser His Asn Val Tyr Ile Thr Ala Asp Lys
        195                 200                 205

Gln Lys Asn Gly Ile Lys Ala Asn Phe Thr Val Arg His Asn Val Glu
    210                 215                 220

Asp Gly Ser Val Gln Leu Ala Asp His Tyr Gln Gln Asn Thr Pro Ile
225                 230                 235                 240

Gly Asp Gly Pro Val Leu Leu Pro Asp Asn His Tyr Leu Ser Thr Gln
                245                 250                 255

Thr Val Leu Ser Lys Asp Pro Asn Glu Lys Arg Asp His Met Val Leu
            260                 265                 270

His Glu Tyr Val Asn Ala Ala Gly Ile Thr Leu Gly Met Asp Glu Leu
        275                 280                 285

Tyr Lys Leu Glu His His His His His His
    290                 295
```